US008722055B2

(12) United States Patent
El Kasmi et al.

(10) Patent No.: US 8,722,055 B2
(45) Date of Patent: May 13, 2014

(54) **SYNTHETIC *STREPTOCOCCUS PNEUMONIAE* VACCINE**

(75) Inventors: Karim C. El Kasmi, Denver, CO (US);
Brad Jordan, Thousand Oaks, CA (US);
Richard Kriwacki, Memphis, TN (US);
Beth Mann, Brownsville, TN (US);
Carlos J. Orihuela, San Antonio, TX (US); Elaine Tuomanen, Germantown, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 1199 days.

(21) Appl. No.: 12/442,044

(22) PCT Filed: Sep. 26, 2007

(86) PCT No.: PCT/US2007/079527
§ 371 (c)(1),
(2), (4) Date: Nov. 30, 2009

(87) PCT Pub. No.: WO2008/039838
PCT Pub. Date: Apr. 3, 2008

(65) Prior Publication Data
US 2010/0143394 A1    Jun. 10, 2010

Related U.S. Application Data

(60) Provisional application No. 60/847,446, filed on Sep. 27, 2006.

(51) Int. Cl.
| | |
|---|---|
| *A61K 39/02* | (2006.01) |
| *A61K 39/385* | (2006.01) |
| *A61K 39/085* | (2006.01) |
| *A61K 39/09* | (2006.01) |
| *A61K 45/00* | (2006.01) |
| *A61K 47/00* | (2006.01) |
| *A61K 47/48* | (2006.01) |
| *C07K 16/12* | (2006.01) |
| *C07K 14/005* | (2006.01) |

(52) U.S. Cl.
USPC .............. 424/190.1; 424/193.1; 424/194.1; 424/234.1; 424/237.1; 424/244.1; 424/278.1

(58) Field of Classification Search
CPC ..... A61K 38/00; A61K 39/02; A61K 39/085; A61K 2039/62; A61K 2039/64; A61K 2039/6037; A61K 2039/627; C07K 16/12; C07K 16/1275; C07K 14/005
USPC .......... 424/190.1, 193.1, 194.1, 244.1, 234.1, 424/278.1
See application file for complete search history.

(56) References Cited

U.S. PATENT DOCUMENTS

| | | | | |
|---|---|---|---|---|
| 6,245,335 | B1 * | 6/2001 | Masure et al. | 424/190.1 |
| 6,495,139 | B2 * | 12/2002 | Tuomanen et al. | 424/190.1 |
| 6,503,511 | B1 * | 1/2003 | Wizemann et al. | 424/190.1 |
| 6,784,164 | B2 * | 8/2004 | Masure et al. | 514/44 R |
| 6,858,706 | B2 * | 2/2005 | Tuomanen et al. | 530/350 |
| 6,936,252 | B2 * | 8/2005 | Gilbert et al. | 424/190.1 |
| 7,425,327 | B2 * | 9/2008 | Masure et al. | 424/130.1 |
| 7,479,282 | B2 * | 1/2009 | Tuomanen et al. | 424/244.1 |
| 7,632,515 | B2 * | 12/2009 | Gilbert et al. | 424/244.1 |
| 7,635,487 | B2 * | 12/2009 | Meinke et al. | 424/244.1 |
| 7,648,708 | B2 * | 1/2010 | Gilbert et al. | 424/244.1 |
| 7,713,534 | B2 * | 5/2010 | Gilbert et al. | 424/244.1 |
| 7,722,888 | B2 * | 5/2010 | Gilbert et al. | 424/244.1 |
| 8,110,199 | B2 * | 2/2012 | Gilbert et al. | 424/244.1 |
| 2003/0096950 | A1 * | 5/2003 | Tuomanen et al. | 530/350 |
| 2003/0138447 | A1 * | 7/2003 | Wizemann et al. | 424/190.1 |
| 2004/0120966 | A1 * | 6/2004 | Tuomanen et al. | 424/184.1 |
| 2005/0142145 | A1 * | 6/2005 | Wizemann et al. | 424/190.1 |
| 2005/0205069 | A1 * | 9/2005 | Lewis et al. | 123/491 |
| 2005/0208069 | A1 * | 9/2005 | Tuomanen et al. | 424/190.1 |
| 2010/0143394 | A1 * | 6/2010 | El Kasmi et al. | 424/190.1 |

FOREIGN PATENT DOCUMENTS

| | | |
|---|---|---|
| WO | WO 99/51187 A2 * | 10/1999 |
| WO | WO 99/51266 | 10/1999 |
| WO | WO 99/51266 A2 * | 10/1999 |
| WO | WO 00/06737 A2 * | 2/2000 |
| WO | WO 2004/020609 A2 * | 3/2004 |
| WO | WO 2008/039838 A2 * | 4/2008 |
| WO | WO 2012/134975 A1 * | 10/2012 |

OTHER PUBLICATIONS

Jedrzejas, Microbiol. Mol. Biol. Rev. 2001, 65(2):187-207.*
Greenspan et al (Nature Biotechnology 7: 936-937, 1999).*

(Continued)

*Primary Examiner* — Nita M Minnifield
(74) *Attorney, Agent, or Firm* — Alston & Bird LLP

(57) ABSTRACT

Compositions and methods for preventing and treating pneumococcal infections are provided. Compositions include novel polypeptides comprising an amino acid sequence corresponding to the R2*i* or R22 domain of CbpA or a consensus sequence of one of these domains, and variants and fragments thereof, wherein the polypeptide is stabilized in a desired conformation, particularly a loop conformation. The polypeptides of the invention may be engineered to comprise a first and a second cysteine residue, thereby resulting in the formation of a disulfide bond that stabilizes the polypeptide in the desired conformation. Alternatively, a polypeptide of the invention may be modified to create a synthetic linkage between a first and second amino acid residue present within the polypeptide, wherein the synthetic linkage stabilizes the polypeptide in the desired conformation. The polypeptides of the invention may further comprise an amino acid sequence for a T cell epitope. Compositions further include isolated nucleic acid molecules that encode the polypeptides of the invention, immunogenic compositions and vaccines comprising the disclosed polypeptides, and antibodies specific for these polypeptides.

30 Claims, 24 Drawing Sheets

(56) References Cited

OTHER PUBLICATIONS

Burgess et al., JCB, 1990, 111:2129-2138.*
Lazar et al., Molecular and Cellular Biology, 1988, 8:1247-1252.*
Thomas E. Creighton, In: "Proteins: Structures and Molecular Properties, 1984", (pp. 314-315).*
Blythe et al, Protein Science, 2005, 14:246-248.*
Houghten et al (Vaccine 86, 1986, pp. 21-25).*
Bixler et al, Synthetic Vaccines, vol. 1, 1987, pp. 39-71.*
Bowie et al., Science, 1990, vol. 247, pp. 1306-1310.*
Kumar et al. PNAS 87: 1337-1341 Feb. 1991.*
Thomas E. Creighton, In: "Protein Structure: A Practical Approach", 1989; pp. 184-186.*
Nosoh, Y. et al in "Protein Stability and Stabilization through Protein Engineering, 1991", chapter 7, p. 197.*
Elm, C., "Characterization of the Interaction of the Pneumococcal Surface Protein SpsA with the Human Polymeric Immunoglobulin Receptor (hpIgR)," *Indian Journal of Medical Research*, 2004, pp. 61-65, vol. 119(s).
Gosink, K.K., et al., "Role of Novel Choline Binding Proteins in Virulence of *Streptococcus pneumoniae*," *Infection and Immunity, American Society for Microbiology*, 2000, pp. 5690-5695, vol. 68(10).
Luo, R., et al., "Solution Structure of Choline Building Protein A. the Major Adhesin of *Streptococcus pneumoniae*," *European Molecular Biology Organization*, 2005, vol. 24(1).
Database Accession No. AAY49143, Oct. 14, 1999.
Database Accession No. ARD10815, Sep. 23, 2004.

\* cited by examiner

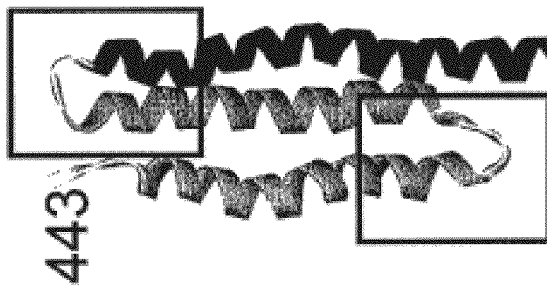

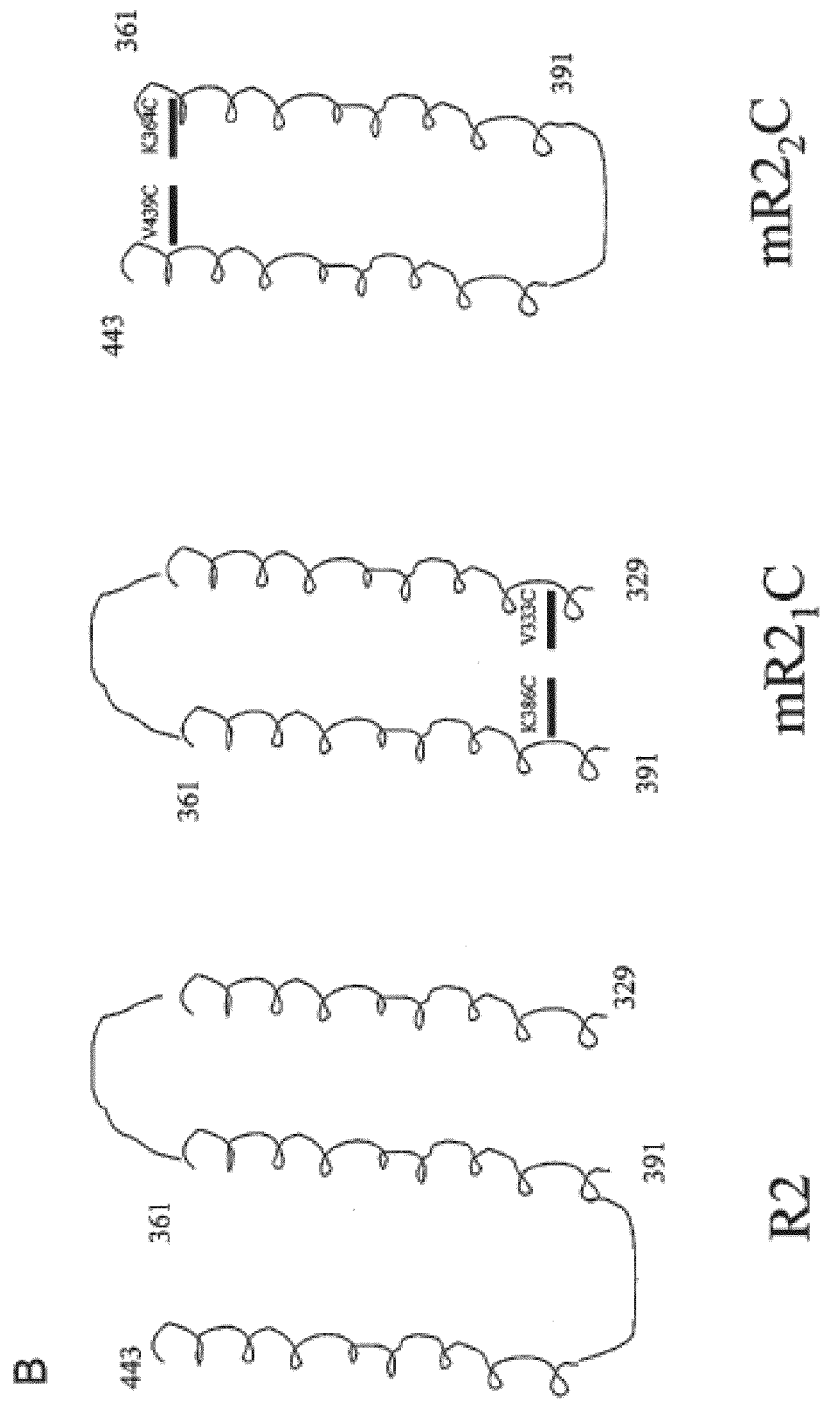

Survival of rCbpA Vaccinated Mice with *S. Pneumoniae Challenge*

A

B

Survival of rCbpA Vaccinated Mice with *S. Pneumoniae* Challenge

Changes in S. Pneumoniae Blood Titers

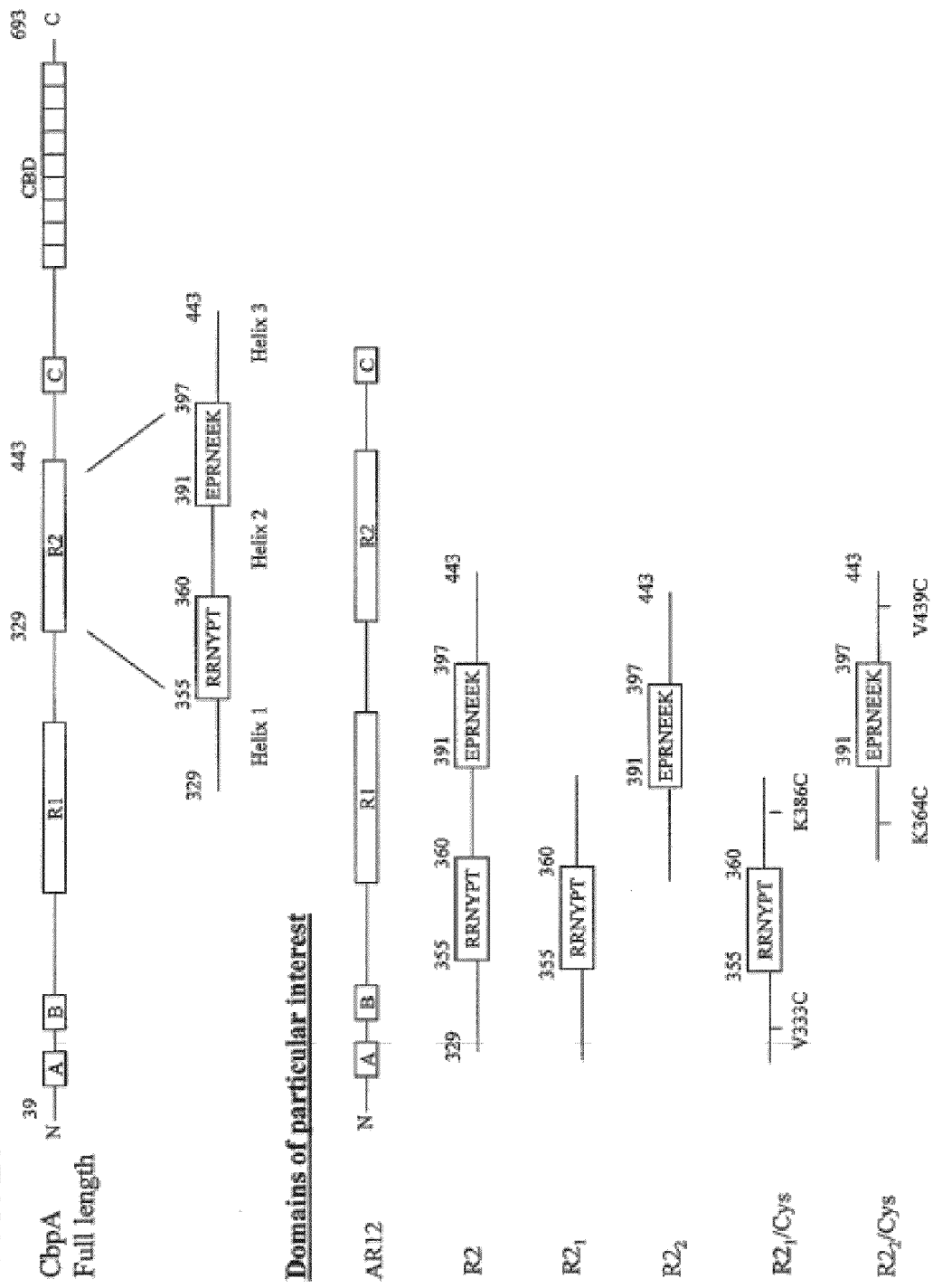

```
SEQUENCE LISTING

<160> NUMBER OF SEQ ID NOS: 74

<210> SEQ ID NO 1
<211> LENGTH: 693
<212> TYPE: PRT
<213> ORGANISM: Streptococcus pneumoniae

<400> SEQUENCE: 1

Met Phe Ala Ser Lys Ser Glu Arg Lys Val His Tyr Ser Ile Arg Lys
1               5                   10                  15

Phe Ser Val Gly Val Ala Ser Val Val Val Ala Ser Leu Val Met Gly
            20                  25                  30

Ser Val Val His Ala Thr Glu Asn Glu Gly Ala Thr Gln Val Pro Thr
        35                  40                  45

Ser Ser Asn Arg Ala Asn Glu Ser Gln Ala Glu Gln Gly Glu Gln Pro
    50                  55                  60

Lys Lys Leu Asp Ser Glu Arg Asp Lys Ala Arg Lys Glu Val Glu Glu
65                  70                  75                  80

Tyr Val Lys Lys Ile Val Gly Glu Ser Tyr Ala Lys Ser Thr Lys Lys
                85                  90                  95

Arg His Thr Ile Thr Val Ala Leu Val Asn Glu Leu Asn Asn Ile Lys
            100                 105                 110

Asn Glu Tyr Leu Asn Lys Ile Val Glu Ser Thr Ser Glu Ser Gln Leu
        115                 120                 125

Gln Ile Leu Met Met Glu Ser Arg Ser Lys Val Asp Glu Ala Val Ser
    130                 135                 140
```

```
Lys Phe Glu Lys Asp Ser Ser Ser Ser Ser Asp Ser Thr
145             150             155             160

Lys Pro Glu Ala Ser Asp Thr Ala Lys Pro Asn Lys Pro Thr Glu Pro
            165             170             175

Gly Glu Lys Val Ala Glu Ala Lys Lys Val Glu Ala Glu Lys
            180             185             190

Lys Ala Lys Asp Gln Lys Glu Glu Asp Arg Arg Asn Tyr Pro Thr Ile
        195             200             205

Thr Tyr Lys Thr Leu Glu Leu Glu Ile Ala Glu Ser Asp Val Glu Val
        210             215             220

Lys Lys Ala Glu Leu Glu Leu Val Lys Val Lys Ala Asn Glu Pro Arg
225             230             235             240

Asp Glu Gln Lys Ile Lys Gln Ala Glu Ala Glu Val Glu Ser Lys Gln
                245             250             255

Ala Glu Ala Thr Arg Leu Lys Lys Ile Lys Thr Asp Arg Glu Glu Ala
            260             265             270

Glu Glu Glu Ala Lys Arg Arg Ala Asp Ala Lys Glu Gln Gly Lys Pro
        275             280             285

Lys Gly Arg Ala Lys Arg Gly Val Pro Gly Glu Leu Ala Thr Pro Asp
290             295             300

Lys Lys Glu Asn Asp Ala Lys Ser Ser Asp Ser Ser Val Gly Glu Glu
305             310             315             320

Thr Leu Pro Ser Pro Ser Leu Lys Pro Glu Lys Lys Val Ala Glu Ala
            325             330             335

Glu Lys Lys Val Glu Ala Lys Lys Lys Ala Glu Asp Gln Lys Glu
            340             345             350

Glu Asp Arg Arg Asn Tyr Pro Thr Asn Thr Tyr Lys Thr Leu Glu Leu
        355             360             365

Glu Ile Ala Glu Ser Asp Val Glu Val Lys Lys Ala Glu Leu Glu Leu
        370             375             380

Val Lys Glu Glu Ala Lys Glu Pro Arg Asn Glu Glu Lys Val Lys Gln
385             390             395             400

Ala Lys Ala Glu Val Glu Ser Lys Lys Ala Glu Ala Thr Arg Leu Glu
            405             410             415

Lys Ile Lys Thr Asp Arg Lys Lys Ala Glu Glu Glu Ala Lys Arg Lys
            420             425             430

Ala Ala Glu Glu Asp Lys Val Lys Glu Lys Pro Ala Glu Gln Pro Gln
        435             440             445

Pro Ala Pro Ala Pro Lys Ala Glu Lys Pro Ala Pro Ala Pro Lys Pro
450             455             460

Glu Asn Pro Ala Glu Gln Pro Lys Ala Glu Lys Pro Ala Asp Gln Gln
465             470             475             480

Ala Glu Glu Asp Tyr Ala Arg Arg Ser Glu Glu Glu Tyr Asn Arg Leu
            485             490             495

Thr Gln Gln Gln Pro Pro Lys Thr Glu Lys Pro Ala Gln Pro Ser Thr
            500             505             510

Pro Lys Thr Gly Trp Lys Gln Glu Asn Gly Met Trp Tyr Phe Tyr Asn
        515             520             525

Thr Asp Gly Ser Met Ala Thr Gly Trp Leu Gln Asn Gly Ser Trp
        530             535             540

Tyr Tyr Leu Asn Ser Asn Gly Ala Met Ala Thr Gly Trp Leu Gln Asn
545             550             555             560

Asn Gly Ser Trp Tyr Tyr Leu Asn Ala Asn Gly Ser Met Ala Thr Gly
```

```
                    565                 570                 575
Trp Leu Gln Asn Asn Gly Ser Trp Tyr Tyr Leu Asn Ala Asn Gly Ser
            580                 585                 590

Met Ala Thr Gly Trp Leu Gln Tyr Asn Gly Ser Trp Tyr Tyr Leu Asn
        595                 600                 605

Ala Asn Gly Ser Met Ala Thr Gly Trp Leu Gln Tyr Asn Gly Ser Trp
    610                 615                 620

Tyr Tyr Leu Asn Ala Asn Gly Asp Met Ala Thr Gly Trp Val Lys Asp
625                 630                 635                 640

Gly Asp Thr Trp Tyr Tyr Leu Glu Ala Ser Gly Ala Met Lys Ala Ser
                645                 650                 655

Gln Trp Phe Lys Val Ser Asp Lys Trp Tyr Tyr Val Asn Gly Ser Gly
            660                 665                 670

Ala Leu Ala Val Asn Thr Thr Val Asp Gly Tyr Gly Val Asn Ala Asn
        675                 680                 685

Gly Glu Trp Val Asn
    690

<210> SEQ ID NO 2
<211> LENGTH: 2082
<212> TYPE: DNA
<213> ORGANISM: Streptococcus pneumoniae
<220> FEATURE:
<221> NAME/KEY: CDS
<222> LOCATION: (1)...(2082)
<221> NAME/KEY: misc_feature
<222> LOCATION: (0)...(0)
<223> OTHER INFORMATION: nucleotide sequence encoding the full length
      CbpA of SEQ ID NO:1 (GenBank Accession No. AE005672)

<400> SEQUENCE: 2 atg ttt gca tca aaa agc gaa aga aaa gta cat tat tca att cgt aaa      48
Met Phe Ala Ser Lys Ser Glu Arg Lys Val His Tyr Ser Ile Arg Lys
  1               5                  10                  15 ttt agt gtt gga gta gct agt gta gtt gtt gcc agt ctt gtt atg gga      96
Phe Ser Val Gly Val Ala Ser Val Val Val Ala Ser Leu Val Met Gly
                 20                  25                  30 agt gtg gtt cat gcg aca gag aac gag gga gct acc caa gta ccc act     144
Ser Val Val His Ala Thr Glu Asn Glu Gly Ala Thr Gln Val Pro Thr
             35                  40                  45 tct tct aat agg gca aat gaa agt cag gca gaa caa gga gaa caa cct     192
Ser Ser Asn Arg Ala Asn Glu Ser Gln Ala Glu Gln Gly Glu Gln Pro
         50                  55                  60 aaa aaa ctc gat tca gaa cga gat aag gca agg aaa gag gtc gag gaa     240
Lys Lys Leu Asp Ser Glu Arg Asp Lys Ala Arg Lys Glu Val Glu Glu
 65                  70                  75                  80 tat gta aaa aaa ata gtg ggt gag agc tat gca aaa tca act aaa aag     288
Tyr Val Lys Lys Ile Val Gly Glu Ser Tyr Ala Lys Ser Thr Lys Lys
                 85                  90                  95 cga cat aca att act gta gct cta gtt aac gag ttg aac aac att aag     336
Arg His Thr Ile Thr Val Ala Leu Val Asn Glu Leu Asn Asn Ile Lys
            100                 105                 110 aac gag tat ttg aat aaa ata gtt gaa tca acc tca gaa agc caa cta     384
Asn Glu Tyr Leu Asn Lys Ile Val Glu Ser Thr Ser Glu Ser Gln Leu
        115                 120                 125 cag ata ctg atg atg gag agt cga tca aaa gta gat gaa gct gtg tct     432
Gln Ile Leu Met Met Glu Ser Arg Ser Lys Val Asp Glu Ala Val Ser
    130                 135                 140 aag ttt gaa aag gac tca tct tct tcg tca agt tca gac tct tcc act     480
Lys Phe Glu Lys Asp Ser Ser Ser Ser Ser Ser Asp Ser Ser Thr
145                 150                 155                 160
```

```
aaa ccg gaa gct tca gat aca gcg aag cca aac aag ccg aca gaa cca         528
Lys Pro Glu Ala Ser Asp Thr Ala Lys Pro Asn Lys Pro Thr Glu Pro
            165                 170                 175 gga gaa aag gta gca gaa gct aag aag aag gtt gaa gaa gct gag aaa         576
Gly Glu Lys Val Ala Glu Ala Lys Lys Lys Val Glu Glu Ala Glu Lys
        180                 185                 190 aaa gcc aag gat caa aaa gaa gaa gat cgt cgt aac tac cca acc att         624
Lys Ala Lys Asp Gln Lys Glu Glu Asp Arg Arg Asn Tyr Pro Thr Ile
    195                 200                 205 act tac aaa acg ctt gaa ctt gaa att gct gag tcc gat gtg gaa gtt         672
Thr Tyr Lys Thr Leu Glu Leu Glu Ile Ala Glu Ser Asp Val Glu Val
210                 215                 220 aaa aaa gcg gag ctt gaa cta gta aaa gtg aaa gct aac gaa cct cga         720
Lys Lys Ala Glu Leu Glu Leu Val Lys Val Lys Ala Asn Glu Pro Arg
225                 230                 235                 240 gac gag caa aaa att aag caa gca gaa gcg gaa gtt gag agt aaa caa         768
Asp Glu Gln Lys Ile Lys Gln Ala Glu Ala Glu Val Glu Ser Lys Gln
                245                 250                 255 gct gag gct aca agg tta aaa aaa atc aag aca gat cgt gaa gaa gca         816
Ala Glu Ala Thr Arg Leu Lys Lys Ile Lys Thr Asp Arg Glu Glu Ala
            260                 265                 270 gaa gaa gaa gct aaa cga aga gca gat gct aaa gag caa ggt aaa cca         864
Glu Glu Glu Ala Lys Arg Arg Ala Asp Ala Lys Glu Gln Gly Lys Pro
        275                 280                 285 aag ggg cgg gca aaa cga gga gtt cct gga gag cta gca aca cct gat         912
Lys Gly Arg Ala Lys Arg Gly Val Pro Gly Glu Leu Ala Thr Pro Asp
    290                 295                 300 aaa aaa gaa aat gat gcg aag tct tca gat tct agc gta ggt gaa gaa         960
Lys Lys Glu Asn Asp Ala Lys Ser Ser Asp Ser Ser Val Gly Glu Glu
305                 310                 315                 320 act ctt cca agc cca tcc ctg aaa cca gaa aaa aag gta gca gaa gct        1008
Thr Leu Pro Ser Pro Ser Leu Lys Pro Glu Lys Lys Val Ala Glu Ala
                325                 330                 335 gag aag aag gtt gaa gaa gct aag aaa aaa gcc gag gat caa aaa gaa        1056
Glu Lys Lys Val Glu Glu Ala Lys Lys Lys Ala Glu Asp Gln Lys Glu
            340                 345                 350 gaa gat cgc cgt aac tac cca acc aat act tac aaa acg ctt gaa ctt        1104
Glu Asp Arg Arg Asn Tyr Pro Thr Asn Thr Tyr Lys Thr Leu Glu Leu
        355                 360                 365 gaa att gct gag tcc gat gtg gaa gtt aaa aaa gcg gag ctt gaa cta        1152
Glu Ile Ala Glu Ser Asp Val Glu Val Lys Lys Ala Glu Leu Glu Leu
    370                 375                 380 gta aaa gag gaa gct aag gaa cct cga aac gag gaa aaa gtt aag caa        1200
Val Lys Glu Glu Ala Lys Glu Pro Arg Asn Glu Glu Lys Val Lys Gln
385                 390                 395                 400 gca aaa gcg gaa gtt gag agt aaa aaa gct gag gct aca agg tta gaa        1248
Ala Lys Ala Glu Val Glu Ser Lys Lys Ala Glu Ala Thr Arg Leu Glu
                405                 410                 415 aaa atc aag aca gat cgt aaa aaa gca gaa gaa gaa gct aaa cga aaa        1296
Lys Ile Lys Thr Asp Arg Lys Lys Ala Glu Glu Glu Ala Lys Arg Lys
            420                 425                 430 gca gca gaa gaa gat aaa gtt aaa gaa aaa cca gct gaa caa cca caa        1344
Ala Ala Glu Glu Asp Lys Val Lys Glu Lys Pro Ala Glu Gln Pro Gln
        435                 440                 445 cca gcg ccg gct cca aaa gca gaa aaa cca gct cca gct cca aaa cca        1392
Pro Ala Pro Ala Pro Lys Ala Glu Lys Pro Ala Pro Ala Pro Lys Pro
    450                 455                 460 gag aat cca gct gaa caa cca aaa gca gaa aaa cca gct gat caa caa        1440
Glu Asn Pro Ala Glu Gln Pro Lys Ala Glu Lys Pro Ala Asp Gln Gln
465                 470                 475                 480
```

```
gct gaa gaa gac tat gct cgt aga tca gaa gaa gaa tat aat cgc ttg      1488
Ala Glu Glu Asp Tyr Ala Arg Arg Ser Glu Glu Glu Tyr Asn Arg Leu
                485                 490                 495 act caa cag caa ccg cca aaa act gaa aaa cca gca caa cca tct act      1536
Thr Gln Gln Gln Pro Pro Lys Thr Glu Lys Pro Ala Gln Pro Ser Thr
        500                 505                 510 cca aaa aca ggc tgg aaa caa gaa aac ggt atg tgg tac ttc tac aat      1584
Pro Lys Thr Gly Trp Lys Gln Glu Asn Gly Met Trp Tyr Phe Tyr Asn
    515                 520                 525 act gat ggt tca atg gcg aca gga tgg ctc caa aac aat ggc tca tgg      1632
Thr Asp Gly Ser Met Ala Thr Gly Trp Leu Gln Asn Asn Gly Ser Trp
530                 535                 540 tac tac ctc aac agc aat ggc gct atg gcg aca gga tgg ctc caa aac      1680
Tyr Tyr Leu Asn Ser Asn Gly Ala Met Ala Thr Gly Trp Leu Gln Asn
545                 550                 555                 560 aat ggt tca tgg tac tat cta aac gct aat ggt tca atg gca aca gga      1728
Asn Gly Ser Trp Tyr Tyr Leu Asn Ala Asn Gly Ser Met Ala Thr Gly
                565                 570                 575 tgg ctc caa aac aat ggt tca tgg tac tac cta aac gct aat ggt tca      1776
Trp Leu Gln Asn Asn Gly Ser Trp Tyr Tyr Leu Asn Ala Asn Gly Ser
            580                 585                 590 atg gcg aca gga tgg ctc caa tac aat ggc tca tgg tac tac cta aac      1824
Met Ala Thr Gly Trp Leu Gln Tyr Asn Gly Ser Trp Tyr Tyr Leu Asn
        595                 600                 605 gct aat ggt tca atg gcg aca gga tgg ctc caa tac aat ggc tca tgg      1872
Ala Asn Gly Ser Met Ala Thr Gly Trp Leu Gln Tyr Asn Gly Ser Trp
    610                 615                 620 tac tac cta aac gct aat ggt gat atg gcg aca ggt tgg gtg aaa gat      1920
Tyr Tyr Leu Asn Ala Asn Gly Asp Met Ala Thr Gly Trp Val Lys Asp
625                 630                 635                 640 gga gat acc tgg tac tat ctt gaa gca tca ggt gct atg aaa gca agc      1968
Gly Asp Thr Trp Tyr Tyr Leu Glu Ala Ser Gly Ala Met Lys Ala Ser
                645                 650                 655 caa tgg ttc aaa gta tca gat aaa tgg tac tat gtc aat ggc tca ggt      2016
Gln Trp Phe Lys Val Ser Asp Lys Trp Tyr Tyr Val Asn Gly Ser Gly
            660                 665                 670 gcc ctt gca gtc aac aca act gta gat ggc tat gga gtc aat gcc aat      2064
Ala Leu Ala Val Asn Thr Thr Val Asp Gly Tyr Gly Val Asn Ala Asn
        675                 680                 685 ggt gaa tgg gta aac taa                                              2082
Gly Glu Trp Val Asn *
    690
```

<210> SEQ ID NO 3
<211> LENGTH: 472
<212> TYPE: PRT
<213> ORGANISM: Streptococcus pneumoniae

<400> SEQUENCE: 3

```
Glu Asn Glu Gly Ala Thr Gln Val Pro Thr Ser Ser Asn Arg Ala Asn
 1               5                  10                  15

Glu Ser Gln Ala Glu Gln Gly Glu Gln Pro Lys Lys Leu Asp Ser Glu
            20                  25                  30

Arg Asp Lys Ala Arg Lys Glu Val Glu Glu Tyr Val Lys Lys Ile Val
        35                  40                  45

Gly Glu Ser Tyr Ala Lys Ser Thr Lys Lys Arg His Thr Ile Thr Val
    50                  55                  60

Ala Leu Val Asn Glu Leu Asn Asn Ile Lys Asn Glu Tyr Leu Asn Lys
65                  70                  75                  80
```

```
Ile Val Glu Ser Thr Ser Glu Ser Gln Leu Gln Ile Leu Met Met Glu
                85                  90                  95

Ser Arg Ser Lys Val Asp Glu Ala Val Ser Lys Phe Glu Lys Asp Ser
            100                 105                 110

Ser Ser Ser Ser Ser Asp Ser Ser Thr Lys Pro Glu Ala Ser Asp
        115                 120                 125

Thr Ala Lys Pro Asn Lys Pro Thr Glu Pro Gly Glu Lys Val Ala Glu
    130                 135                 140

Ala Lys Lys Lys Val Glu Glu Ala Gly Lys Lys Ala Lys Asp Gln Lys
145                 150                 155                 160

Glu Glu Asp Arg Arg Asn Tyr Pro Thr Ile Thr Tyr Lys Thr Leu Glu
                165                 170                 175

Leu Glu Ile Ala Glu Ser Asp Val Glu Val Lys Lys Ala Glu Leu Glu
            180                 185                 190

Leu Val Lys Val Lys Ala Asn Glu Pro Arg Asp Glu Gln Lys Ile Lys
            195                 200                 205

Gln Ala Glu Ala Glu Val Glu Ser Lys Gln Ala Glu Ala Thr Arg Leu
        210                 215                 220

Lys Lys Ile Lys Thr Asp Arg Glu Glu Ala Glu Glu Ala Lys Arg
225                 230                 235                 240

Arg Ala Asp Ala Lys Glu Gln Gly Lys Pro Lys Gly Arg Ala Lys Arg
                245                 250                 255

Gly Val Pro Gly Glu Leu Ala Thr Pro Asp Lys Lys Glu Asn Asp Ala
                260                 265                 270

Lys Ser Ser Asp Ser Ser Val Gly Glu Glu Thr Leu Pro Ser Pro Ser
            275                 280                 285

Leu Lys Pro Glu Lys Lys Val Ala Glu Ala Glu Lys Lys Val Glu Glu
    290                 295                 300

Ala Lys Lys Lys Ala Glu Asp Gln Lys Glu Glu Asp Arg Arg Asn Tyr
305                 310                 315                 320

Pro Thr Asn Thr Tyr Lys Thr Leu Glu Leu Glu Ile Ala Glu Ser Asp
                325                 330                 335

Val Glu Val Lys Lys Ala Glu Leu Glu Leu Val Lys Lys Glu Ala Lys
            340                 345                 350

Glu Pro Arg Asn Glu Glu Lys Val Lys Gln Ala Lys Ala Glu Val Glu
            355                 360                 365

Ser Lys Lys Ala Glu Ala Thr Arg Leu Glu Lys Ile Lys Thr Asp Arg
    370                 375                 380

Lys Lys Ala Glu Glu Ala Lys Arg Lys Ala Glu Glu Asp Lys
385                 390                 395                 400

Val Lys Glu Lys Pro Ala Glu Gln Pro Gln Pro Ala Pro Ala Pro Lys
                405                 410                 415

Ala Glu Lys Pro Ala Pro Ala Pro Lys Pro Glu Asn Pro Ala Glu Gln
            420                 425                 430

Pro Lys Ala Glu Lys Pro Ala Asp Gln Gln Ala Glu Glu Asp Tyr Ala
        435                 440                 445

Arg Arg Ser Glu Glu Glu Tyr Asn Arg Leu Thr Gln Gln Gln Pro Pro
        450                 455                 460

Lys Thr Glu Lys Pro Ala Gln Pro
465                 470

<210> SEQ ID NO 4
<211> LENGTH: 1416
<212> TYPE: DNA
<213> ORGANISM: Streptococcus pneumoniae
```

-continued

```
<220> FEATURE:
<221> NAME/KEY: misc_feature
<222> LOCATION: (0)...(0)
<223> OTHER INFORMATION: Nucleotide sequence encoding the N-terminal
      amino acid sequence of CbpA set forth in SEQ ID NO:3,
      which corresponds to residues 39-510 of SEQ ID
      NO:1.
<221> NAME/KEY: CDS
<222> LOCATION: (1)...(1416)

<400> SEQUENCE: 4 gag aac gag gga gct acc caa gta ccc act tct tct aat agg gca aat      48
Glu Asn Glu Gly Ala Thr Gln Val Pro Thr Ser Ser Asn Arg Ala Asn
 1               5                  10                  15 gaa agt cag gca gaa caa gga gaa caa cct aaa aaa ctc gat tca gaa      96
Glu Ser Gln Ala Glu Gln Gly Glu Gln Pro Lys Lys Leu Asp Ser Glu
                 20                  25                  30 cga gat aag gca agg aaa gag gtc gag gaa tat gta aaa aaa ata gtg     144
Arg Asp Lys Ala Arg Lys Glu Val Glu Glu Tyr Val Lys Lys Ile Val
             35                  40                  45 ggt gag agc tat gca aaa tca act aaa aag cga cat aca att act gta     192
Gly Glu Ser Tyr Ala Lys Ser Thr Lys Lys Arg His Thr Ile Thr Val
 50                  55                  60 gct cta gtt aac gag ttg aac aac att aag aac gag tat ttg aat aaa     240
Ala Leu Val Asn Glu Leu Asn Asn Ile Lys Asn Glu Tyr Leu Asn Lys
 65                  70                  75                  80 ata gtt gaa tca acc tca gaa agc caa cta cag ata ctg atg atg gag     288
Ile Val Glu Ser Thr Ser Glu Ser Gln Leu Gln Ile Leu Met Met Glu
                 85                  90                  95 agt cga tca aaa gta gat gaa gct gtg tct aag ttt gaa aag gac tca     336
Ser Arg Ser Lys Val Asp Glu Ala Val Ser Lys Phe Glu Lys Asp Ser
                100                 105                 110 tct tct tcg tca agt tca gac tct tcc act aaa ccg gaa gct tca gat     384
Ser Ser Ser Ser Ser Ser Asp Ser Ser Thr Lys Pro Glu Ala Ser Asp
            115                 120                 125 aca gcg aag cca aac aag ccg aca gaa cca gga gaa aag gta gca gaa     432
Thr Ala Lys Pro Asn Lys Pro Thr Glu Pro Gly Glu Lys Val Ala Glu
        130                 135                 140 gct aag aag aag gtt gaa gaa gct gag aaa aaa gcc aag gat caa aaa     480
Ala Lys Lys Lys Val Glu Glu Ala Glu Lys Lys Ala Lys Asp Gln Lys
145                 150                 155                 160 gaa gaa gat cgt cgt aac tac cca acc att act tac aaa acg ctt gaa     528
Glu Glu Asp Arg Arg Asn Tyr Pro Thr Ile Thr Tyr Lys Thr Leu Glu
                165                 170                 175 ctt gaa att gct gag tcc gat gtg gaa gtt aaa aaa gcg gag ctt gaa     576
Leu Glu Ile Ala Glu Ser Asp Val Glu Val Lys Lys Ala Glu Leu Glu
            180                 185                 190 cta gta aaa gtg aaa gct aac gaa cct cga gac gag caa aaa att aag     624
Leu Val Lys Val Lys Ala Asn Glu Pro Arg Asp Glu Gln Lys Ile Lys
        195                 200                 205 caa gca gaa gcg gaa gtt gag agt aaa caa gct gag gct aca agg tta     672
Gln Ala Glu Ala Glu Val Glu Ser Lys Gln Ala Glu Ala Thr Arg Leu
    210                 215                 220 aaa aaa atc aag aca gat cgt gaa gaa gca gaa gaa gaa gct aaa cga     720
Lys Lys Ile Lys Thr Asp Arg Glu Glu Ala Glu Glu Glu Ala Lys Arg
225                 230                 235                 240 aga gca gat gct aaa gag caa ggt aaa cca aag ggg cgg gca aaa cga     768
Arg Ala Asp Ala Lys Glu Gln Gly Lys Pro Lys Gly Arg Ala Lys Arg
                245                 250                 255 gga gtt cct gga gag cta gca aca cct gat aaa aaa gaa aat gat gcg     816
Gly Val Pro Gly Glu Leu Ala Thr Pro Asp Lys Lys Glu Asn Asp Ala
            260                 265                 270
```

```
aag tct tca gat tct agc gta ggt gaa gaa act ctt cca agc cca tcc      864
Lys Ser Ser Asp Ser Ser Val Gly Glu Glu Thr Leu Pro Ser Pro Ser
    275                 280                 285 ctg aaa cca gaa aaa aag gta gca gaa gct gag aag aag gtt gaa gaa      912
Leu Lys Pro Glu Lys Lys Val Ala Glu Ala Glu Lys Lys Val Glu Glu
290                 295                 300 gct aag aaa aaa gcc gag gat caa aaa gaa gaa gat cgc cgt aac tac      960
Ala Lys Lys Lys Ala Glu Asp Gln Lys Glu Glu Asp Arg Arg Asn Tyr
305                 310                 315                 320 cca acc aat act tac aaa acg ctt gaa ctt gaa att gct gag tcc gat     1008
Pro Thr Asn Thr Tyr Lys Thr Leu Glu Leu Glu Ile Ala Glu Ser Asp
                325                 330                 335 gtg gaa gtt aaa aaa gcg gag ctt gaa cta gta aaa gag gaa gct aag     1056
Val Glu Val Lys Lys Ala Glu Leu Glu Leu Val Lys Glu Glu Ala Lys
            340                 345                 350 gaa cct cga aac gag gaa aaa gtt aag caa gca aaa gcg gaa gtt gag     1104
Glu Pro Arg Asn Glu Glu Lys Val Lys Gln Ala Lys Ala Glu Val Glu
        355                 360                 365 agt aaa aaa gct gag gct aca agg tta gaa aaa atc aag aca gat cgt     1152
Ser Lys Lys Ala Glu Ala Thr Arg Leu Glu Lys Ile Lys Thr Asp Arg
    370                 375                 380 aaa aaa gca gaa gaa gaa gct aaa cga aaa gca gca gaa gaa gat aaa     1200
Lys Lys Ala Glu Glu Glu Ala Lys Arg Lys Ala Ala Glu Glu Asp Lys
385                 390                 395                 400 gtt aaa gaa aaa cca gct gaa caa cca caa cca gcg ccg gct cca aaa     1248
Val Lys Glu Lys Pro Ala Glu Gln Pro Gln Pro Ala Pro Ala Pro Lys
                405                 410                 415 gca gaa aaa cca gct cca gct cca aaa cca gag aat cca gct gaa caa     1296
Ala Glu Lys Pro Ala Pro Ala Pro Lys Pro Glu Asn Pro Ala Glu Gln
            420                 425                 430 cca aaa gca gaa aaa cca gct gat caa caa gct gaa gaa gac tat gct     1344
Pro Lys Ala Glu Lys Pro Ala Asp Gln Gln Ala Glu Glu Asp Tyr Ala
        435                 440                 445 cgt aga tca gaa gaa gaa tat aat cgc ttg act caa cag caa ccg         1392
Arg Arg Ser Glu Glu Glu Tyr Asn Arg Leu Thr Gln Gln Gln Pro
    450                 455                 460 aaa act gaa aaa cca gca caa cca                                     1416
Lys Thr Glu Lys Pro Ala Gln Pro
465                 470

<210> SEQ ID NO 5
<211> LENGTH: 115
<212> TYPE: PRT
<213> ORGANISM: Streptococcus pneumoniae

<400> SEQUENCE: 5

Pro Glu Lys Lys Val Ala Glu Ala Glu Lys Lys Val Glu Glu Ala Lys
1               5                   10                  15

Lys Lys Ala Glu Asp Gln Lys Glu Glu Asp Arg Arg Asn Tyr Pro Thr
            20                  25                  30

Asn Thr Tyr Lys Thr Leu Glu Leu Glu Ile Ala Glu Ser Asp Val Glu
        35                  40                  45

Val Lys Lys Ala Glu Leu Glu Leu Val Lys Glu Glu Ala Lys Glu Pro
    50                  55                  60

Arg Asn Glu Glu Lys Val Lys Gln Ala Lys Ala Glu Val Glu Ser Lys
65                  70                  75                  80

Lys Ala Glu Ala Thr Arg Leu Glu Lys Ile Lys Thr Asp Arg Lys Lys
                85                  90                  95

Ala Glu Glu Glu Ala Lys Arg Lys Ala Ala Glu Glu Asp Lys Val Lys
            100                 105                 110
```

```
Glu Lys Pro
        115

<210> SEQ ID NO 6
<211> LENGTH: 345
<212> TYPE: DNA
<213> ORGANISM: Streptococcus pneumoniae
<220> FEATURE:
<221> NAME/KEY: misc_feature
<222> LOCATION: (0)...(0)
<223> OTHER INFORMATION: Nucleotide sequence encoding the R2 polypeptide
      set forth in SEQ ID NO:5 corresponding to amino
      acid residues 329-443 of the CbpA protein from
      Streptococcus pneumoniae Tigr4 strain
<221> NAME/KEY: CDS
<222> LOCATION: (1)...(345)

<400> SEQUENCE: 6 cca gaa aaa aag gta gca gaa gct gag aag aag gtt gaa gaa gct aag      48
Pro Glu Lys Lys Val Ala Glu Ala Glu Lys Lys Val Glu Glu Ala Lys
 1               5                   10                  15 aaa aaa gcc gag gat caa aaa gaa gaa gat cgc cgt aac tac cca acc      96
Lys Lys Ala Glu Asp Gln Lys Glu Glu Asp Arg Arg Asn Tyr Pro Thr
             20                  25                  30 aat act tac aaa acg ctt gaa ctt gaa att gct gag tcc gat gtg gaa     144
Asn Thr Tyr Lys Thr Leu Glu Leu Glu Ile Ala Glu Ser Asp Val Glu
         35                  40                  45 gtt aaa aaa gcg gag ctt gaa cta gta aaa gag gaa gct aag gaa cct     192
Val Lys Lys Ala Glu Leu Glu Leu Val Lys Glu Glu Ala Lys Glu Pro
     50                  55                  60 cga aac gag gaa aaa gtt aag caa gca aaa gcg gaa gtt gag agt aaa     240
Arg Asn Glu Glu Lys Val Lys Gln Ala Lys Ala Glu Val Glu Ser Lys
 65                  70                  75                  80 aaa gct gag gct aca agg tta gaa aaa atc aag aca gat cgt aaa aaa     288
Lys Ala Glu Ala Thr Arg Leu Glu Lys Ile Lys Thr Asp Arg Lys Lys
                 85                  90                  95 gca gaa gaa gaa gct aaa cga aaa gca gca gaa gaa gat aaa gtt aaa     336
Ala Glu Glu Glu Ala Lys Arg Lys Ala Ala Glu Glu Asp Lys Val Lys
            100                 105                 110 gaa aaa cca                                                         345
Glu Lys Pro
        115

<210> SEQ ID NO 7
<211> LENGTH: 63
<212> TYPE: PRT
<213> ORGANISM: Streptococcus pneumoniae

<400> SEQUENCE: 7

Pro Glu Lys Lys Val Ala Glu Ala Glu Lys Lys Val Glu Glu Ala Lys
 1               5                  10                  15

Lys Lys Ala Glu Asp Gln Lys Glu Glu Asp Arg Arg Asn Tyr Pro Thr
             20                  25                  30

Asn Thr Tyr Lys Thr Leu Glu Leu Glu Ile Ala Glu Ser Asp Val Glu
         35                  40                  45

Val Lys Lys Ala Glu Leu Glu Leu Val Lys Glu Glu Ala Lys Glu
     50                  55                  60

<210> SEQ ID NO 8
<211> LENGTH: 189
<212> TYPE: DNA
<213> ORGANISM: Streptococcus pneumoniae
<220> FEATURE:
<221> NAME/KEY: misc_feature
```

```
<222> LOCATION: (0)...(0)
<223> OTHER INFORMATION: Nucleotide sequence encoding the R21
      polypeptide set forth in SEQ ID NO:7 corresponding to residues
      329-391 of the CbpA protein from Streptococcus
      pneumoniae Tigr4 strain
<221> NAME/KEY: CDS
<222> LOCATION: (1)...(189)

<400> SEQUENCE: 8 cca gaa aaa aag gta gca gaa gct gag aag aag gtt gaa gaa gct aag      48
Pro Glu Lys Lys Val Ala Glu Ala Glu Lys Lys Val Glu Glu Ala Lys
  1               5                  10                  15 aaa aaa gcc gag gat caa aaa gaa gaa gat cgc cgt aac tac cca acc      96
Lys Lys Ala Glu Asp Gln Lys Glu Glu Asp Arg Arg Asn Tyr Pro Thr
             20                  25                  30 aat act tac aaa acg ctt gaa ctt gaa att gct gag tcc gat gtg gaa     144
Asn Thr Tyr Lys Thr Leu Glu Leu Glu Ile Ala Glu Ser Asp Val Glu
         35                  40                  45 gtt aaa aaa gcg gag ctt gaa cta gta aaa gag gaa gct aag gaa         189
Val Lys Lys Ala Glu Leu Glu Leu Val Lys Glu Glu Ala Lys Glu
     50                  55                  60

<210> SEQ ID NO 9
<211> LENGTH: 83
<212> TYPE: PRT
<213> ORGANISM: Streptococcus pneumoniae

<400> SEQUENCE: 9

Asn Thr Tyr Lys Thr Leu Glu Leu Glu Ile Ala Glu Ser Asp Val Glu
  1               5                  10                  15

Val Lys Lys Ala Glu Leu Glu Leu Val Lys Glu Glu Ala Lys Glu Pro
             20                  25                  30

Arg Asn Glu Glu Lys Val Lys Gln Ala Lys Ala Glu Val Glu Ser Lys
         35                  40                  45

Lys Ala Glu Ala Thr Arg Leu Glu Lys Ile Lys Thr Asp Arg Lys Lys
     50                  55                  60

Ala Glu Glu Glu Ala Lys Arg Lys Ala Ala Glu Glu Asp Lys Val Lys
 65                  70                  75                  80

Glu Lys Pro

<210> SEQ ID NO 10
<211> LENGTH: 249
<212> TYPE: DNA
<213> ORGANISM: Streptococcus pneumoniae
<220> FEATURE:
<221> NAME/KEY: misc_feature
<222> LOCATION: (0)...(0)
<223> OTHER INFORMATION: Nucleotide sequence encoding the R22
      polypeptide set forth in SEQ ID NO:9 corresponding to residues
      361-443 of the CbpA protein from Streptococcus
      pneumoniae Tigr4 strain
<221> NAME/KEY: CDS
<222> LOCATION: (1)...(249)

<400> SEQUENCE: 10 aat act tac aaa acg ctt gaa ctt gaa att gct gag tcc gat gtg gaa      48
Asn Thr Tyr Lys Thr Leu Glu Leu Glu Ile Ala Glu Ser Asp Val Glu
  1               5                  10                  15 gtt aaa aaa gcg gag ctt gaa cta gta aaa gag gaa gct aag gaa cct      96
Val Lys Lys Ala Glu Leu Glu Leu Val Lys Glu Glu Ala Lys Glu Pro
             20                  25                  30 cga aac gag gaa aaa gtt aag caa gca aaa gcg gaa gtt gag agt aaa     144
Arg Asn Glu Glu Lys Val Lys Gln Ala Lys Ala Glu Val Glu Ser Lys
         35                  40                  45
```

```
aaa gct gag gct aca agg tta gaa aaa atc aag aca gat cgt aaa aaa      192
Lys Ala Glu Ala Thr Arg Leu Glu Lys Ile Lys Thr Asp Arg Lys Lys
         50                  55                  60 gca gaa gaa gaa gct aaa cga aaa gca gca gaa gaa gat aaa gtt aaa      240
Ala Glu Glu Glu Ala Lys Arg Lys Ala Ala Glu Glu Asp Lys Val Lys
 65                  70                  75                  80 gaa aaa cca                                                          249
Glu Lys Pro <210> SEQ ID NO 11
<211> LENGTH: 6
<212> TYPE: PRT
<213> ORGANISM: Streptococcus pneumoniae

<400> SEQUENCE: 11

Arg Arg Asn Tyr Pro Thr
 1               5

<210> SEQ ID NO 12
<211> LENGTH: 18
<212> TYPE: DNA
<213> ORGANISM: Streptococcus pneumoniae
<220> FEATURE:
<221> NAME/KEY: misc_feature
<222> LOCATION: (0)...(0)
<223> OTHER INFORMATION: Nucleotide sequence encoding the amino acid
      sequence for the putative pIgR binding site of
      CbpA set forth in SEQ ID NO:11
<221> NAME/KEY: CDS
<222> LOCATION: (1)...(18)

<400> SEQUENCE: 12 cgc cgt aac tac cca acc                                               18
Arg Arg Asn Tyr Pro Thr
 1               5

<210> SEQ ID NO 13
<211> LENGTH: 7
<212> TYPE: PRT
<213> ORGANISM: Streptococcus pneumoniae

<400> SEQUENCE: 13

Glu Pro Arg Asn Glu Glu Lys
 1               5

<210> SEQ ID NO 14
<211> LENGTH: 21
<212> TYPE: DNA
<213> ORGANISM: Streptococcus pneumoniae
<220> FEATURE:
<221> NAME/KEY: misc_feature
<222> LOCATION: (0)...(0)
<223> OTHER INFORMATION: Nucleotide sequence encoding the amino acid
      sequence for the putative laminin receptor binding
      site of CbpA set forth in SEQ ID NO:13
<221> NAME/KEY: CDS
<222> LOCATION: (1)...(21)

<400> SEQUENCE: 14 gaa cct cga aac gag gaa aaa                                           21
Glu Pro Arg Asn Glu Glu Lys
 1               5

<210> SEQ ID NO 15
<211> LENGTH: 62
<212> TYPE: PRT
<213> ORGANISM: Artificial Sequence
<220> FEATURE:
<223> OTHER INFORMATION: Amino acid sequence for the CbpA-mR21/Cys
```

-continued

```
      polypeptide construct

<400> SEQUENCE: 15

Pro Glu Lys Lys Cys Ala Glu Ala Glu Lys Val Glu Glu Ala Lys
1               5                  10                  15

Lys Lys Ala Glu Asp Gln Lys Glu Glu Asp Arg Arg Asn Tyr Pro Thr
            20                  25                  30

Asn Thr Tyr Lys Thr Leu Glu Leu Glu Ile Ala Glu Ser Asp Val Glu
        35                  40                  45

Val Lys Lys Ala Glu Leu Glu Leu Cys Lys Glu Glu Ala Lys
    50                  55                  60

<210> SEQ ID NO 16
<211> LENGTH: 192
<212> TYPE: DNA
<213> ORGANISM: Artificial Sequence
<220> FEATURE:
<223> OTHER INFORMATION: Nucleotide sequence encoding the CbpA-mR21/Cys
      polypeptide construct set forth in SEQ ID NO:15

<400> SEQUENCE: 16
atgccagaaa aaagtgtgc agaagctgag aagaaggttg aagaagctaa gaaaaaagcc    60
gaggatcaaa agaagaaga tcgccgtaac tacccaacca atacttacaa aacgcttgaa   120
cttgaaattg ctgagtccga tgtggaagtt aaaaaagcgg agcttgaact agtatgtgag   180
gaagctaagg aa                                                      192

<210> SEQ ID NO 17
<211> LENGTH: 83
<212> TYPE: PRT
<213> ORGANISM: Artificial Sequence
<220> FEATURE:
<223> OTHER INFORMATION: Amino acid sequence for the CbpA-mR22/Cys
      polypeptide construct

<400> SEQUENCE: 17

Asn Thr Tyr Cys Thr Leu Glu Leu Glu Ile Ala Glu Ser Asp Val Glu
1               5                  10                  15

Val Lys Lys Ala Glu Leu Glu Leu Val Lys Glu Glu Ala Lys Glu Pro
            20                  25                  30

Arg Asn Glu Glu Lys Val Lys Gln Ala Lys Ala Glu Val Glu Ser Lys
        35                  40                  45

Lys Ala Glu Ala Thr Arg Leu Glu Lys Ile Lys Thr Asp Arg Lys Lys
    50                  55                  60

Ala Glu Glu Glu Ala Lys Arg Lys Ala Ala Glu Glu Asp Lys Cys Lys
65                  70                  75                  80

Glu Lys Pro

<210> SEQ ID NO 18
<211> LENGTH: 252
<212> TYPE: DNA
<213> ORGANISM: Artificial Sequence
<220> FEATURE:
<223> OTHER INFORMATION: Nucleotide sequence encoding the CbpA-mR22/Cys
      polypeptide construct set forth in SEQ ID NO:17

<400> SEQUENCE: 18
atgaatactt actgtacgct tgaacttgaa attgctgagt ccgatgtgga agttaaaaaa    60
gcggagcttg aactagtaaa agaggaagct aaggaacctc gaaacgagga aaaagttaag   120
caagcaaaag cggaagttga gagtaaaaaa gctgaggcta caaggttaga aaaaatcaag   180
```

```
acagatcgta aaaaagcaga agaagaagct aaacgaaaag cagcagaaga agataaatgt    240
aaagaaaaac ca                                                        252
```

```
<210> SEQ ID NO 19
<211> LENGTH: 30
<212> TYPE: PRT
<213> ORGANISM: Streptococcus pneumoniae
<220> FEATURE:
<221> NAME/KEY: PEPTIDE
<222> LOCATION: (1)...(30)
<223> OTHER INFORMATION: Amino acid sequence for the NYPTs polypeptide
      construct

<400> SEQUENCE: 19
```

```
Ala Lys Lys Lys Ala Glu Asp Gln Lys Glu Glu Asp Arg Arg Asn Tyr
 1               5                  10                  15

Pro Thr Asn Thr Tyr Lys Thr Leu Glu Leu Glu Ile Ala Glu
            20                  25                  30
```

```
<210> SEQ ID NO 20
<211> LENGTH: 90
<212> TYPE: DNA
<213> ORGANISM: Streptococcus pneumoniae
<220> FEATURE:
<221> NAME/KEY: misc_feature
<222> LOCATION: (0)...(0)
<223> OTHER INFORMATION: Nucleotide sequence encoding the NYPTs
      polypeptide construct set forth in SEQ ID NO:19
<221> NAME/KEY: CDS
<222> LOCATION: (1)...(90)

<400> SEQUENCE: 20
```

```
gct aag aaa aaa gcc gag gat caa aaa gaa gaa gat cgc cgt aac tac    48
Ala Lys Lys Lys Ala Glu Asp Gln Lys Glu Glu Asp Arg Arg Asn Tyr
 1               5                  10                  15 cca acc aat act tac aaa acg ctt gaa ctt gaa att gct gag            90
Pro Thr Asn Thr Tyr Lys Thr Leu Glu Leu Glu Ile Ala Glu
            20                  25                  30
```

```
<210> SEQ ID NO 21
<211> LENGTH: 30
<212> TYPE: PRT
<213> ORGANISM: Artificial Sequence
<220> FEATURE:
<223> OTHER INFORMATION: Amino acid sequence for the NYPTsCys
      polypeptide construct

<400> SEQUENCE: 21
```

```
Ala Cys Lys Lys Ala Glu Asp Gln Lys Glu Glu Asp Arg Arg Asn Tyr
 1               5                  10                  15

Pro Thr Asn Thr Tyr Lys Thr Leu Glu Leu Glu Cys Ala Glu
            20                  25                  30
```

```
<210> SEQ ID NO 22
<211> LENGTH: 90
<212> TYPE: DNA
<213> ORGANISM: Artificial Sequence
<220> FEATURE:
<223> OTHER INFORMATION: Nucleotide sequence encoding the NYPTsCys
      polypeptide construct set forth in SEQ ID NO:21

<400> SEQUENCE: 22
```

```
gcttgtaaaa aagccgagga tcaaaaagaa gaagatcgcc gtaactaccc aaccaatact    60
tacaaaacgc ttgaacttga atgtgctgag                                     90
```

```
<210> SEQ ID NO 23
```

```
<211> LENGTH: 46
<212> TYPE: PRT
<213> ORGANISM: Streptococcus pneumoniae
<220> FEATURE:
<221> NAME/KEY: PEPTIDE
<222> LOCATION: (1)...(46)
<223> OTHER INFORMATION: Amino acid sequence for the NYPT1 polypeptide
      construct

<400> SEQUENCE: 23

Gly Glu Lys Lys Val Ala Glu Ala Lys Lys Ala Glu Asp Gln Lys
 1               5                  10                  15

Glu Glu Asp Arg Arg Asn Tyr Pro Thr Asn Thr Tyr Lys Thr Leu Glu
            20                  25                  30

Leu Glu Ile Ala Glu Ser Asp Val Glu Val Lys Lys Ala Glu
         35                  40                  45

<210> SEQ ID NO 24
<211> LENGTH: 159
<212> TYPE: DNA
<213> ORGANISM: Streptococcus pneumoniae
<220> FEATURE:
<221> NAME/KEY: misc_feature
<222> LOCATION: (0)...(0)
<223> OTHER INFORMATION: Nucleotide sequence encoding the NYPT1
      polypeptide construct set forth in SEQ ID NO:23
<221> NAME/KEY: CDS
<222> LOCATION: (1)...(159)

<400> SEQUENCE: 24 ggg gaa aaa aag gta gca gaa gct gag aag aag gtt gaa gaa gct aag      48
Gly Glu Lys Lys Val Ala Glu Ala Glu Lys Lys Val Glu Glu Ala Lys
 1               5                  10                  15 aaa aaa gcc gag gat caa aaa gaa gaa gat cgc cgt aac tac cca acc      96
Lys Lys Ala Glu Asp Gln Lys Glu Glu Asp Arg Arg Asn Tyr Pro Thr
            20                  25                  30 aat act tac aaa acg ctt gaa ctt gaa att gct gag tcc gat gtg gaa     144
Asn Thr Tyr Lys Thr Leu Glu Leu Glu Ile Ala Glu Ser Asp Val Glu
         35                  40                  45 gtt aaa aaa gcg gag                                                  159
Val Lys Lys Ala Glu
     50

<210> SEQ ID NO 25
<211> LENGTH: 45
<212> TYPE: PRT
<213> ORGANISM: Artificial Sequence
<220> FEATURE:
<223> OTHER INFORMATION: Amino acid sequence for the NYPT1Cys
      polypeptide construct

<400> SEQUENCE: 25

Glu Lys Lys Val Ala Glu Ala Cys Lys Lys Ala Glu Asp Gln Lys Glu
 1               5                  10                  15

Glu Asp Arg Arg Asn Tyr Pro Thr Asn Thr Tyr Lys Thr Leu Glu Leu
            20                  25                  30

Glu Cys Ala Glu Ser Asp Val Glu Val Lys Lys Ala Glu
         35                  40                  45

<210> SEQ ID NO 26
<211> LENGTH: 159
<212> TYPE: DNA
<213> ORGANISM: Artificial Sequence
<220> FEATURE:
<223> OTHER INFORMATION: Nucleotide sequence encoding the NYPT1Cys
      polypeptide construct set forth in SEQ ID NO:25
```

```
<400> SEQUENCE: 26
ggggaaaaaa aggtagcaga atgtgagaag aaggttgaag aagctaagaa aaaagccgag      60
gatcaaaaag aagaagatcg ccgtaactac ccaaccaata cttacaaaac gcttgaactt     120
gaatgtgctg agtccgatgt ggaagttaaa aaagcggag                            159

<210> SEQ ID NO 27
<211> LENGTH: 30
<212> TYPE: PRT
<213> ORGANISM: Streptococcus pneumoniae
<220> FEATURE:
<221> NAME/KEY: PEPTIDE
<222> LOCATION: (1)...(30)
<223> OTHER INFORMATION: Amino acid sequence for the NEEKs polypeptide
      construct

<400> SEQUENCE: 27

Lys Ala Glu Leu Glu Leu Val Lys Glu Glu Ala Lys Glu Pro Arg Asn
1               5                   10                  15

Glu Glu Lys Val Lys Gln Ala Lys Ala Glu Val Glu Ser Lys
            20                  25                  30

<210> SEQ ID NO 28
<211> LENGTH: 90
<212> TYPE: DNA
<213> ORGANISM: Streptococcus pneumoniae
<220> FEATURE:
<221> NAME/KEY: misc_feature
<222> LOCATION: (0)...(0)
<223> OTHER INFORMATION: Nucleotide sequence encoding the NEEKs
      polypeptide construct set forth in SEQ ID NO:27
<221> NAME/KEY: CDS
<222> LOCATION: (1)...(90)

<400> SEQUENCE: 28 aaa gcg gag ctt gaa cta gta aaa gag gaa gct aag gaa cct cga aac       48
Lys Ala Glu Leu Glu Leu Val Lys Glu Glu Ala Lys Glu Pro Arg Asn
1               5                   10                  15 gag gaa aaa gtt aag caa gca aaa gcg gaa gtt gag agt aaa              90
Glu Glu Lys Val Lys Gln Ala Lys Ala Glu Val Glu Ser Lys
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Amino acid sequence for the NEEKsCys
      polypeptide construct

<400> SEQUENCE: 29

Lys Cys Glu Leu Glu Leu Val Lys Glu Glu Ala Lys Glu Pro Arg Asn
1               5                   10                  15

Glu Glu Lys Val Lys Gln Ala Lys Ala Glu Cys Glu Ser Lys
            20                  25                  30

<210> SEQ ID NO 30
<211> LENGTH: 90
<212> TYPE: DNA
<213> ORGANISM: Artificial Sequence
<220> FEATURE:
<223> OTHER INFORMATION: Nucleotide sequence encoding the NEEKsCys
      polypeptide construct set forth in SEQ ID NO:29

<400> SEQUENCE: 30
aaatgtgagc ttgaactagt aaaagaggaa gctaaggaac ctcgaaacga ggaaaaagtt      60
```

```
aagcaagcaa aagcggaatg tgagagtaaa                                          90
```

```
<210> SEQ ID NO 31
<211> LENGTH: 46
<212> TYPE: PRT
<213> ORGANISM: Streptococcus pneumoniae
<220> FEATURE:
<221> NAME/KEY: PEPTIDE
<222> LOCATION: (1)...(46)
<223> OTHER INFORMATION: Amino acid sequence for the NEEK1 polypeptide
      construct

<400> SEQUENCE: 31

Gly Glu Ser Asp Val Glu Val Lys Lys Ala Glu Leu Glu Leu Val Lys
 1               5                  10                  15

Glu Glu Ala Lys Glu Pro Arg Asn Glu Glu Lys Val Lys Gln Ala Lys
            20                  25                  30

Ala Glu Val Glu Ser Lys Lys Ala Glu Ala Thr Arg Leu Glu
        35                  40                  45

<210> SEQ ID NO 32
<211> LENGTH: 135
<212> TYPE: DNA
<213> ORGANISM: Streptococcus pneumoniae
<220> FEATURE:
<221> NAME/KEY: misc_feature
<222> LOCATION: (0)...(0)
<223> OTHER INFORMATION: Nucleotide sequence encoding the NEEK1
      polypeptide construct set forth in SEQ ID NO:31
<221> NAME/KEY: CDS
<222> LOCATION: (1)...(135)

<400> SEQUENCE: 32 gag tcc gat gtg gaa gtt aaa aaa gcg gag ctt gaa cta gta aaa gag    48
Glu Ser Asp Val Glu Val Lys Lys Ala Glu Leu Glu Leu Val Lys Glu
 1               5                  10                  15 gaa gct aag gaa cct cga aac gag gaa aaa gtt aag caa gca aaa gcg    96
Glu Ala Lys Glu Pro Arg Asn Glu Glu Lys Val Lys Gln Ala Lys Ala
            20                  25                  30 gaa gtt gag agt aaa aaa gct gag gct aca agg tta gaa               135
Glu Val Glu Ser Lys Lys Ala Glu Ala Thr Arg Leu Glu
        35                  40                  45

<210> SEQ ID NO 33
<211> LENGTH: 45
<212> TYPE: PRT
<213> ORGANISM: Artificial Sequence
<220> FEATURE:
<223> OTHER INFORMATION: Amino acid sequence for the NEEK1Cys
      polypeptide construct

<400> SEQUENCE: 33

Glu Ser Asp Val Glu Val Lys Cys Ala Glu Leu Glu Leu Val Lys Glu
 1               5                  10                  15

Glu Ala Lys Glu Pro Arg Asn Glu Glu Lys Val Lys Gln Ala Lys Ala
            20                  25                  30

Glu Cys Glu Ser Lys Lys Ala Glu Ala Thr Arg Leu Glu
        35                  40                  45

<210> SEQ ID NO 34
<211> LENGTH: 138
<212> TYPE: DNA
<213> ORGANISM: Artificial Sequence
<220> FEATURE:
<223> OTHER INFORMATION: Nucleotide sequence encoding the NEEK1Cys
      polypeptide construct set forth in SEQ ID NO:33
```

<400> SEQUENCE: 34

```
ggggagtccg atgtggaagt taaatgtgcg gagcttgaac tagtaaaaga ggaagctaag    60
gaacctcgaa acgaggaaaa agttaagcaa gcaaaagcgg aatgtgagag taaaaaagct   120
gaggctacaa ggttagaa                                                 138
```

<210> SEQ ID NO 35
<211> LENGTH: 30
<212> TYPE: PRT
<213> ORGANISM: Streptococcus pneumoniae
<220> FEATURE:
<221> NAME/KEY: PEPTIDE
<222> LOCATION: (1)...(30)
<223> OTHER INFORMATION: Amino acid sequence for the NEEKnterm
      polypeptide construct

<400> SEQUENCE: 35

```
Leu Glu Ile Ala Glu Ser Asp Val Glu Val Lys Lys Ala Glu Leu Glu
 1               5                  10                  15

Leu Val Lys Glu Glu Ala Lys Glu Pro Arg Asn Glu Glu Lys
            20                  25                  30
```

<210> SEQ ID NO 36
<211> LENGTH: 90
<212> TYPE: DNA
<213> ORGANISM: Streptococcus pneumoniae
<220> FEATURE:
<221> NAME/KEY: misc_feature
<222> LOCATION: (0)...(0)
<223> OTHER INFORMATION: Nucleotide sequence encoding the NEEKnterm
      polypeptide construct set forth in SEQ ID NO:35
<221> NAME/KEY: CDS
<222> LOCATION: (1)...(90)

<400> SEQUENCE: 36

```
ctt gaa att gct gag tcc gat gtg gaa gtt aaa aaa gcg gag ctt gaa     48
Leu Glu Ile Ala Glu Ser Asp Val Glu Val Lys Lys Ala Glu Leu Glu
 1               5                  10                  15 cta gta aaa gag gaa gct aag gaa cct cga aac gag gaa aaa             90
Leu Val Lys Glu Glu Ala Lys Glu Pro Arg Asn Glu Glu Lys
            20                  25                  30
```

<210> SEQ ID NO 37
<211> LENGTH: 30
<212> TYPE: PRT
<213> ORGANISM: Streptococcus pneumoniae
<220> FEATURE:
<221> NAME/KEY: PEPTIDE
<222> LOCATION: (1)...(30)
<223> OTHER INFORMATION: Amino acid sequence for the NEEKcterm
      polypeptide construct

<400> SEQUENCE: 37

```
Glu Pro Arg Asn Glu Glu Lys Val Lys Gln Ala Lys Ala Glu Val Glu
 1               5                  10                  15

Ser Lys Lys Ala Glu Ala Thr Arg Leu Glu Lys Ile Lys Thr
            20                  25                  30
```

<210> SEQ ID NO 38
<211> LENGTH: 90
<212> TYPE: DNA
<213> ORGANISM: Streptococcus pneumoniae
<220> FEATURE:
<221> NAME/KEY: misc_feature
<222> LOCATION: (0)...(0)
<223> OTHER INFORMATION: Nucleotide sequence encoding the NEEKcterm
      polypeptide construct set forth in SEQ ID NO:37
<221> NAME/KEY: CDS

<222> LOCATION: (1)...(90)

<400> SEQUENCE: 38

```
gaa cct cga aac gag gaa aaa gtt aag caa gca aaa gcg gaa gtt gag      48
Glu Pro Arg Asn Glu Glu Lys Val Lys Gln Ala Lys Ala Glu Val Glu
1               5                   10                  15 agt aaa aaa gct gag gct aca agg tta gaa aaa atc aag aca              90
Ser Lys Lys Ala Glu Ala Thr Arg Leu Glu Lys Ile Lys Thr
            20                  25                  30
```

<210> SEQ ID NO 39
<211> LENGTH: 30
<212> TYPE: PRT
<213> ORGANISM: Streptococcus pneumoniae
<220> FEATURE:
<221> NAME/KEY: PEPTIDE
<222> LOCATION: (1)...(30)
<223> OTHER INFORMATION: Amino acid sequence for the R2cterm polypeptide construct

<400> SEQUENCE: 39

```
Arg Leu Glu Lys Ile Lys Thr Asp Arg Lys Lys Ala Glu Glu Glu Ala
1               5                   10                  15

Lys Arg Lys Ala Ala Glu Glu Asp Lys Val Lys Glu Lys Pro
            20                  25                  30
```

<210> SEQ ID NO 40
<211> LENGTH: 90
<212> TYPE: DNA
<213> ORGANISM: Streptococcus pneumoniae
<220> FEATURE:
<221> NAME/KEY: misc_feature
<222> LOCATION: (0)...(0)
<223> OTHER INFORMATION: Nucleotide sequence encoding the R2cterm polypeptide construct set forth in SEQ ID NO:39
<221> NAME/KEY: CDS
<222> LOCATION: (1)...(90)

<400> SEQUENCE: 40

```
agg tta gaa aaa atc aag aca gat cgt aaa aaa gca gaa gaa gaa gct      48
Arg Leu Glu Lys Ile Lys Thr Asp Arg Lys Lys Ala Glu Glu Glu Ala
1               5                   10                  15 aaa cga aaa gca gca gaa gaa gat aaa gtt aaa gaa aaa cca              90
Lys Arg Lys Ala Ala Glu Glu Asp Lys Val Lys Glu Lys Pro
            20                  25                  30
```

<210> SEQ ID NO 41
<211> LENGTH: 45
<212> TYPE: PRT
<213> ORGANISM: Artificial Sequence
<220> FEATURE:
<223> OTHER INFORMATION: Amino acid sequence for the TCENYPTsCys polypeptide construct

<400> SEQUENCE: 41

```
Gln Tyr Ile Lys Ala Asn Ser Lys Phe Ile Gly Ile Thr Gly Gly Ala
1               5                   10                  15

Cys Lys Lys Ala Glu Asp Gln Lys Glu Glu Asp Arg Arg Asn Tyr Pro
            20                  25                  30

Thr Asn Thr Tyr Lys Thr Leu Glu Leu Glu Cys Ala Glu
        35                  40                  45
```

<210> SEQ ID NO 42
<211> LENGTH: 135
<212> TYPE: DNA
<213> ORGANISM: Artificial Sequence
<220> FEATURE:

```
<223> OTHER INFORMATION: Nucleotide sequence encoding the TCENYPTsCys
      polypeptide construct set forth in SEQ ID NO:41

<400> SEQUENCE: 42
cagtatataa aagcgaattc taaattcatc gggatcacgg gcggggcttg taaaaaagcc      60
gaggatcaaa aagaagaaga tcgccgtaac tacccaacca atacttacaa aacgcttgaa    120
cttgaatgtg ctgag                                                      135

<210> SEQ ID NO 43
<211> LENGTH: 45
<212> TYPE: PRT
<213> ORGANISM: Artificial Sequence
<220> FEATURE:
<223> OTHER INFORMATION: Amino acid sequence for the TCENEEKsCys
      polypeptide construct

<400> SEQUENCE: 43

Gln Tyr Ile Lys Ala Asn Ser Lys Phe Ile Gly Ile Thr Gly Gly Lys
 1               5                  10                  15

Cys Glu Leu Glu Leu Val Lys Glu Glu Ala Lys Glu Pro Arg Asn Glu
             20                  25                  30

Glu Lys Val Lys Gln Ala Lys Ala Glu Cys Glu Ser Lys
         35                  40                  45

<210> SEQ ID NO 44
<211> LENGTH: 135
<212> TYPE: DNA
<213> ORGANISM: Artificial Sequence
<220> FEATURE:
<223> OTHER INFORMATION: Nucleotide sequence encoding the TCENEEKsCys
      polypeptide construct set forth in SEQ ID NO:43

<400> SEQUENCE: 44
cagtatataa aagcgaattc taaattcatc gggatcacgg gcgggaaatg tgagcttgaa      60
ctagtaaaag aggaagctaa ggaacctcga acgaggaaa agttaagca agcaaaagcg      120 gaatgtgaga gtaaa                                                     135

<210> SEQ ID NO 45
<211> LENGTH: 41
<212> TYPE: DNA
<213> ORGANISM: Artificial Sequence
<220> FEATURE:
<223> OTHER INFORMATION: PCR primer for mutagenesis of V333C in the
      CbpA-mR21/Cys polypeptide construct

<400> SEQUENCE: 45
cctgaaacca gaaaaaaagt gtgcagaagc tgagaagaag g                         41

<210> SEQ ID NO 46
<211> LENGTH: 38
<212> TYPE: DNA
<213> ORGANISM: Artificial Sequence
<220> FEATURE:
<223> OTHER INFORMATION: PCR primer for mutagenesis of K386C in the
      CbpA-mR21/Cys polypeptide construct

<400> SEQUENCE: 46
gcggagcttg aactagtatg tgaggaagct aaggaacc                             38

<210> SEQ ID NO 47
<211> LENGTH: 40
<212> TYPE: DNA
<213> ORGANISM: Artificial Sequence
<220> FEATURE:
```

<223> OTHER INFORMATION: PCR primer for mutagenesis of K364C in the
      CbpA-mR22/Cys polypeptide construct

<400> SEQUENCE: 47
catatgaata cttactgcac gcttgaactt gaaattgctg					40

<210> SEQ ID NO 48
<211> LENGTH: 42
<212> TYPE: DNA
<213> ORGANISM: Artificial Sequence
<220> FEATURE:
<223> OTHER INFORMATION: PCR primer for mutagenesis of V439C in the
      CbpA-mR22/Cys polypeptide construct

<400> SEQUENCE: 48
gcagcagaag aagataaatg caaagaaaaa ccataagaat tc					42

<210> SEQ ID NO 49
<211> LENGTH: 15
<212> TYPE: PRT
<213> ORGANISM: Artificial Sequence
<220> FEATURE:
<223> OTHER INFORMATION: Amino acid sequence for the minimal functional
      T-cell epitope further comprising a
      glycine-glycine linker

<400> SEQUENCE: 49

Gln Tyr Ile Lys Ala Asn Ser Lys Phe Ile Gly Ile Thr Gly Gly
1               5                   10                  15

<210> SEQ ID NO 50
<211> LENGTH: 20
<212> TYPE: PRT
<213> ORGANISM: Homo sapiens

<400> SEQUENCE: 50

Ile Pro Cys Asn Asn Lys Gly Ala His Ser Val Gly Leu Met Trp Trp
1               5                   10                  15

Met Leu Ala Arg
            20

<210> SEQ ID NO 51
<211> LENGTH: 20
<212> TYPE: PRT
<213> ORGANISM: Homo sapiens

<400> SEQUENCE: 51

Gln Phe Pro Thr Glu Asp Trp Ser Ala Gln Pro Ala Thr Glu Asp Trp
1               5                   10                  15

Ser Ala Ala Pro
            20

<210> SEQ ID NO 52
<211> LENGTH: 295
<212> TYPE: PRT
<213> ORGANISM: Homo sapiens

<400> SEQUENCE: 52

Met Ser Gly Ala Leu Asp Val Leu Gln Met Lys Glu Glu Asp Val Leu
1               5                   10                  15

Lys Phe Leu Ala Ala Gly Thr His Leu Gly Gly Thr Asn Leu Asp Phe
                20                  25                  30

Gln Met Glu Gln Tyr Ile Tyr Lys Arg Lys Ser Asp Gly Ile Tyr Ile
            35                  40                  45

```
Ile Asn Leu Lys Arg Thr Trp Glu Lys Leu Leu Ala Ala Arg Ala
 50                  55                  60

Ile Val Ala Ile Glu Asn Pro Ala Asp Val Ser Val Ile Ser Ser Arg
 65                  70                  75                  80

Asn Thr Gly Gln Arg Ala Val Leu Lys Phe Ala Ala Thr Gly Ala
                 85                  90                  95

Thr Pro Ile Ala Gly Arg Phe Thr Pro Gly Thr Phe Thr Asn Gln Ile
                100                 105                 110

Gln Ala Ala Phe Arg Glu Pro Arg Leu Leu Val Val Thr Asp Pro Arg
                115                 120                 125

Ala Asp His Gln Pro Leu Thr Glu Ala Ser Tyr Val Asn Leu Pro Thr
            130                 135                 140

Ile Ala Leu Cys Asn Thr Asp Ser Pro Leu Arg Tyr Val Asp Ile Ala
145                 150                 155                 160

Ile Pro Cys Asn Asn Lys Gly Ala His Ser Val Gly Leu Met Trp Trp
                165                 170                 175

Met Leu Ala Arg Glu Val Leu Arg Met Arg Gly Thr Ile Ser Arg Glu
            180                 185                 190

His Pro Trp Glu Val Met Pro Asp Leu Tyr Phe Tyr Arg Asp Pro Glu
        195                 200                 205

Glu Ile Glu Lys Glu Glu Gln Ala Ala Ala Gly Lys Ala Val Thr Lys
    210                 215                 220

Glu Glu Phe Gln Gly Glu Trp Thr Ala Pro Ala Pro Glu Phe Thr Ala
225                 230                 235                 240

Thr Gln Pro Glu Val Ala Asp Trp Ser Glu Gly Val Gln Val Pro Ser
                245                 250                 255

Val Pro Ile Gln Gln Phe Pro Thr Glu Asp Trp Ser Ala Gln Pro Ala
                260                 265                 270

Thr Glu Asp Trp Ser Ala Ala Pro Thr Ala Gln Ala Thr Glu Trp Val
            275                 280                 285

Gly Ala Thr Thr Asp Trp Ser
    290                 295

<210> SEQ ID NO 53
<211> LENGTH: 20
<212> TYPE: PRT
<213> ORGANISM: Artificial Sequence
<220> FEATURE:
<223> OTHER INFORMATION: Scrambled control peptide of amino acid
      residues 161-180 of the laminin receptor (SEQ ID NO:52)

<400> SEQUENCE: 53

Ala Trp Val Gly Cys Leu Met Ser Lys Pro Arg Ile His Trp Asn Met
 1               5                  10                  15

Ala Leu Asn Gly
             20

<210> SEQ ID NO 54
<211> LENGTH: 18
<212> TYPE: PRT
<213> ORGANISM: Artificial Sequence
<220> FEATURE:
<223> OTHER INFORMATION: Scrambled negative control peptide of amino
      acid residues 263-282 of the laminin receptor (SEQ ID
      NO:52)

<400> SEQUENCE: 54

Asp Pro Trp Ala Ser Ala Pro Ser Thr Ala Thr Ala Asp Glu Pro Trp
 1               5                  10                  15
```

Ala Thr

<210> SEQ ID NO 55
<211> LENGTH: 5
<212> TYPE: PRT
<213> ORGANISM: Artificial Sequence
<220> FEATURE:
<223> OTHER INFORMATION: CbpA R2 protein negative control peptide

<400> SEQUENCE: 55

Leu Ser Glu Ile Lys
1               5

<210> SEQ ID NO 56
<211> LENGTH: 13
<212> TYPE: PRT
<213> ORGANISM: Artificial Sequence
<220> FEATURE:
<223> OTHER INFORMATION: Amino acid sequence for tt830 T cell epitope

<400> SEQUENCE: 56

Gln Tyr Ile Lys Ala Asn Ser Lys Phe Ile Gly Ile Thr
1               5                   10

<210> SEQ ID NO 57
<211> LENGTH: 15
<212> TYPE: PRT
<213> ORGANISM: Artificial Sequence
<220> FEATURE:
<223> OTHER INFORMATION: Amino acid sequence for F421 T cell epitope

<400> SEQUENCE: 57

Pro Val Val Glu Val Asn Gly Val Thr Ile Gln Val Gly Ser Arg
1               5                   10                  15

<210> SEQ ID NO 58
<211> LENGTH: 6
<212> TYPE: PRT
<213> ORGANISM: Artificial Sequence
<220> FEATURE:
<223> OTHER INFORMATION: Palindromic peptide sequence within residues
      161-180 of the laminin receptor (SEQ ID NO:52)

<400> SEQUENCE: 58

Leu Met Trp Trp Met Leu
1               5

<210> SEQ ID NO 59
<211> LENGTH: 5
<212> TYPE: PRT
<213> ORGANISM: Artificial Sequence
<220> FEATURE:
<223> OTHER INFORMATION: Laminin receptor binding peptide

<400> SEQUENCE: 59

Tyr Ile Gly Ser Arg
1               5

<210> SEQ ID NO 60
<211> LENGTH: 6
<212> TYPE: PRT
<213> ORGANISM: Artificial Sequence
<220> FEATURE:
<223> OTHER INFORMATION: Laminin receptor binding peptide

<400> SEQUENCE: 60

Leu Gly Thr Ile Pro Gly
1               5

```
<210> SEQ ID NO 61
<211> LENGTH: 6
<212> TYPE: PRT
<213> ORGANISM: Artificial Sequence
<220> FEATURE:
<223> OTHER INFORMATION: Laminin receptor-binding peptide in elastin

<400> SEQUENCE: 61

Val Gly Val Ala Pro Gly
 1               5

<210> SEQ ID NO 62
<211> LENGTH: 5
<212> TYPE: PRT
<213> ORGANISM: Streptococcus pneumoniae

<400> SEQUENCE: 62

Arg Asn Tyr Pro Thr
 1               5

<210> SEQ ID NO 63
<211> LENGTH: 5
<212> TYPE: PRT
<213> ORGANISM: Artificial Sequence
<220> FEATURE:
<223> OTHER INFORMATION: Isogenic mutant substitution for RNYPT sequence
      of S. pneumoniae

<400> SEQUENCE: 63

Arg Asn Gly Pro Thr
 1               5

<210> SEQ ID NO 64
<211> LENGTH: 7
<212> TYPE: PRT
<213> ORGANISM: Streptococcus pneumoniae

<400> SEQUENCE: 64

Glu Pro Arg Asp Glu Gln Lys
 1               5

<210> SEQ ID NO 65
<211> LENGTH: 28
<212> TYPE: PRT
<213> ORGANISM: Artificial Sequence
<220> FEATURE:
<223> OTHER INFORMATION: T cell epitope

<400> SEQUENCE: 65

Gln Tyr Ile Lys Ala Asn Ser Lys Phe Ile Gly Ile Thr Gln Tyr Ile
 1               5                  10                  15

Lys Ala Asn Ser Lys Phe Ile Gly Ile Thr Gly Gly
            20                  25

<210> SEQ ID NO 66
<211> LENGTH: 17
<212> TYPE: PRT
<213> ORGANISM: Artificial Sequence
<220> FEATURE:
<223> OTHER INFORMATION: T cell epitope
```

-continued

```
<400> SEQUENCE: 66

Pro Val Glu Val Asn Gly Val Thr Ile Gln Val Gly Ser Arg Gly
1               5                   10                  15

Gly

<210> SEQ ID NO 67
<211> LENGTH: 45
<212> TYPE: PRT
<213> ORGANISM: Artificial Sequence
<220> FEATURE:
<223> OTHER INFORMATION: CbpA-R21 sequence with incorporated cysteine
      residues and linked T cell epitope

<400> SEQUENCE: 67

Ala Cys Lys Lys Ala Glu Asp Gln Lys Glu Glu Asp Arg Arg Asn Tyr
1               5                   10                  15

Pro Thr Asn Thr Tyr Lys Thr Leu Glu Leu Glu Cys Ala Glu Gly Gly
                20                  25                  30

Gln Tyr Ile Lys Ala Asn Ser Lys Phe Ile Gly Ile Thr
            35                  40                  45

<210> SEQ ID NO 68
<211> LENGTH: 45
<212> TYPE: PRT
<213> ORGANISM: Artificial Sequence
<220> FEATURE:
<223> OTHER INFORMATION: CbpA-R21 sequence with incorporated cysteine
      residues and linked T cell epitope

<400> SEQUENCE: 68

Lys Cys Lys Ala Glu Asp Gln Lys Glu Glu Asp Arg Arg Asn Tyr Pro
1               5                   10                  15

Thr Asn Thr Tyr Lys Thr Leu Glu Leu Glu Cys Ala Gly Gly Pro Val
                20                  25                  30

Val Glu Val Asn Gly Val Thr Ile Gln Val Gly Ser Arg
            35                  40                  45

<210> SEQ ID NO 69
<211> LENGTH: 45
<212> TYPE: PRT
<213> ORGANISM: Artificial Sequence
<220> FEATURE:
<223> OTHER INFORMATION: CbpA-R21 sequence with incorporated cysteine
      residues and linked T cell epitope

<400> SEQUENCE: 69

Gln Tyr Ile Lys Ala Asn Ser Lys Phe Ile Gly Ile Thr Gln Tyr Ile
1               5                   10                  15

Lys Ala Asn Ser Lys Phe Ile Gly Ile Thr Gly Gly Gln Cys Glu Glu
                20                  25                  30

Asp Arg Arg Asn Tyr Pro Thr Asn Thr Tyr Lys Cys Leu
            35                  40                  45

<210> SEQ ID NO 70
<211> LENGTH: 45
<212> TYPE: PRT
<213> ORGANISM: Artificial Sequence
<220> FEATURE:
<223> OTHER INFORMATION: CbpA-R21 sequence with incorporated cysteine
      residues and linked T cell epitope

<400> SEQUENCE: 70

Pro Val Val Glu Val Asn Gly Val Thr Ile Gln Val Gly Ser Arg Gly
1               5                   10                  15
```

Gly Lys Cys Lys Ala Glu Asp Gln Lys Glu Asp Arg Arg Asn Tyr
                20                  25                  30

Pro Thr Asn Thr Tyr Lys Thr Leu Glu Leu Glu Cys Ala
            35                  40                  45

<210> SEQ ID NO 71
<211> LENGTH: 45
<212> TYPE: PRT
<213> ORGANISM: Artificial Sequence
<220> FEATURE:
<223> OTHER INFORMATION: CbpA-R22 sequence with incorporated cysteine
      residues and linked T cell epitope

<400> SEQUENCE: 71

Lys Cys Glu Leu Glu Leu Val Lys Glu Ala Lys Glu Pro Arg Asn
1               5                   10                  15

Glu Glu Lys Val Lys Gln Ala Lys Ala Glu Cys Glu Ser Lys Gly Gly
                20                  25                  30

Gln Tyr Ile Lys Ala Asn Ser Lys Phe Ile Gly Ile Thr
            35                  40                  45

<210> SEQ ID NO 72
<211> LENGTH: 45
<212> TYPE: PRT
<213> ORGANISM: Artificial Sequence
<220> FEATURE:
<223> OTHER INFORMATION: CbpA-R22 sequence with incorporated cysteine
      residues and linked T cell epitope

<400> SEQUENCE: 72

Lys Cys Glu Leu Glu Leu Val Lys Glu Ala Lys Glu Pro Arg Asn
1               5                   10                  15

Glu Glu Lys Val Lys Gln Ala Lys Ala Glu Cys Glu Gly Gly Pro Val
                20                  25                  30

Val Glu Val Asn Gly Val Thr Ile Gln Val Gly Ser Arg
            35                  40                  45

<210> SEQ ID NO 73
<211> LENGTH: 45
<212> TYPE: PRT
<213> ORGANISM: Artificial Sequence
<220> FEATURE:
<223> OTHER INFORMATION: CbpA-R22 sequence with incorporated cysteine
      residues and linked T cell epitope

<400> SEQUENCE: 73

Gln Tyr Ile Lys Ala Asn Ser Lys Phe Ile Gly Ile Thr Gln Tyr Ile
1               5                   10                  15

Lys Ala Asn Ser Lys Phe Ile Gly Ile Thr Gly Gly Lys Glu Cys Ala
                20                  25                  30

Lys Glu Pro Arg Asn Glu Glu Lys Val Lys Gln Cys Lys
            35                  40                  45

<210> SEQ ID NO 74
<211> LENGTH: 45
<212> TYPE: PRT
<213> ORGANISM: Artificial Sequence
<220> FEATURE:
<223> OTHER INFORMATION: CbpA-R22 sequence with incorporated cysteine
      residues and linked T cell epitope

<400> SEQUENCE: 74

Pro Val Val Glu Val Asn Gly Val Thr Ile Gln Val Gly Ser Arg Gly
1               5                   10                  15

```
Gly Lys Cys Glu Leu Glu Leu Val Lys Glu Glu Ala Lys Glu Pro Arg
            20                  25                  30

Asn Glu Glu Lys Val Lys Gln Ala Lys Ala Glu Cys Glu
        35                  40                  45
```

SYNTHETIC *STREPTOCOCCUS PNEUMONIAE* VACCINE

FEDERALLY SPONSORED RESEARCH OR DEVELOPMENT

This invention was made with government support under grant number R01 27913 awarded to Dr. Elaine Tuomanen by the National Institutes of Health/National Institute of Allergies and Infectious Diseases. The government has certain rights in the invention.

FIELD OF THE INVENTION

The present invention relates to the field of vaccines for preventing or treating pneumococcal infection.

BACKGROUND OF THE INVENTION

*Streptococcus pneumoniae* is a gram positive bacterium which is a major cause of invasive infections such as sepsis, meningitis, otitis media and lobar pneumonia (Tuomanen et al. NEJM 322:1280-1284, 1995). Infection by *S. pneumoniae* remains a significant health threat worldwide. Pneumococci bind avidly to cells of the upper and lower respiratory tract and to endothelial cells present in blood vessels. Like most bacteria, adherence of pneumococci to human cells is achieved by presentation of bacterial surface proteins that bind to eukaryotic cell surface proteins (Cundell, D. & Tuomanen, E. (1994) *Microb Pathog* 17:361-374). Pneumococci bind to non-inflamed epithelium, a process that can be viewed as asymptomatic carriage. It has been proposed that the conversion to invasive disease involves the local generation of inflammatory factors which, activating the human cell, change the number and type of receptors available on the human cells (Cundell, D. et al. (1995) *Nature,* 377:435-438). Presented with an opportunity in this new setting, pneumococci appear to take advantage and engage one of these up-regulated receptors. For example, bacteria translocate across cells of the respiratory tract via the polymeric immunoglobulin receptor (pIgR) (Zhang et al. (2000) *Cell* 102:827-837). Alternatively, when the bacteria are in the blood stream, the pneumococcal bacteria bind to endothelial cells, and the bacteria cross the blood vessel endothelium by binding to and transcytosing with the platelet activating factor (PAF) receptor (Cundell et al. (1995) *Nature,* 377:435-438). Within minutes of the appearance of the PAF receptor on activated cells, pneumococci undergo waves of enhanced adherence and invasion. Inhibition of bacterial binding to activated cells, for instance by soluble receptor analogs, or absence of the receptor blocks the progression to disease in animal models (Idan-paan-Heikkila, I. et al. (1997) *J. Infect. Dis.,* 176:704-712; Radin et al. (2005) *Infect. Immun.* 73:7827-7835).

Pneumococci produce a family of proteins tethered to the bacterial surface by non-covalent association to the cell wall teichoic acid or lipoteichoic acid. This family of CBPs (choline binding proteins) is non-covalently bound to phosphorylcholine on the cell wall. CbpA, is a 75 kD surface-exposed choline binding protein that shows a chimeric architecture. There is a unique N-terminal domain, a proline rich region followed by a C-terminal domain comprised of 8 repeated regions responsible for binding to choline. CbpA binds specifically to pIgR on epithelial cells. When CbpA binds an extracellular domain present on pIgR, the pneumococcal bacteria are able to hijack the endocytosis machinery to translocate across nasopharyngeal epithelial cells into the blood stream. Mutants with defects in cbpA showed reduced virulence in the infant rat model for nasopharyngeal colonization and in mouse models of meningitis.

The choline binding domain was fully characterized by Lopez et al. in his studies of the autolytic enzyme (Ronda et al. (1987) *Eur. J. Biochem,* 164:621-624). Other proteins containing this domain include the autolysin of pneumococcus and the protective antigen, pneumococcal surface protein A (PspA) (Ronda, C. et al. (1987) *Eur. J. Biochem.,* 164:621-624 and McDaniel, L. S., et al. (1992) *Microb. Pathog.,* 13:261-269). CbpA shares the C-terminal choline binding domain with its other family members but its activity of binding to human cells arises from its unique N-terminal domain. Since the process of colonization and the progression to disease depend on pneumococcal attachment to human cells as a primary step, interruption of the function of the N terminal domain, either by cross reactive antibody or by competitive inhibition with a peptide mimicking this domain, may be critical to blocking disease.

The N-terminus of CbpA, corresponding to amino acid residues 39-514 of the CbpA protein from the Tigr4 strain, contains numerous repeats of the leucine zipper motif that cluster within 5 domains termed the A, B, R1, R2, and C domains. Domains A, B, and C are predicted to form coiled-coiled dimers. The R1 and R2 are also predicted to form self-associated, coiled-coil structures. The solution structure of CbpA was recently elucidated in Luo et al. (2005) *EMBO J.* 24(1):34-43, which is herein incorporated by reference in its entirety. In particular, the R2 domain of CbpA (amino acid residues approximately 327 to 442) was determined to comprise three anti-parallel alpha-helices. This three alpha-helix structure is similarly predicted for R1 domain, as was recently reported in Jordan et al. (2006) *J. Am. Chem. Soc.* 128(28): 9119-9128.

Notably, the R domains from the Tigr4 strain of *S. pneumoniae* are highly conserved among CbpA sequences from other pneumococcal strains. Therefore, the R domains of CbpA are potentially important targets for the development of vaccines that are protective against numerous pneumococcal strains. Choline binding proteins for anti-pneumococcal vaccines are discussed in U.S. Pat. No. 6,858,706 and PCT International Application No. PCT/US97/07198, both of which are incorporated in their entirety by reference. Current vaccines against *S. pneumoniae* employ purified carbohydrates of the capsules of up to the 23 most common serotypes of this bacterium, but such vaccines are only 50% protective against pneumonia (Shapiro et al. *NJEM* 325:1453, 1991) and are not immunogenic under the age of 2. Conjugate vaccines are based on pneumococcal capsular carbohydrates linked to diphtheria toxoid or tetanus toxoid. Protection against pneumonia, sepsis, or meningitis for these vaccines is limited to the serotypes present in the formulation, thereby leaving patients unprotected against most of the ninety-two serotypes of this bacterium. Further, vaccines that are protective against both the colonization of pneumococcal bacteria in the nasopharynx as well as against entry of pneumococcal bacteria into the bloodstream are needed in the art. Therefore, the invention herein fills a long felt need by providing pharmaceutical compositions (e.g., vaccines) for the prevention and treatment of a wide range of serotypes of pneumococcal infections.

BRIEF SUMMARY OF THE INVENTION

The present invention is directed to compositions and methods for the treatment and prevention of pneumococcal infections. Compositions of the invention include isolated polypeptides comprising amino acid sequences from the R2 domain of the CbpA protein, particularly the $R2_1$ domain (SEQ ID NO:7), the $R2_2$ domain (SEQ ID NO: 9), the $R2_1$ consensus sequence set forth in SEQ ID NO:11, and/or the $R2_2$ consensus sequence set forth in SEQ ID NO:13, or a biologically active variant or fragment thereof. The polypeptides of the invention are stabilized in a desired conformation, particularly a loop conformation (e.g., the conformation of the region as it exists in the native CbpA protein) by the formation of a synthetic linkage. In certain embodiments, the $R2_1$ and $R2_2$ polypeptides of the invention have been engineered to comprise at least a first cysteine residue and a second cysteine residue, where the first and the second cysteine residues form a disulfide bond such that the polypeptide is stabilized in a desired loop conformation. In other aspects of the invention, the $R2_1$ and $R2_2$ polypeptides have been modified to create a synthetic peptide bond between at least a first and a second amino acid residue present within the polypeptide, wherein the synthetic peptide bond stabilizes the polypeptide in the desired conformation. $R2_1$ and $R2_2$ polypeptides that are stabilized in a loop conformation by formation of a synthetic linkage, such as, for example, the incorporation of cysteine residues or the creation of a synthetic peptide bond between amino acids present in the polypeptide, may be referred to as $R2_1$ or $R2_2$ loop polypeptides. The $R2_1$ and $R2_2$ polypeptides of the invention may further comprise an amino acid sequence for a T cell epitope to increase the immunogencity of the resultant polypeptide. Isolated nucleic acid molecules that encode the polypeptides of the invention are further disclosed herein. Compositions also include immunogenic compositions and vaccines comprising at least one $R2_1$ or $R2_2$ loop polypeptide. Antibodies specific for a polypeptide of the invention are further provided. The compositions of the invention find use in methods for preventing and treating pneumococcal infections.

Methods for preventing and treating pneumococcal infections are further provided. These methods comprise administering to a subject a therapeutically effective amount of an immunogenic composition, a vaccine, or a pharmaceutical antibody composition as disclosed herein. Methods are also provided to modulate the entry of compounds and infectious agents of interest across the blood brain barrier.

BRIEF DESCRIPTION OF THE DRAWINGS

FIG. 1-1A provides a schematic representation of the three-dimensional structure of the R2 domain of native choline binding protein A (CbpA), with boxes indicating regions of the protein with defined functions in disease. FIG. 1-2B provides a schematic representation of the R2 domain from the N-terminus of the CbpA protein of the Tigr4 strain of S. pneumoniae, corresponding to amino acid residues 329-443. A schematic representation of an exemplary $R2_1$ cysteine mutant polypeptide of the invention comprising amino acid residues 329-391 of the CbpA protein, wherein the valine at position 333 and the lysine at position 386 have each been engineered to comprise a cysteine residue is further provided (i.e., $mR2_1$/Cys). An exemplary $R2_2$ cysteine mutant polypeptide of the invention comprising amino acid residues 361-443 of the CbpA protein, wherein the lysine at position 364 and the valine at position 439 have each been engineered to comprise a cysteine residue is also presented (i.e., $mR2_2$/Cys).

FIG. 2 provides a summary of the mean IgG titers following intramuscular or intraperitoneal immunization of mice with the polypeptide constructs described in Example 2. Additional experimental details are provided in Example 2.

immunized with recombinant CbpA R2 protein (positive control), LSEIK peptide (SEQ ID NO:55; negative control), the TCENYPTsCys peptide (SEQ ID NO:41; corresponding to the CbpA $R2_1$ domain and an amino acid sequence for a TCE), the TCENEEKsCys peptide (SEQ ID NO:43; corresponding to the CbpA $R2_2$ domain and an amino acid sequence for a TCE), or a combination of the TCENYPTsCys peptide and the TCENEEKsCys peptide. Additional experimental details are provided in Example 6.

Figure 12:
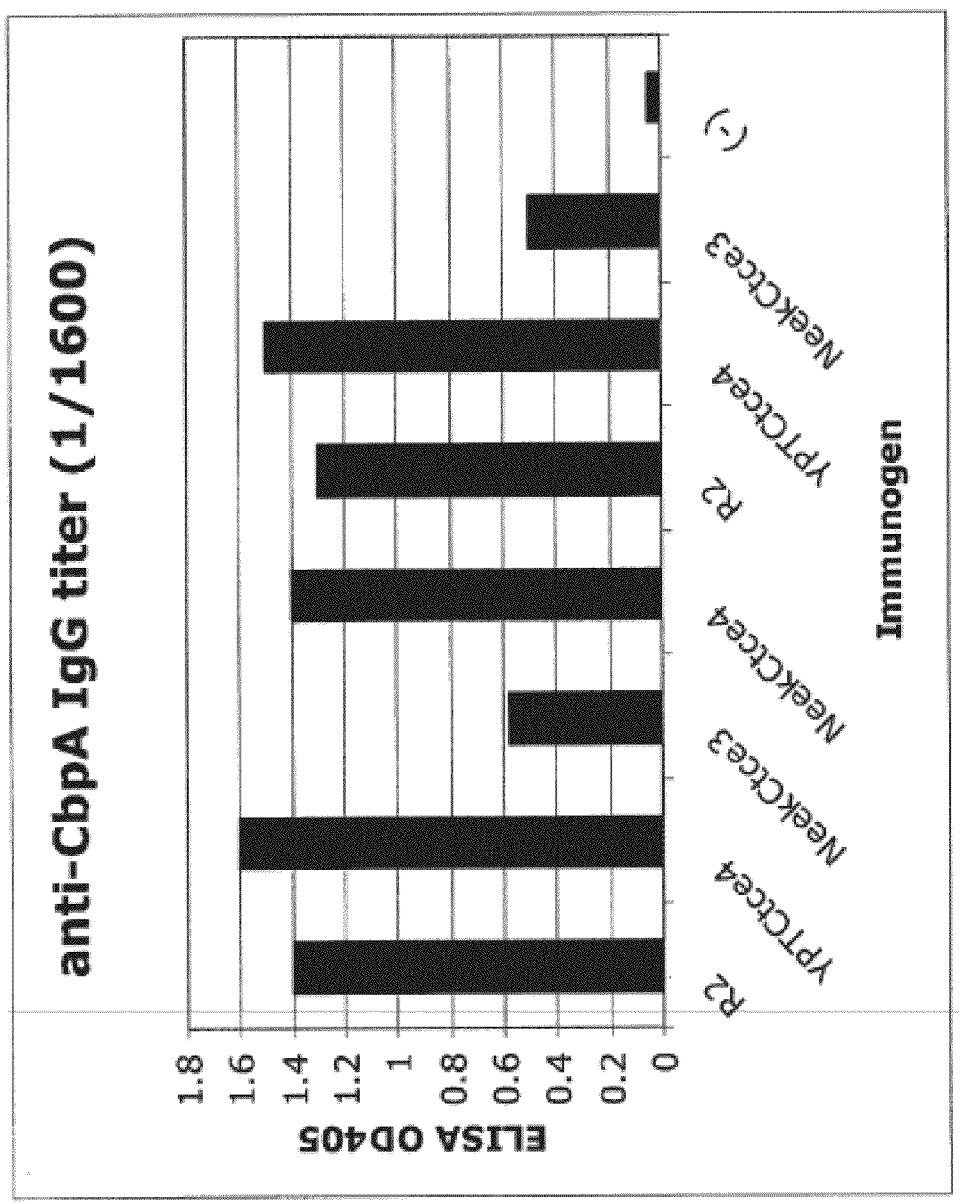

FIG. 12 provides a summary of the anti-CbpA IgG titers of mice immunized with recombinant CbpA R2 protein (positive control), YPTCtce4 peptide (SEQ ID NO:70), the NEEKCtce3 peptide (SEQ ID NO:73), the NEEKCtce4 peptide (SEQ ID NO:74, or a negative control without any peptide. Experimental details are provided in Example 7.

Figure 13:
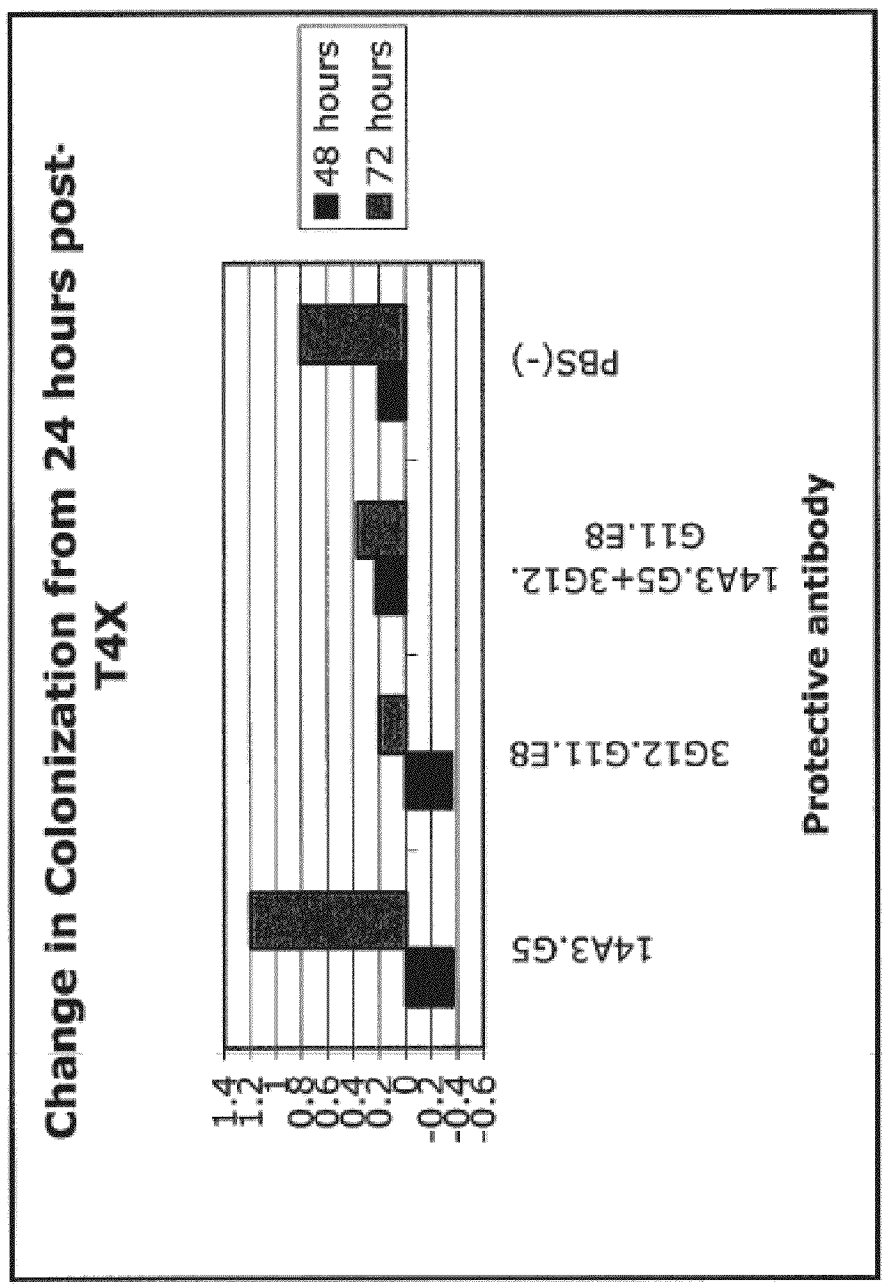

FIG. 13 presents the change in nasopharyngeal colonization observed in passive protection studies following injection of monoclonal antibodies directed to the RNYPT loop (antibody 14A3.G5), the EPRNEEK loop (antibody 3G12.G11.E8), or both antibodies. A PBS injection was used as a negative control. Results at 48 hours and 72 hours post-infection are provided. Experimental details are set forth in Example 8.

Figure 14:
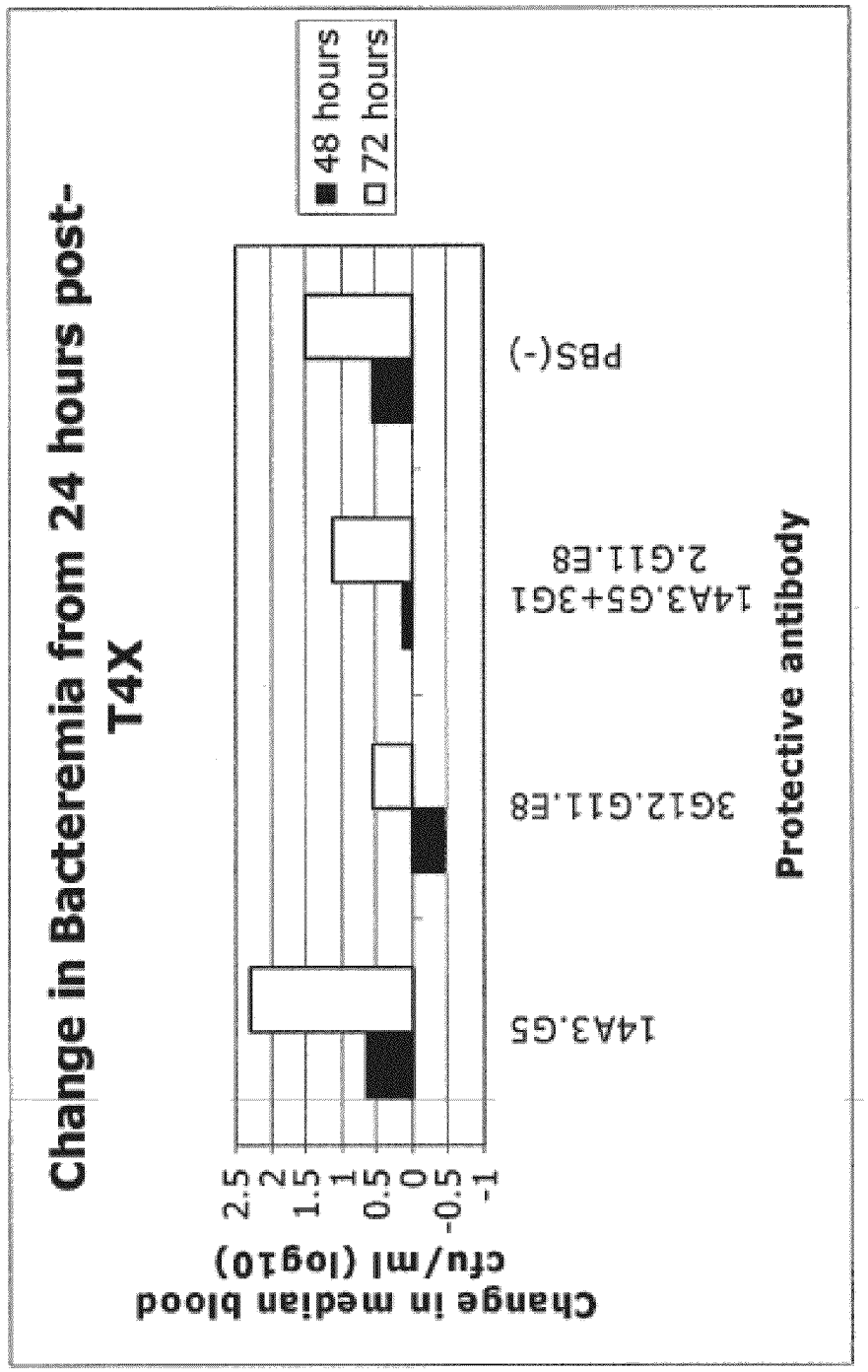

FIG. 14 presents the change in bacteremia observed in passive protection studies following injection of monoclonal antibodies directed to the RNYPT loop (antibody 14A3.G5), the EPRNEEK loop (antibody 3G12.G11.E8), or both antibodies. A PBS injection was used as a negative control. Results at 48 hours and 72 hours post-infection are provided. Experimental details are set forth in Example 8.

Figure 15:
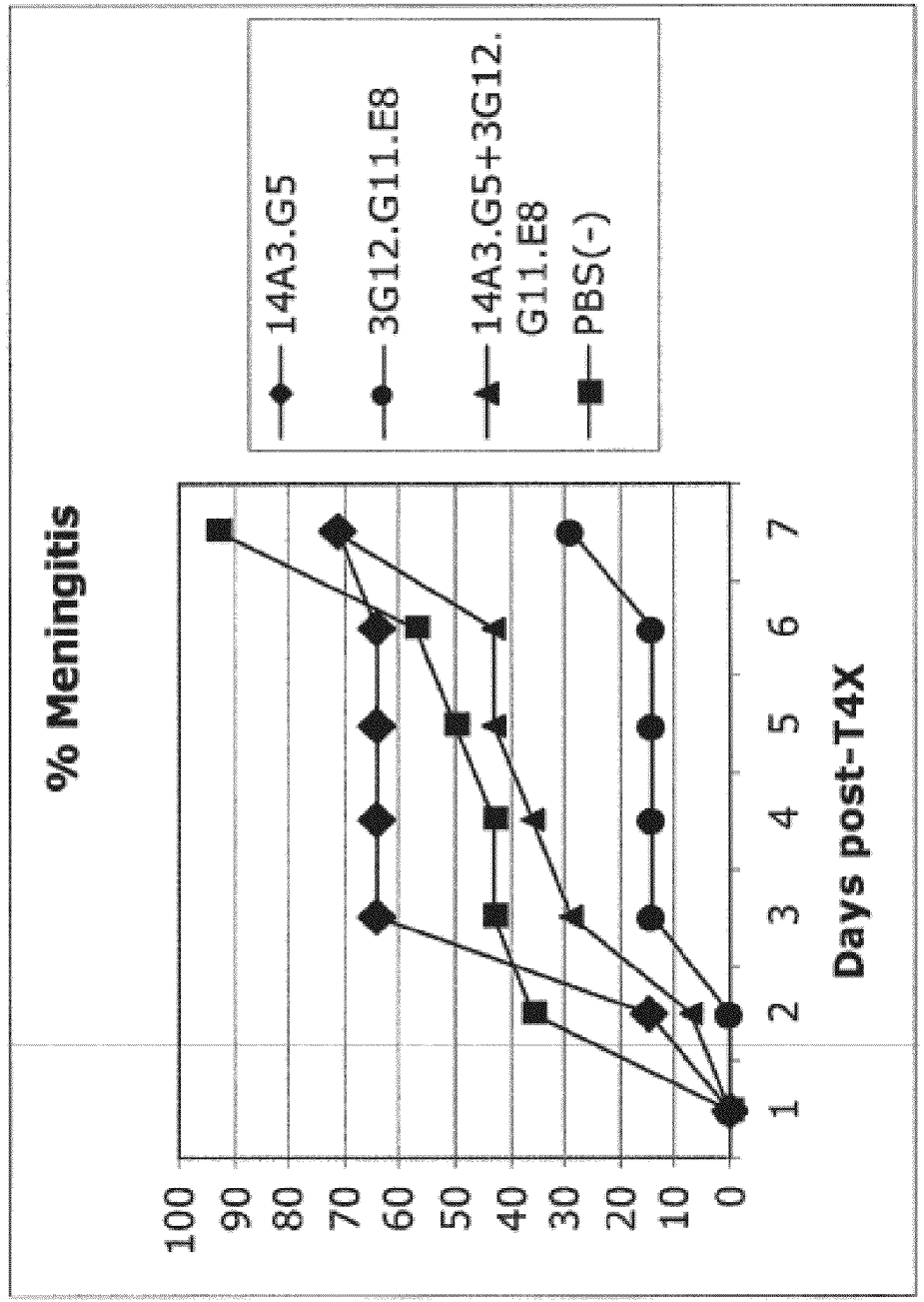

FIG. 15 provides the percentage of mice in each group of the passive protection studies the developed meningitis following injection of monoclonal antibodies directed to the RNYPT loop (antibody 14A3.G5), the EPRNEEK loop (antibody 3G12.G11.E8), or both antibodies. A PBS injection was used as a negative control. Experimental details are set forth in Example 8.

Figure 16:
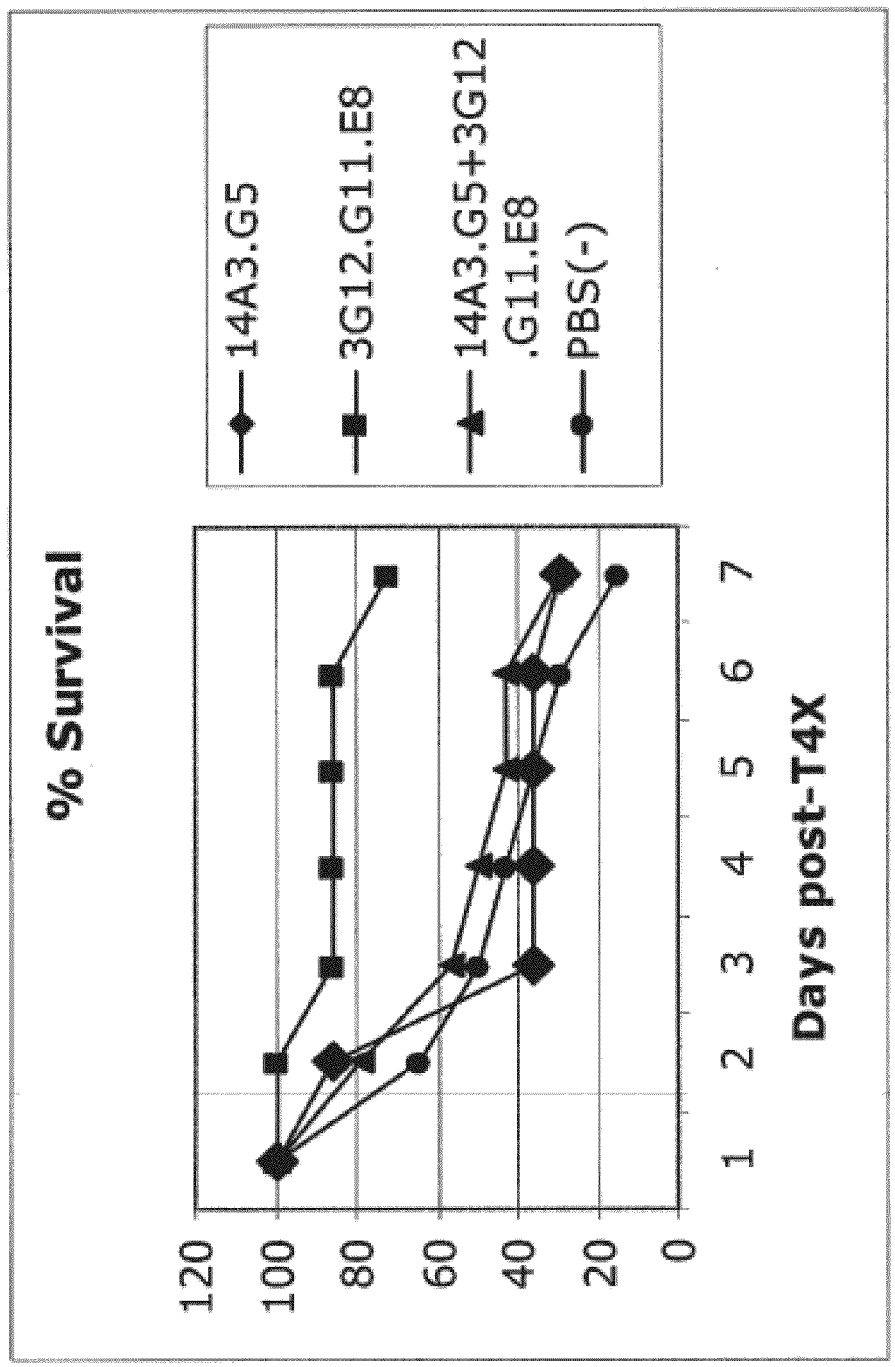

FIG. 16 provides the survival rates for each group of the passive protection studies following injection of monoclonal antibodies directed to the RNYPT loop (antibody 14A3.G5), the EPRNEEK loop (antibody 3G12.G11.E8), or both antibodies. A PBS injection was used as a negative control. Experimental details are set forth in Example 8.

Figure 17:
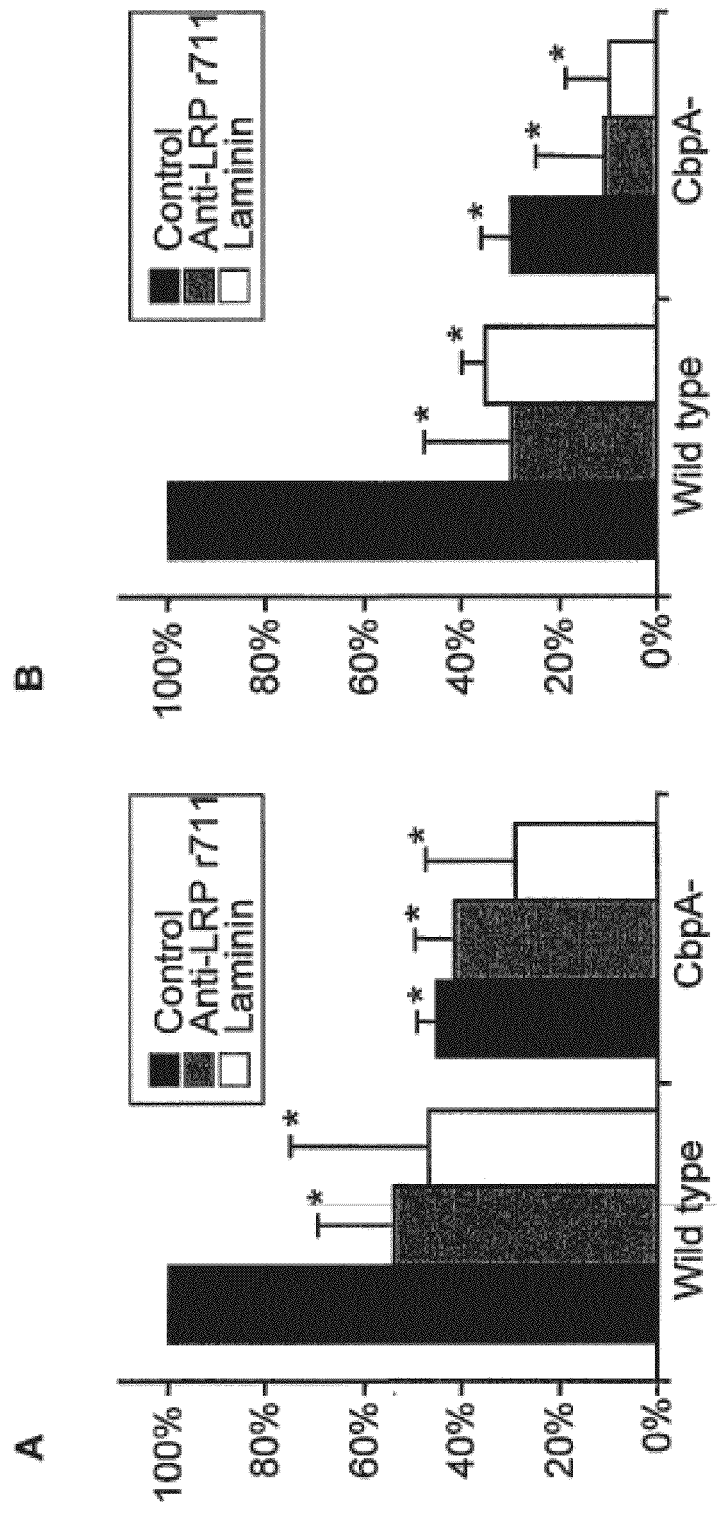

FIG. 17 provides the results of assays performed to assess the ability of wild-type S. pneumoniae T4R and S. pneumoniae T4R CbpA- mutant to adhere to and invade RBCEC6 cells pretreated with a laminin receptor antibody ([71]) or laminin. The laminin receptor antibody and laminin inhibited both adhesion (FIG. 12A) and invasion (FIG. 12B) of wild-type S. pneumoniae T4R. Additional experimental details are provided in Example 6.

Figure 18:
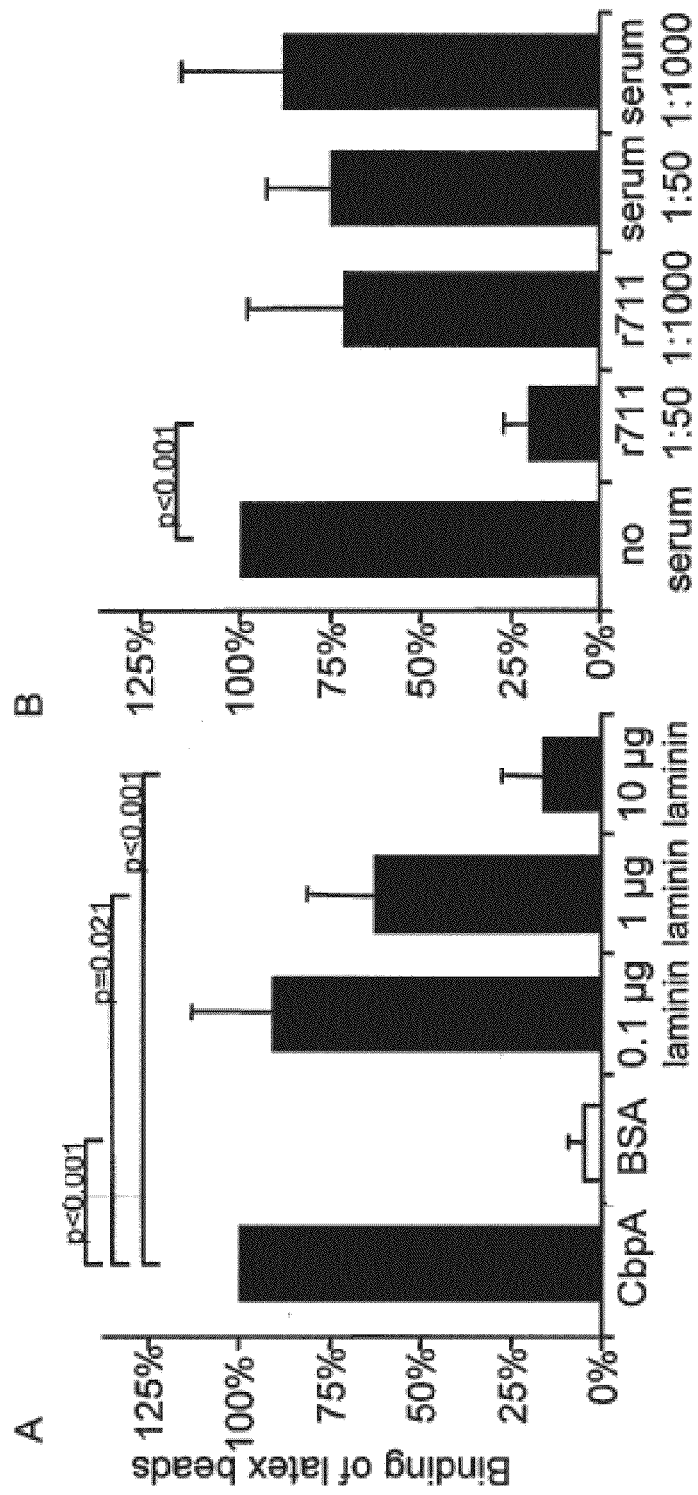

FIG. 18 presents the results of adhesion assays performed to assess the binding of CbpA-labeled latex beads to RBCEC6 cells in the presence of varying concentrations of laminin and a laminin receptor antibody. Adhesion of the CbpA-labeled beads was inhibited by laminin (FIG. 13A) and the laminin receptor antibody (FIG. 13B) in a dose-dependent fashion. Additional experimental details are provided in Example 10.

FIG. 19A provides the results of adhesion assays performed to determine the particular domain of CbpA that is responsible for binding to the laminin receptor. Latex beads were individually labeled with the R1 domain, the R2 domain, the N domain (comprising residues 39-174 of TIGR4CbpA), a combination of the R1 and R2 domain, and a full-length CbpA construct that doesn't bind to pIgR (i.e., pIgR KO). Beads labeled with the R1 domain, the R2 domain, the N domain, and the pIgR KO failed to bind to rBCEC6 cells. Beads labeled with the combined R1 and R2 domain construct, however, adhered to rBCEC6 cells, indicating that CbpA binds to the laminin receptor in a manner that is dependent on the presence of both the R1 and R2 domains. FIG. 19B provides the results of adhesion assays performed in the presence of various carbohydrates. Additional experimental details are provided in Example 10.

Figure 20:
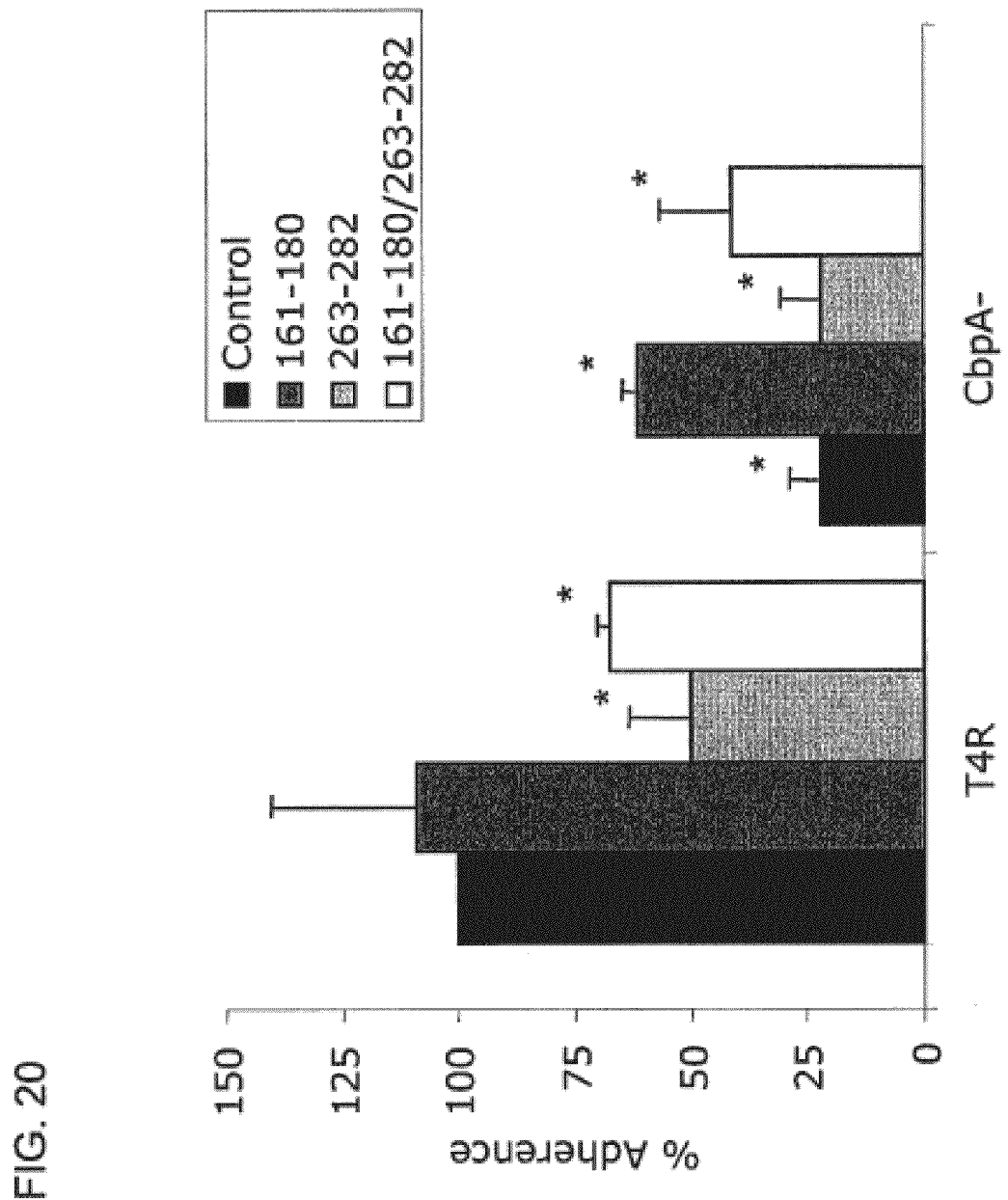

FIG. 20 provides the results of adhesion assays performed to assess the ability of wild-type S. pneumoniae T4R and S. pneumoniae T4R CbpA-mutant to adhere to RBCEC6 cells pretreated with peptides corresponding to amino acids 161-180 (SEQ ID NO:50) and 263-282 (SEQ ID NO:51) of the amino acid sequence for the laminin receptor (SEQ ID NO:52). A scrambled version of residues 161-180 (SEQ ID NO:53) and 263-282 (SEQ ID NO:54) served as controls. The results indicated that the peptide corresponding to 161-180 of the laminin receptor had no effect on bacterial adhesion, whereas incubation with the 263-282 peptide inhibited binding of the wild-type S. pneumoniae to RBCEC6 cells up to 50%. Additional experimental details are provided in Example 10.

FIG. 21 provides non-limiting examples of various fragments of the CbpA polypeptide that can be used to construct an $R2_1$ or $R2_2$ loop polypeptide.

DETAILED DESCRIPTION OF THE INVENTION

The present invention is directed to compositions and methods for the prevention and treatment of pneumococcal infections, more particularly Streptococcus pneumoniae infections. Compositions of the invention include isolated polypeptides comprising amino acid sequences from the R2 domain of the CbpA protein, or a biologically active variant or fragment thereof. The polypeptides of the invention generally comprise an $R2_1$ polypeptide, an $R2_2$ polypeptide, an $R2_1$ consensus sequence polypeptide (SEQ ID NO:11), and/or an $R2_2$ consensus sequence polypeptide (SEQ ID NO:13), or a biologically active variant or fragment thereof, wherein the polypeptide is stabilized in a desired conformation, particularly a loop conformation that resembles the native conformation of these polypeptides within the CbpA protein. Such polypeptides may be referred to as "$R2_1$ or $R2_2$ loop polypeptides" or "loop polypeptides." In particular aspects of the invention, the $R2_1$ or $R2_2$ polypeptides further comprise an amino acid sequence for a T cell epitope (TCE), as described herein below.

Stabilization of the polypeptides of the invention in a desired conformation, such as a loop conformation, may be accomplished by any method known in the art and results from the formation of a "synthetic linkage" in the polypeptide. As used herein, a "synthetic linkage" comprises any covalent or non-covalent interaction that is created in the loop polypeptides of the invention that does not occur in the native protein. Any form of a synthetic linkage that can form a covalent or non-covalent bond, optimally a covalent bond, between amino acids in the native or variant polypeptides can be used in the practice of the invention. Such synthetic linkages can include synthetic peptide bonds that are engineered to occur between amino acids present in either the native polypeptide or a variant thereof. Polypeptides of the invention may comprise any form of synthetic linkage that can result in the formation of a covalent bond between amino acids in the native CbpA protein or variant thereof. A synthetic linkage of the invention further includes any non-covalent interaction that does not occur in the native polypeptide. For example, the loop polypeptides may be engineered to have cysteine residues that are not present in the native CbpA protein and that allow for the formation of a disulfide bridge that stabilizes the polypeptide in a desired conformation.

In one embodiment, a polypeptide of the invention comprises an $R2_1$ or $R2_2$ polypeptide that has been engineered to comprise at least a first cysteine residue and a second cysteine residue, where the first and the second cysteine residues form a disulfide bond such that the polypeptide is stabilized in a desired conformation. The $R2_1$ and $R2_2$ loop polypeptides of the invention engineered to comprise cysteine residues, as described above, may be referred to herein as "$R2_1$ or $R2_2$ cysteine mutant loop polypeptides" or "$R2_1$ or $R2_2$ cysteine mutant polypeptides." In other embodiments, an $R2_1$ or $R2_2$ loop polypeptide of the invention is stabilized in a desired conformation without the incorporation of cysteine residues, e.g., by modifying the polypeptide to create a synthetic linkage (e.g., a synthetic peptide bond) between at least a first and a second amino acid residue present in the polypeptide such that the synthetic linkage stabilizes the polypeptide in the desired conformation.

Synthetic linkages, particularly synthetic peptide bonds, can be formed between at least a first and a second amino acid residue of a polypeptide of the invention in accordance with any method known in the art. In certain embodiments, a synthetic peptide bond is formed between a targeted lysine and glutamic acid residue present in the polypeptide. These residues are first orthogonally-protected, and the resulting derivatives comprise protecting groups, specifically 1-(4,4-dimethyl-2,6-dioxocyclohex-1-ylidene)-3-methylbutyl (also referred to as "ivDde") on the epsilon amine of the lysine and a-4-{N41-(4,4-dimethy1-2,6-dioxocyclohexylidene)-3-methylbutylFamino}benzyl ester (also referred to as "Odmab") on the side-chain carboxy of the glutamic acid residue. After synthesis is completed and before the peptide is cleaved from the resin, these protecting groups are selectively removed using 4-5% hydrazine. The side-chain carboxy of the glutamic acid is converted to an HOAt (1-Hydroxy-7-azabenzotriazole) ester using a non-uronium based activating reagent (i.e., 7-Azabenzotriazol-1-yloxy) tripyrrolidinophosphonium hexafluorophosphate (PyAOP)). The ester then N-acetylates any available amine to produce a peptide bond. Since the epsilon amine on the deprotected ivDde lysine is the only amine available for acetylation, a synthetic peptide bond results from cyclization between the selected residues. After the cyclization is finished, the peptide is cleaved from the resin and purified by standard protocols. See generally Chhabra et al. (1998) *Tetrahedron Lett.* 39:1603-1606; Rohwedder et al. (1998) *Tetrahedron Lett.* 39:1175-1178; Wittmann & Seeberger (2000) *Angew. Chem. Int. Ed. Engl.* 39:4348-4352; and Chan et al. (1995) *J. Chem. Soc., Chem. Commun.* 21:2209-2210, all of which are herein incorporated by reference in their entirety.

Other methods for forming synthetic linkages, particularly synthetic peptide bonds, are known in the art. Such methods include, for example, homobifunctional cross-linking using glutaraldehyde, disuccinimidyl derivatives, water-soluble sulphodisuccinimidyl derivatives, or diimido esters. See Hermanson (1996) *Bioconjugugate Techniques* (Academic Press, San Diego, Calif.); Pfaff et al. (1982) *EMBO J.* 1:869-874; Wood et al. (1985) *J. Biol. Chem.* 260:1243-1247; Tsudo et al. (1987) *Proc. Natl. Acad. Sci. USA* 84:4215-4218; Staros (1982) *Biochem.* 21, 3950-3955; D'Souza et al. (1988) *J. Biol. Chem.* 263:3943-3951; Hartman and Wold (1966) *J. Am. Chem. Soc.* 88:3890-3891; Hartman and Wold (1967) *Biochem.* 6:2439-2448; and O'Keeffe et al. (1980) *Biochemistry* 19:4962-4966, all of which are herein incorporated by reference in their entirety.

Synthetic peptide linkages can also be formed by heterobifunctional cross-linking, as described in, for example, Carlsson et al. (1978) *Biochem. J.* 173:723-737; Bernatowicz and Matsueda (1986) *Anal. Biochem.* 155:95-102; Bematowicz et al. (1986) *Int. J. Pept. Protein Res.* 28:107-112; van Bree et al. (1991) *J. Pharm. Sci.* 80:46-49; and Duncan et al. (1983) *Anal. Biochem.* 132:68-73, all of which are incorporated by reference. Chemo-selective non-amide ligation, including thioalkylation, oxime formation, hydrazone formation, thiazolidine formation, imidazole ligation, and region- and non-regio selective disulfide bond formation, may further be used to form the synthetic linkages of the present invention. See Muir et al. (1994) *Biochemistry* 33:7701-7708; Defoort et al. (1992) *Int. J. Pept. Protein Res.* 40:214-221; Nardelli et al. (1992) *AIDS Res. Hum. Retroviruses* 8:1405-1407; King et al. (1978) *Biochemistry* 17:1499-1506; Kitagawa and Aikawa (1976) *J. Biochem.* (Tokyo) 79:233-236; Erlanger et al. (1957) *J. Biol. Chem.* 228:713-727; Gaertner et al. (1992) *Bioconjug. Chem.* 3:262-268; Gaertner et al. (1994) *J. Biol. Chem.* 269:7224-7230; Gaertner et al. (1994) *Bioconjug. Chem.* 5: 333-338; Liu and Tam (1994) *Proc. Natl. Acad. Sci. USA* 91:6584-6588; Zhang and Tam (1997) *Tetrahedron Lett.* 38:3-6; Barany and Merrifield (1976) in *The peptides—analysis, synthesis, biology* (Gross and Meienhofer, eds.; Academic Press, New York); Fields et al. (1992) in *Synthetic Peptides: a user's guide* (Grant, ed.; W.H. Freeman, New York); Lloyd-Williams et al. (1997) *Chemical approaches to the synthesis of peptides and proteins* (CRC Press, Boca Raton, Fla.); Bullesbach (1992) *Kontakte* (Darmstadt) 1:21; Andreu et al. (1994) in *Methods in molecular biology, Vol. 35: Peptide Synthesis Protocols* (Pennington and Dunn, eds.; Humana Press, Totowa, N.J.); Kiso and Yajima (1995) in *Peptides—synthesis, structures, and applications* (Gutte, ed.; Academic Press, San Diego, Calif.); Moroder et al. (1996) *Biopolymers* 40:207-234; Annis et al. (1997) *Methods in Enzymology* 289:198-221; Brois et al. (1970). *J. Am. Chem. Soc.* 92:7629-7631, all of which are incorporated by reference in their entirety.

As described above, previous research has demonstrated that CbpA binds specifically to pIgR. The amino acid sequence set forth in SEQ ID NO:11 comprises the putative pIgR binding site (i.e., RRNYPT). The present application reports for the first time that CbpA also binds to the laminin receptor. When CbpA binds to the laminin receptor, it facilitates the "hand off" of the bacterium to PAFr which carries the bacterium into the endothelial cell, across the blood vessel wall, out of the blood stream and into the tissues. The amino acid sequence set forth in SEQ ID NO:13 comprises the putative laminin receptor binding domain (i.e., EPRNEEK).

In particular embodiments, the isolated $R2_1$ or $R2_2$ loop polypeptides of the invention comprise the consensus sequence set forth in SEQ ID NO:11 or 13, or a biologically active variant thereof. In other aspects of the invention, the polypeptide comprising SEQ ID NO:11 or 13 has been engineered to comprise at least a first cysteine residue and a second cysteine residue, where the first and the second cysteine residues form a disulfide bond such that the polypeptide is stabilized in a desired conformation. As defined herein, any of the polypeptides of the invention (e.g., SEQ ID NO: 7, 9, 11, or 13, or biologically active variants of fragments thereof) engineered to comprise cysteine residues, as described above, may be referred to herein as a "cysteine mutant loop polypeptide." Various cysteine mutant loop polypeptides are described in further detail below and include, but are not limited to, SEQ ID NO:15, 17, 21, 25, 29, 33, 41, 43, or 67-74. In other aspects of the invention, an $R2_1$ and $R2_2$ loop polypeptide comprises SEQ ID NO:7, 9, 11, or 13, or a biologically active variant of fragment thereof, wherein the polypeptide has been modified to create a synthetic peptide bond between at least a first and a second amino acid residue present in the polypeptide such that the synthetic peptide bond stabilizes the polypeptide in a desired conformation, more particularly a loop conformation. In further embodiments, the $R2_1$ or $R2_2$ loop polypeptides of the invention, particularly the $R2_1$ and $R2_2$ cysteine mutant loop polypeptides, further comprise an amino acid sequence for a T cell epitope. See, for example, the polypeptides set forth in SEQ ID NOs:41, 43, and 67-74. Exemplary polypeptides of the invention are provided in Example 4.

While not intending to be limited to a particular mechanism, it is believed that stabilization of the polypeptides of the invention via the formation of a synthetic linkage, such as a disulfide bridge formed by incorporation of cysteine residues or a synthetic peptide bond created between particular amino acid residues, more closely mimics the native conformation of these polypeptides within the CbpA protein (i.e., stabilizes these alpha helices into a hairpin loop structure similar to the folding of these polypeptide regions within native the CbpA protein). The $R2_1$ and $R2_2$ loop polypeptides thereby have increased protective immunogenicity relative to those polypeptides that are not stabilized in the desired loop conformation (e.g., linear versions of these polypeptides). Incorporation of an amino acid sequence for a T cell epitope into an $R2_1$ or $R2_2$ loop polypeptide of the invention may serve to further increase the immunogencity of the resultant polypeptides.

Isolated nucleic acid molecules that encode the $R2_1$ and $R2_2$ loop polypeptides of the invention are also disclosed herein. Compositions of the invention further include immunogenic compositions and vaccines comprising a pharmaceutically acceptable carrier and at least one polypeptide described herein, or a mixture thereof. The present compositions find use in methods for preventing and treating pneumococcal infections.

The full-length amino acid sequence of CbpA from the Tigr4 strain of *S. pneumoniae* is set forth in SEQ ID NO:1. The N-terminal sequence of CbpA, corresponding approximately to residues 39-510 of the CbpA amino acid sequence (SEQ ID NO:3), comprises five domains referred to in the art as the A, B, R1, R2, and C domains. Of particular relevance to the present invention is the R2 domain, which as used herein refers to the amino acid sequence comprising residues 329 to 443 of CbpA from the *S. pneumoniae* Tigr4 strain (SEQ ID NO:5). The term "$R2_1$ polypeptide" refers to an amino acid sequence comprising residues 329 to 391 of CbpA (SEQ ID NO:7), or a variant or fragment thereof. An "$R2_2$ polypeptide" refers to an amino acid sequence comprising residues 361 to 443 of CbpA (SEQ ID NO:9), or a variant or fragment thereof. The three-dimensional structures of the $R2_1$ and $R2_2$ polypeptides each comprise two alpha helices connected by a flexible linker. Since the R1 domain is 77% identical in sequence to the R2 domain of CbpA, one skilled in the art would appreciate that analogous regions of R1 are potential substitutes for R2 sequences.

An exemplary $R2_1$ cysteine mutant loop polypeptide of the invention is set forth in SEQ ID NO:15 and comprises amino acid residues 329-391 of the CbpA protein, wherein the valine at position 333 and the lysine at position 386 have each been engineered to comprise a cysteine residue. An exemplary $R2_2$ cysteine mutant polypeptide of the invention is set forth in SEQ ID NO:17 and comprises amino acid residues 361-443 of the CbpA protein, wherein the lysine at position 364 and the valine at position 439 have each been engineered to comprise a cysteine residue. Additional $R2_1$ cysteine mutant polypeptides include, but are not limited to, the amino acid sequences set forth in SEQ ID NOs:21, 25, 41 and 67-70. Additional $R2_2$ cysteine mutant polypeptides include, but are not limited to, the amino acid sequences set forth in SEQ ID NOs:29, 33, 43, and 71-74. Any polypeptide comprising a variant or fragment of the $R2_1$ or $R2_2$ domain of CbpA that has been engineered to comprise at least one cysteine residue such that the incorporated cysteine residues form a disulfide bridge that stabilizes the polypeptide in a desired conformation is encompassed by the present invention. $R2_1$ and $R2_2$ cysteine mutant loop polypeptides further comprising an amino acid sequence for a T cell epitope are also encompassed by the invention and include, for example, the amino acid sequences set forth in SEQ ID NOs:41, 43, and 67-74.

An exemplary $R2_1$ loop polypeptide of the invention, wherein the polypeptide has been modified to create a synthetic linkage between at least a first and a second amino acid residue present in the polypeptide such that the linkage stabilizes the polypeptide in a loop conformation, comprises the amino acid sequence set forth in SEQ ID NO:11. In one embodiment, polypeptides comprising SEQ ID NO:11 can be flanked by twelve or twenty amino acids (i.e., from the native $R2_1$ sequence) on each side and stabilized in loop conformations by creating a synthetic peptide linkage between, for example, the E348 residue and the K364 residue. In other embodiments, $R2_2$ loop polypeptides comprising the amino acid sequence set forth in SEQ ID NO:13 can be flanked by twelve or nineteen amino acids (i.e., from the native $R2_2$ sequence) on each side and stabilized in loop conformations by creating a synthetic peptide linkage between, for example, the E393 and the K402 residues.

Figure 2:
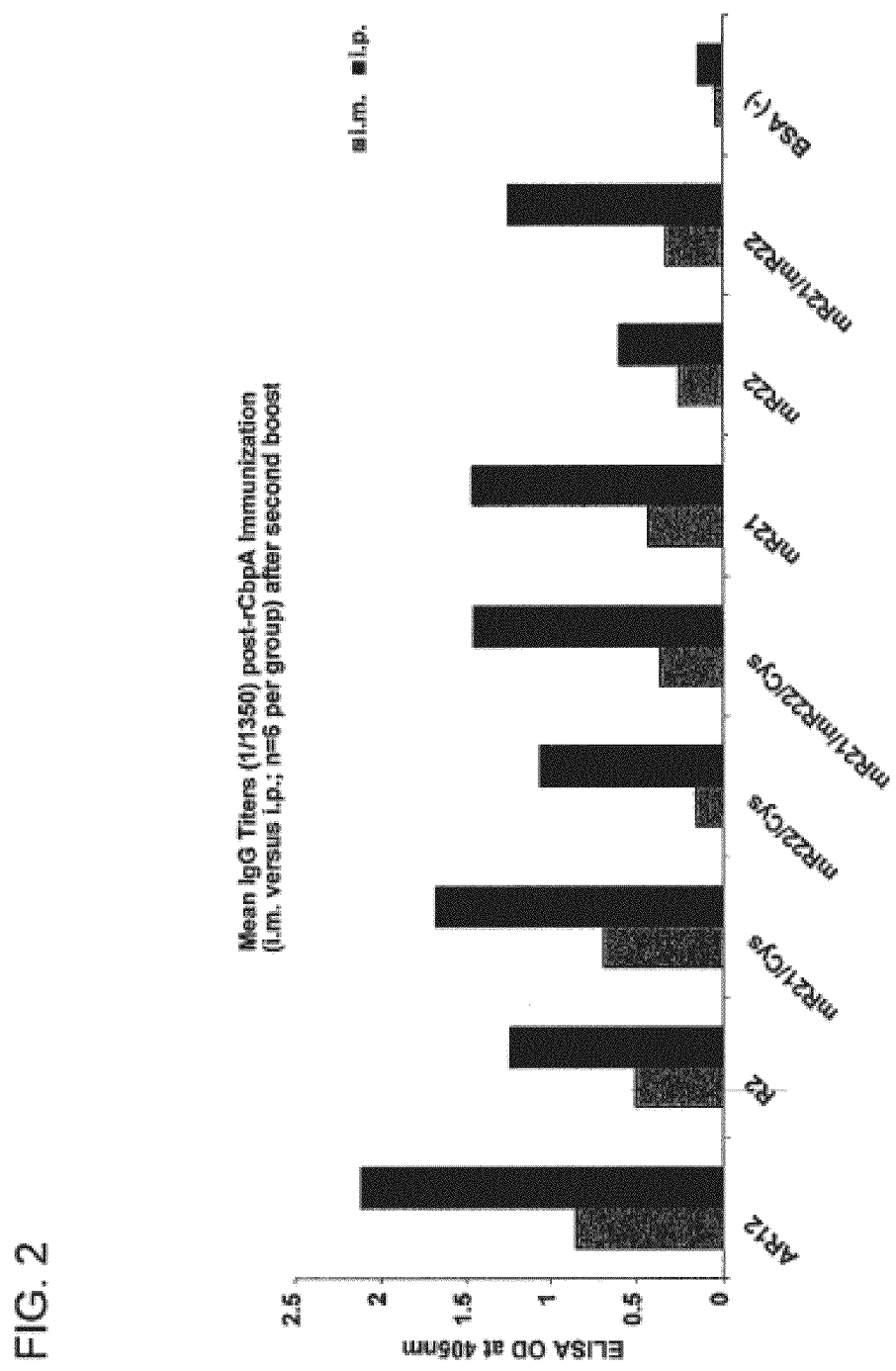
Figure 3:
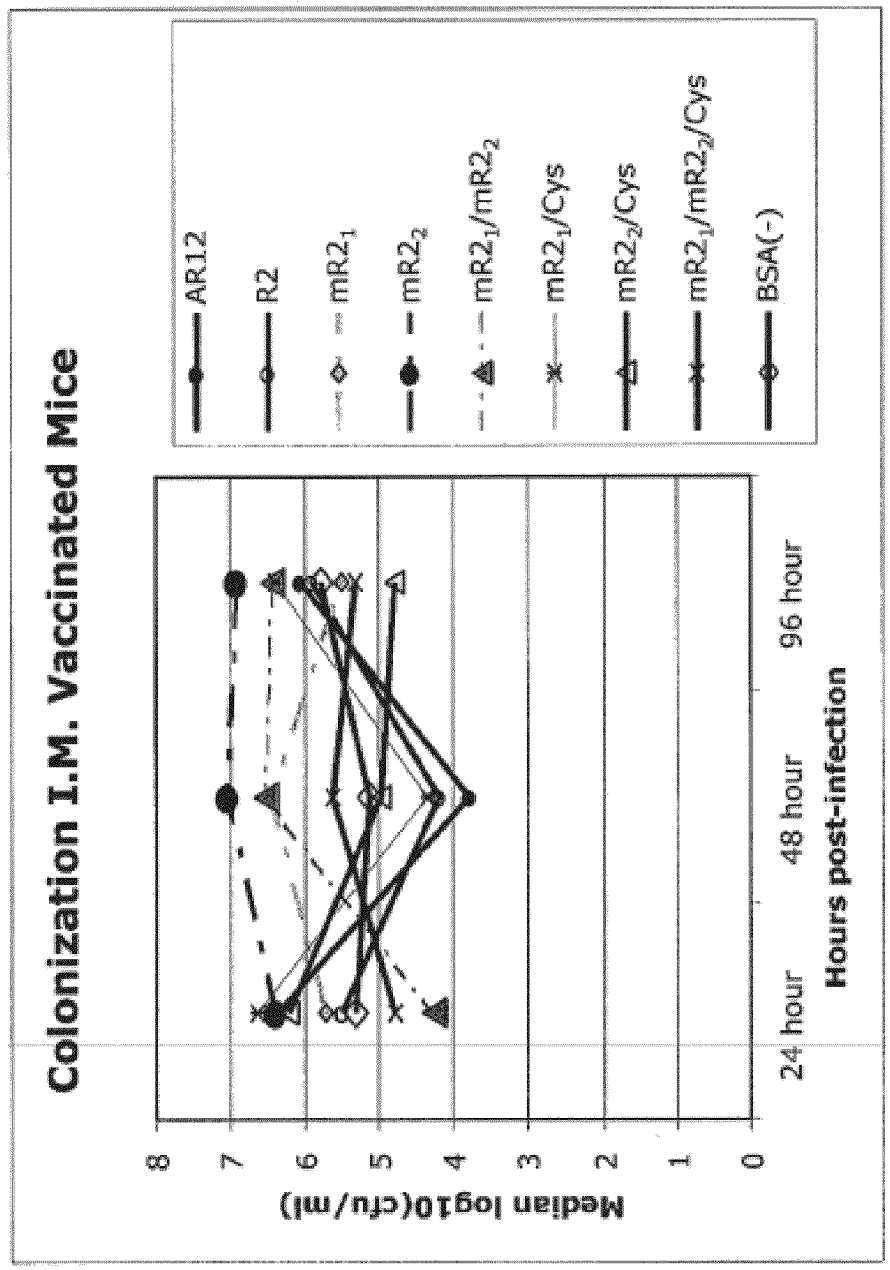
FIG. 3 presents the level of nasal colonization by S. pneumoniae 24, 48, and 96 hours post-infection of mice immunized intramuscularly with the polypeptide constructs of Example 2. Additional experimental details are provided in Example 2.
Figure 1:
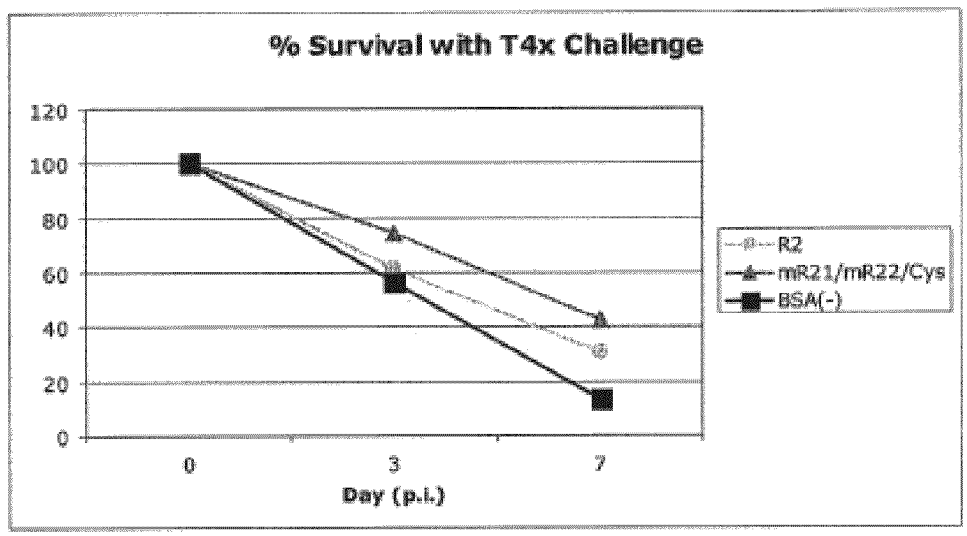
Figure 6:
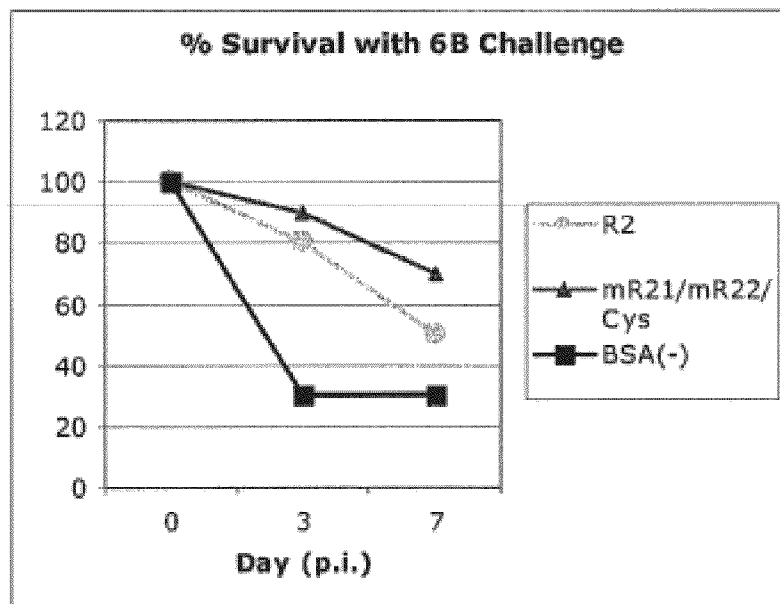
Figure 2:
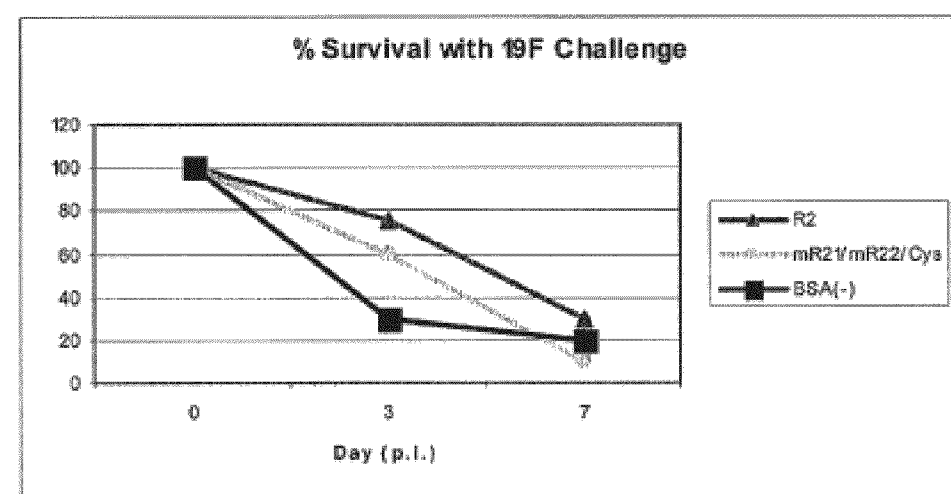

Schematic representations of the $R2_1$ and $R2_2$ cysteine mutant loop polypeptide constructs set forth in SEQ ID NO:15 and 17 are presented in FIG. 1-2B. Elucidation of the structure of these polypeptides by circular dichroism (CD) indicates that these modified polypeptides have a significantly more helical structure than the linear polypeptides that lack the engineered cysteine residues and the resulting disulfide bridge. Moreover, these $R2_1$ and $R2_2$ cysteine mutant loop polypeptides were shown to have a secondary structure similar to that of the native R2 domain of CbpA (data not shown). Similarly, the $R2_1$ and $R2_2$ loop polypeptides comprising a synthetic linkage that stabilizes the polypeptide in the desired conformation also show significantly more helical structure than the corresponding linear polypeptides. Although the invention is not limited to a specific mechanism of action, the stabilization of the $R2_1$ and $R2_2$ polypeptides of the invention by either the incorporation of cysteine residues and the resulting formation of a disulfide bridge or the formation of a synthetic linkage between amino acid residues may increase the immunogenicity of these polypeptides relative to the corresponding polypeptides lacking either of these two modifications, specifically because the $R2_1$ and $R2_2$ loop polypeptides may more closely mimic the three-dimensional structure of those regions of the native CbpA protein. The three-dimensional structure of CbpA is provided in FIG. 1-1A.

As discussed above, the $R2_1$ and $R2_2$ loop polypeptides of the invention are modified such that the polypeptide is stabilized in a desired conformation. As used herein, a "conformation" refers to the three-dimensional structure of a protein. A "desired" conformation includes a protein conformation that is conducive to a particular use of the polypeptide, e.g., as an immunogen to generate a protective response. In particular embodiments, the $R2_1$ and $R2_2$ loop polypeptides of the invention are stabilized in a hairpin loop structure similar to that present in the native protein. In certain aspects of the invention, stabilization of the R2₁ and R2₂ polypeptides in the desired hairpin loop conformation will result in increased protective immunogenicity of the polypeptide relative to the corresponding polypeptides that are not modified to be stabilized in the desired conformation, either by incorporation of cysteine residues or creation of a synthetic peptide bond between existing amino acid residues present in the polypeptide. Immunogenicity of the disclosed loop polypeptides may be further enhanced by incorporation of an amino acid sequence for a T cell epitope.

It is recognized that the first and the second cysteine residues of the various cysteine mutant loop polypeptides of the invention can be located in a variety of positions in the polypeptide to allow for the formation of the disulfide bond to stabilize the desired conformation. Similarly, a synthetic linkage between amino acids present in an R2₁ or R2₂ polypeptide, wherein the synthetic linkage stabilizes the polypeptide in a desired conformation, can be created at a variety of positions within the polypeptide. The exact placement of the cysteine residues or synthetic peptide bond may be selected in view of the known three-dimensional structure of the domain to be stabilized (i.e., the R2 domain of the CbpA protein.) For example, the first and the second cysteine residues (or amino acid residues between which the synthetic peptide bond is formed) can be external to (i.e., be found outside or flank) the amino acid sequence of SEQ ID NO: 7, 9, 11, or 13, or a biologically active variant or fragment thereof. By "flank" is intended that the engineered cysteine residues or amino acid residues of the synthetic linkage are adjacent to or within a few amino acid residues of the amino acid sequence of SEQ ID NO:7, 9, 11, or 13, or a biologically active variant or fragment thereof. In other embodiments, at least one or both of the cysteine residues or amino acid residues of the synthetic linkage is located internal to the amino acid sequence of SEQ ID NOS:7, 9, 11, or 13, or the biologically active variant or fragment thereof. In specific embodiments, at least the first cysteine residue (or first amino acid of the synthetic peptide bond) is located near the amino terminal portion of the polypeptide and/or the second cysteine residue (or second amino acid of the synthetic peptide bond) is located near the carboxy terminal portion of the polypeptide.

By "near the amino and carboxy terminal portions of the polypeptide" is intended that the cysteine residue or amino acid residue of the synthetic linkage (e.g., synthetic peptide bond) is typically located within 1, 2, 3, 4, 5, 6, 7, 8, 9, or 10 residues from the amino or carboxy terminus. Moreover, in some embodiments, the term "near the amino terminus" or "near the carboxy terminus" is a relative term meaning that one amino acid residue (e.g., an engineered cysteine residue) is closer to the amino or carboxy terminus with respect to the other amino acid residue.

In particular embodiments, an R2₁ or R2₂ loop polypeptide of the invention, more particularly an R2₁ or R2₂ cysteine mutant loop polypeptide, is engineered such that the polypeptide further comprises an amino acid sequence for a T cell epitope (TCE). See, for example, the TCE sequence of SEQ ID NO:49 (i.e., QYIKANSKFIGITGG), SEQ ID NO:65 (QYIKANSKFIGITQYIKANSKFIGITGG), and SEQ ID NO:66 (PVVEVNGVTIQVGSRGG). Immunogenicity may be increased by the addition of such a TCE sequence to an R2₁ or R2₂ loop polypeptide disclosed herein, particularly since small synthetic peptides are sometimes not as effective at inducing a protective antibody response against a pathogen of interest. See, for example, El Kasmi et al. (2000) *J. Gen. Virol.* 81:729-735 and Obeid et al. (1995) *J. Virol.* 69:1420-1428. For example, short, synthetic peptides may lack the T cell stimulating sequences required for the induction of immuno- globulin class switch and affinity maturation of the antibodies, a prerequisite for the induction of a protective antibody response. Covalent linkage of a short peptide sequence recognized by T cells (referred to herein generally as a T cell epitope or a "TCE") may circumvent this. See, generally, El Kasmi et al. (1999) *Vaccine* 17:2436-2445; El Kasmi et al. (1998) *Mol. Immunol.* 35:905-918; El Kasmi et al. (2000)*J. Gen. Virol.* 81:729-735; Obeid et al. (1995) *J. Virol.* 69:1420-1428; and Bouche et al. (2005) *Vaccine* 23:2074-2077. Thus, for example, an amino acid sequence for a TCE may be linked to an R2₁ or R2₂ loop polypeptide of the invention (e.g., an R2₁ or R2₂ cysteine mutant loop polypeptide) to increase the immunogenicity of the polypeptide relative to that of the same polypeptide lacking the TCE sequence. Such polypeptides comprising a TCE sequence are generally between about 30 and about 45 amino acids in length.

The TCE sequences utilized in the present invention are typically short sequences (e.g. about 10-25 amino acids, particularly about 15-20 amino acids, more particularly about 15 amino acids in length). TCE sequences can be readily synthesized using standard methods known in the art. Desired TCE sequences will generally: 1) induce T cell activation in a large portion of the population (i.e., be recognized by many different MHC/HLA haplotypes ("promiscuous" TCE's); see Demotz et al. (1989) *J. Immunology* 142:394-402) and 2) not interfere with the conformation or affect the immunogenicity of the B cell epitope (BCE) to which it is attached. The relative position and stoichiometry of the TCE sequence(s) within the R2₁ or R2₂ loop polypeptides of the invention may be important for the overall immunogenicity of the TCE and BCE and the overall polypeptide conformation. Identification of optimal TCE sequences for use in the practice of the present invention is well within the capabilities of one of skill in the art. Such TCE sequences may be determined empirically by the skilled artisan.

Exemplary TCE sequences for use in the invention include but are not limited to TCE tt830 (QYIKANSKFIGIT; SEQ ID NO:56), TCE F421 (PVVEVNGVTIQVGSR; SEQ ID NO:57), SEQ ID NO:65 (QYIKANSKFIGITQYIKANSKFIGITGG), and SEQ ID NO:66 (PVVEVNGVTIQVGSRGG). The TCE tt830 TCE sequence was derived from tetanus toxoid and has been shown to be recognized by T cells of many different HLA and MHC haplotypes, in both human and mouse subjects. See Demotz et al. (1989) *J Immunology* 142:394-402. TCE F421 has also been demonstrated to be effective in inducing protective immunity in mouse models. See El Kasmi et al. (1999) *Vaccine* 17:2436-2445 and El Kasmi et al. (2000) *J. Gen. Virol.* 81:729-735. Both of these TCEs have been covalently linked to BCEs in previous studies, resulting in the production of more highly immunogenic polypeptides. See, for example, El Kasmi et al. (1999) *Vaccine* 17:2436-2445; El Kasmi et al. (1998) *Mol. Immunol.* 35:905-918; and Bouche et al. (2005) *Vaccine* 23:2074-2077.

Compositions further include immunogenic compositions and vaccines comprising an R2₁ and/or R2₂ loop polypeptide. Immunogenic compositions of the invention comprise at least one polypeptide as described herein in combination with a pharmaceutically acceptable carrier. In some embodiments, the polypeptide is present in an amount effective to elicit antibody production when administered to an animal. In specific embodiments, the immunogenic composition comprises an R2₁ and/or an R2₂ cysteine mutant loop polypeptide, more particularly a cysteine mutant loop polypeptide further comprising a T cell epitope sequence. Methods for detecting antibody production in an animal are well known in the art.

Vaccines for treating or preventing pneumococcal infection are further provided and comprise at least one loop polypeptide of the invention in combination with a pharmaceutically acceptable carrier, wherein the loop polypeptide is present in an amount effective for treating or preventing a pneumococcal infection. In particular embodiments, the vaccine elicits production of protective antibodies against *S. pneumoniae* when administered to an animal. In specific embodiments, the vaccine comprises an $R2_1$ and/or $R2_2$ cysteine mutant loop polypeptide. In other embodiments, the vaccine comprises an $R2_1$ and/or $R2_2$ loop polypeptide that comprises a synthetic peptide bond between amino acid residues present in the polypeptide, wherein the synthetic peptide bond stabilizes the polypeptide in a desired conformation, more particularly a loop conformation.

The immunogenic compositions and vaccines disclosed herein may further comprise a mixture of $R2_1$ and $R2_2$ loop polypeptides, such as, for example, a first polypeptide comprising an $R2_1$ cysteine mutant polypeptide and a second polypeptide comprising an $R2_2$ cysteine mutant polypeptide. Other exemplary immunogenic compositions or vaccines comprise a first polypeptide comprising an $R2_1$ loop polypeptide and a second polypeptide comprising an $R2_2$ loop polypeptide, wherein both polypeptides comprise a synthetic linkage between amino acid residues that stabilizes the polypeptides in a loop conformation. Any combination of $R2_1$ and $R2_2$ loop polypeptides may be used in the practice of the invention. In particular embodiments, the immunogenic compositions and vaccines comprise an $R2_1$ and/or and $R2_2$ cysteine mutant loop polypeptide further linked to an amino acid sequence for a T cell epitope, such as, for example, the polypeptides set forth in SEQ ID NO:41, SEQ ID NO:43, or SEQ ID NOs:67-74.

One of skill in the art will appreciate that the $R2_1$ and $R2_2$ loop polypeptides of the invention can be used independently for purposes of immunization, or alternatively covalently coupled to or mixed with, for example, protein carriers or other pneumococcal vaccines to increase immunogenicity. For example, the loop polypeptides disclosed herein could be covalently coupled to a protein carrier such as diphtheria or tetanus toxoid. Methods for coupling polypeptides to such protein carriers are well known in the field of immunology and include the heteroligation techniques of Brunswick et al. (1988) *J. Immunol.* 140:3364, incorporated herein by reference. See also Wong (1991) Chemistry of Protein Conjugates and Crosslinking (CRC Press, Boston), incorporated herein by reference. In other embodiments, the cysteine mutant polypeptides of the invention could be mixed (i.e., without covalent conjugation) to tetanus toxoid, diphtheria toxoid, or a known *S. pneumoniae* conjugate vaccine. The polypeptides of the invention could be further synthesized with T cell epitope markers by methods available in the art, as described in detail above. Coupling or mixing the cysteine mutant polypeptides with protein carriers/existing vaccines or incorporating a T cell epitope into the polypeptide may increase the immunogenicity of the polypeptides of the invention. Moreover, in certain embodiments, the polypeptides of the invention may be added to existing pneumoccal vaccines to broaden the number of serotypes that the vaccine protects against. In these aspects of the invention, the polypeptides may be simply mixed (i.e., without covalent linkage) with existing vaccines or, alternatively, covalently linked to other pneumoccal vaccines.

Compositions further include isolated nucleic acid molecules that encode the $R2_1$ and $R2_2$ loop polypeptides of the invention, and variants and fragments thereof. Exemplary nucleic acid molecules comprising nucleotide sequences that encode the $R2_1$ and $R2_2$ cysteine mutant polypeptides or comprise the consensus sequence of SEQ ID NO:11 or 13 or biologically active variant and fragments thereof include those sequences set forth in SEQ ID NOs:16, 18, 22, 26, 30, 34, 42, and 44. Variants and fragments of the isolated nucleic acid molecules disclosed herein are also encompassed by the present invention. Vectors and expression cassettes comprising the nucleic acid molecules of the invention are further disclosed. Expression cassettes will generally include a promoter operably linked to a nucleic acid of the invention and a transcriptional and translational termination region.

The compositions of the invention find use in methods for preventing and treating pneumococcal infections. As used herein, "preventing a pneumococcal infection" is intended administration of a therapeutically effective amount of a polypeptide, immunogenic composition, or vaccine of the invention to an animal in order to protect the animal from the development of a pneumococcal infection or the symptoms thereof. In some embodiments, a composition of the invention is administered to a subject, such as a human, that is at risk for developing a pneumococcal infection. By "treating a pneumococcal infection" is intended administration of a therapeutically effective amount of a polypeptide, immunogenic composition, or vaccine of the invention to an animal that has a pneumococcal infection or that has been exposed to a pneumococcal bacterium, where the purpose is to cure, heal, alleviate, relieve, alter, remedy, ameliorate, improve, or affect the condition or the symptoms of the pneumococcal infection.

A "therapeutically effective amount" as used herein refers to that amount which provides a therapeutic effect for a given condition and administration regimen. In particular aspects of the invention, a "therapeutically effective amount" refers to an amount of a polypeptide, immunogenic composition, or vaccine of the invention that when administered to an animal brings about a positive therapeutic response with respect to the prevention or treatment of a subject for a pneumococcal infection. A positive therapeutic response with respect to preventing a pneumococcal infection includes, for example, the production of pneumococcal antibodies by the subject in a quantity sufficient to protect against development of the disease. Similarly, a positive therapeutic response in regard to treating a pneumococcal infection includes curing or ameliorating the symptoms of the disease. The phrase "therapeutically effective amount" is used herein to mean an amount sufficient to cause an improvement in a clinically significant condition in the host. In the context of the present invention, a deficit in the response of the host can be evidenced by continuing or spreading bacterial infection. An improvement in a clinically significant condition in the host includes a decrease in bacterial load, clearance of bacteria from colonized host cells, reduction in fever or inflammation associated with infection, or a reduction in any symptom associated with the bacterial infection.

In particular aspects of the invention, methods for preventing a pneumococcal infection in an animal comprise administering to the animal a therapeutically effective amount of an $R2_1$ and/or $R2_2$ loop polypeptide of the invention, particularly a polypeptide further comprising a T cell epitope (i.e., an $R2_1$ and/or $R2_2$ cysteine mutant loop polypeptide, an $R2_1$ and/or $R2_2$ loop polypeptide that comprises a synthetic peptide bond, as described above, or a biologically active variant or fragment thereof), an immunogenic composition comprising a loop polypeptide of the invention in combination with a pharmaceutically acceptable carrier, or a vaccine disclosed herein, thereby preventing a pneumococcal infection. In other embodiments, methods for treating a pneumococcal infection in an animal infected with or exposed to a pneumococcal bacterium comprise administering to the animal a therapeutically effective amount of an $R2_1$ and/or $R2_2$ loop polypeptide of the invention, an immunogenic composition comprising a loop polypeptide of the invention in combination with a pharmaceutically acceptable carrier, or a vaccine disclosed herein, thereby treating the animal. For example, in an individual already infected with a pneumococcal bacterium, a loop polypeptide of the invention could be used as passive protection against the spread of the infection from the blood to the brain.

A method of inducing an immune response in a subject which has been exposed to or infected with a pneumococcal bacterium is further provided comprising administering to the subject a therapeutically effective amount of an $R2_1$ and/or $R2_2$ loop polypeptide of the invention (i.e., an $R2_1$ and/or $R2_2$ cysteine mutant loop polypeptide, an $R2_1$ and/or $R2_2$ loop polypeptide that comprises a synthetic peptide bond, as described above, and/or a polypeptide having the consensus sequence of SEQ ID NO:11 or 13, or a biologically active variant or fragment thereof), an immunogenic composition of the invention, or a vaccine as disclosed herein, thereby inducing an immune response.

In a further embodiment, a method of detecting the presence of antibodies to a pneumococcal bacterium in a biological sample obtained from an animal is further provided. The method comprises contacting the sample with an $R2_1$ and/or $R2_2$ loop polypeptide of the invention and detecting antigen-antibody binding.

In another aspect of the invention, a CbpA polypeptide, or a biologically active variant or fragment thereof, can be employed in various methods to modulate pneumococcal colonization of the nasopharynx and, in other embodiments, can be used to modulate bacterial entry into the lung, into the bloodstream or across the blood brain barrier. Pneumococcal infection involves bacterial colonization of nasopharyngeal epithelial cells and subsequent bacterial entry into the bloodstream and, possibly, the brain. While not being bound by any theory, the present invention demonstrates that CbpA binds to pIgR during colonization of the nasopharynx by pneumococcal bacteria and to the laminin receptor during the invasive phase of the disease when the bacteria enter the bloodstream and the brain. The two binding activities have been localized to specific regions of the R2 domain of CbpA. In particular, the region referred to herein as the $R2_1$ domain appears to be responsible for binding to pIgR and bacterial colonization in the nasopharynx, whereas the $R2_2$ domain is likely involved in binding to the laminin receptor and subsequent bacterial entry into the bloodstream and brain. This information can be utilized to develop immunogenic compositions and vaccines that are protective against both steps of pneumococcal infection, namely colonization of the nasopharynx and bacterial entry into the bloodstream.

In another aspect of the invention, a CbpA polypeptide, or a biologically active variant or fragment thereof, can be employed in various methods to modulate entry of compounds of interest across the blood brain barrier. By "modulate entry" or "modulating the entry" of a compound of interest is intended any increase or decrease in the concentration or activity of the compound into a desired area. In a specific embodiment, the desired area where the concentration or activity of the compound is modulated in the central nervous system of an animal of interest. In more specific, embodiments, the desired area comprises the brain of the animal. In general, concentration and/or activity is increased or decreased by at least 1%, 5%, 10%, 20%, 30%, 40%, 50%, 60%, 70%, 80%, or 90% relative to an appropriate control or alternatively, the concentration and/or activity of the compound of interest is increased or decreased to a sufficient level to produce a desired therapeutic effect in the animal. Methods to detect the increase or decrease in the concentration or activity of the compound of interest will vary depending on the compound of interest. Representative, non-limiting examples of such assays are disclosed in further detail below.

While not being bound by any theory, the present invention demonstrates that CbpA binds to the laminin receptor and that this interaction is mediated by the $R2_2$ domain. Thus, the interaction of CbpA with the laminin receptor provides methods and compositions which modulate the entry of compounds of interest across the blood brain barrier. Furthermore, previous researchers have demonstrated that certain galactosugars disrupt the conformation of the laminin receptor that is required for binding to matrix components. Consistent with this observation, the present inventors have also shown that the binding of CbpA to the laminin receptor is inhibited by galactosugars including, for example, L-sialyl-lactose and lacto-N-neotetraose. See Example 6 below. Therefore, in specific embodiments, the entry of a compound of interest across the blood brain barrier can be decreased by providing an $R2_2$ loop polypeptide (e.g., an $R2_2$ cysteine mutant loop polypeptide, particularly a polypeptide further comprising an amino acid sequence for a T cell epitope) or by providing a galactosugar (e.g., L-sialyl-lactose or lacto-N-neotetraose) that disrupts adhesion to the laminin receptor.

A number of infectious agents cause neurological disease. Many of these neurotropic infectious agents bind to laminin receptors present on endothelial cells, thereby permitting the entry of these agents into the brain. The present invention reports for the first time that *Neisseria meningitidis* and *Haemophilus influenzae* bind to the laminin receptor. See Example 6. In this embodiment, the native, full-length CbpA polypeptide or a biologically active variant or fragment thereof which continues to have the ability to interact with the laminin receptor and cross the blood brain barrier can be administered to subjects infected by or exposed to such a neurotropic infectious agent in order to interfere with the binding of these agents to laminin receptors, thereby blocking entry of these agents into the brain. That is, the CbpA polypeptide or a biologically active variant or fragment thereof can function as competitive inhibitors for binding of neurotropic infectious agents to laminin receptors and decrease the entry of these agents across the blood brain barrier and into the brain of an animal, thereby preventing the development of neurological diseases. Similarly, galactosugars that disrupt binding of neurotropic infectious agents to laminin receptors may be used to inhibit entry of these neurotropic agents into the brain.

Methods of inhibiting adhesion of neurotropic infectious agents, such as pneumococcal bacteria, to endothelial cells comprising providing an $R2_2$ loop polypeptide, such as an $R2_2$ cysteine mutant loop polypeptide that further comprises a T cell epitope, or a galactosugar that disrupts adhesion to laminin receptors are further provided. Methods of inhibiting adhesion of pneumococcal bacteria to endothelial cells comprising providing laminin receptor antibodies is also encompassed by the present invention. In other aspects of the invention, methods for inhibiting entry of a neurotropic agent into the brain of animal are provided. Methods for inhibiting entry of a neurotropic agent (e.g., *Streptococcus pneumoniae*, *Neisseria meningitidis*, or *Haemophilus influenzae*) into the brain comprise administering to the animal a therapeutically effective amount of at least one compound selected from the group consisting of 1) a galactosugar that disrupts the conformation of the laminin receptor (e.g., L-sialyl-lactose or lacto-N-neotetraose), 2) an $R2_2$ loop polypeptide, or variant or fragment thereof (e.g., an $R2_2$ cysteine mutant loop polypeptide), and 3) a laminin receptor antibody, or fragment thereof.

While not intending to be limited to a particular mechanism, administration of one or more of the above compounds likely inhibits binding of the neurotropic agent to laminin receptors present on endothelial cells of the blood brain barrier, thereby inhibiting entry of the neurotropic agent into the brain of the animal. As used herein, "inhibiting the entry of a neurotropic agent into the brain" refers to decreasing the amount of the neurotropic agent able to cross the blood brain barrier and invade brain tissue by at least about 1%, 5%, 10%, 20%, 30%, 40%, 50%, 60%, 70%, 80%, 90% or more relative to an appropriate control (e.g., the amount of the neurotropic agent that enters the brain in the absence of one of the above compounds). Alternatively, the amount of neurotropic agent entering the brain may be reduced to a level sufficient to produce a desired therapeutic effect in the animal.

An "immunogen" is a substance that induces an immune response. As used herein, the term immunogenicity refers to the ability of a substance to induce an immune response when administered to an animal. A substance such as a polypeptide displays "increased immunogenicity" relative to another polypeptide when administration of the first polypeptide to an animal results in a greater immune response than that observed with administration of the other polypeptide. In some embodiments of the invention, the $R2_1$ or $R2_2$ loop polypeptides (including, for example, an $R2_1$ and/or $R2_2$ cysteine mutant polypeptide and/or a polypeptide having the consensus sequence of SEQ ID NO:11 or 13, or a biologically active variant or fragment thereof), will display an increased immunogenicity relative to the corresponding polypeptides that are not stabilized in the desired conformation, particularly a loop conformation. Furthermore, incorporation of an amino acid sequence for a T cell epitope may function to increase immunogenicity of an $R2_1$ or $R2_2$ loop polypeptide. An increase in immunogenicity may refer to not only a greater response in terms of the production of more antibody but also the production of more protective antibody.

The invention encompasses isolated or substantially purified polypeptide and nucleic acid compositions. "Isolated" in the context of the present invention with respect to polypeptides and nucleic acid means that the material is removed from its original environment (e.g., the natural environment if it is naturally occurring). Thus, an isolated or purified polypeptide or nucleic acid molecule is substantially free of other cellular material, or culture medium when produced by recombinant techniques, or substantially free of chemical precursors or other chemicals when chemically synthesized. The polypeptides of the vaccines disclosed herein are typically provided in an isolated form, are optimally synthetic, and generally are purified to homogeneity for use in pharmaceutical compositions.

Use of the term a "nucleic acid molecule" or "nucleotide sequence" is not intended to limit the present invention to polynucleotides comprising DNA. One of skill in the art will appreciate that nucleic acid molecules can comprise ribonucleotides, deoxyribonucleotides, and combinations thereof. A "DNA" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

Variants and fragments of the polypeptides and nucleic acid molecules of the invention (i.e., the native CbpA protein, the $R2_1$ or $R2_2$ loop polypeptides), and the various $R2_1$ and $R2_2$ cysteine mutant loop polypeptides are also disclosed herein. "Variants" refer to substantially similar sequences. A variant of an amino acid or nucleotide sequence of the invention will typically have at least about 65%, 70%, 75%, 80%, 85%, 90%, 91%, 92%, 93%, 94%, 95%, 96%, 97%, 98%, 99% or more sequence identity with the reference sequence. In particular embodiments, a variant of a polypeptide of the invention will retain the biological activity of the full-length polypeptide and hence be immunogenic and protective, interact with the laminin receptor, interact with the IgR receptor, or interact with both receptors.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix. By "equivalent program" is intended any sequence comparison program that, for any two sequences in question, generates an alignment having identical nucleotide or amino acid residue matches and an identical percent sequence identity when compared to the corresponding alignment generated by GAP Version 10.

The term "fragment" refers to a portion of an amino acid or nucleotide sequence comprising a specified number of contiguous amino acid or nucleotide residues. In particular embodiments, a fragment of a polypeptide of the invention may retain the biological activity of the full-length polypeptide and hence be immunogenic, interact with the laminin receptor, interact with the IgR receptor, or interact with both receptors. Fragments of a polynucleotide may encode protein fragments that retain the biological activity of the protein and hence be immunogenic, interact with the laminin receptor. Thus, fragments of a polynucleotide may range from at least about 20, 30, 40, 50, 60, 70, 80, 90, 100, 110, 120, 130, 140, 150, 175, 200, 225, 250, 300, 400, 500, 600, 700, 800, 900, 1000, 1100, 1200, 1300, 1400, or 1500 contiguous nucleotides or up to the full-length polynucleotide. Fragments of a polypeptide sequence may comprise at least 15, 25, 30, 50, 60, 70, 80, 90, 100, 110, 120, 130, 140, 150, 160, 170, 180, 190, 200, 225, 250, 275, 300, 400, 425, 450, 475, or 500 contiguous amino acids, or up to the total number of amino acids present in a full-length protein.

As used herein the term "recombinantly engineered" or "engineered" connotes the utilization of recombinant DNA technology to introduce (e.g., engineer) a change in the protein structure based on an understanding of the protein's mechanism of action and a consideration of the amino acids being introduced, deleted, or substituted. Methods for engineering the incorporation of specific amino acid residues into a polypeptide are well known in the art.

Mutations can be made in a nucleic acid encoding the polypeptide such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point. In specific embodiments, the mutation comprises at least an insertion or a substitution of a cysteine residue.

Synthetic DNA sequences allow convenient construction of genes which will express analogs or "muteins". A general method for site-specific incorporation of unnatural amino acids into proteins is described in Noren, et al. *Science*, 244: 182-188 (April 1989). This method may be used to create analogs with unnatural amino acids.

In accordance with the present invention there may be employed conventional molecular biology, microbiology, and recombinant DNA techniques within the skill of the art. Such techniques are explained fully in the literature. See, e.g., Sambrook et al., "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

This invention also provides a vector which comprises the above-described nucleic acid molecules operably linked to a promoter. A nucleotide sequence is "operably linked" to an expression control sequence (e.g., a promoter) when the expression control sequence controls and regulates the transcription and translation of that sequence. The term "operably linked" includes having an appropriate start signal (e.g., ATG) in front of the nucleotide sequence to be expressed and maintaining the correct reading frame to permit expression of the sequence under the control of the expression control sequence and production of the desired product encoded by the sequence. If a gene that one desires to insert into a recombinant nucleic acid molecule does not contain an appropriate start signal, such a start signal can be inserted in front of the gene. A "vector" is a replicon, such as plasmid, phage or cosmid, to which another nucleic acid segment may be attached so as to bring about the replication of the attached segment. The promoter may be, or is identical to, a bacterial, yeast, insect or mammalian promoter. Further, the vector may be a plasmid, cosmid, yeast artificial chromosome (YAC), bacteriophage or eukaryotic viral DNA.

Other numerous vector backbones known in the art as useful for expressing protein may be employed. Such vectors include, but are not limited to: adenovirus, simian virus 40 (SV40), cytomegalovirus (CMV), mouse mammary tumor virus (MMTV), Moloney murine leukemia virus, DNA delivery systems, i.e. liposomes, and expression plasmid delivery systems. Further, one class of vectors comprises DNA elements derived from viruses such as bovine papilloma virus, polyoma virus, baculovirus, retroviruses or Semliki Forest virus. Such vectors may be obtained commercially or assembled from the sequences described by methods well-known in the art.

This invention also provides a host vector system for the production of a polypeptide which comprises the vector of a suitable host cell. Suitable host cells include, but are not limited to, prokaryotic or eukaryotic cells, e.g. bacterial cells (including gram positive cells), yeast cells, fungal cells, insect cells, and animal cells. Numerous mammalian cells may be used as hosts, including, but not limited to, the mouse fibroblast cell NIH 3T3, CHO cells, HeLa cells, Ltk⁻ cells etc. Additional animal cells, such as R1.1, B-W and L-M cells, African Green Monkey kidney cells (e.g., COS1, COS 7, BSC1, BSC40, and BMT10), insect cells (e.g., Sf9), and human cells and plant cells in tissue culture can also be used.

A wide variety of host/expression vector combinations may be employed in expressing the nucleotide sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences (sequences that control the expression of a nucleotide sequence operably linked to it) may be used in these vectors to express the nucleotide sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., PhoS), the promoters of the yeast a-mating factors, and other sequences known to control the expression of genes of prokaryotic or eukaryotic cells or their viruses, and various combinations thereof.

It will be understood that not all vectors, expression control sequences and hosts will function equally well to express the nucleotide sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular nucleotide sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the nucleotide sequences to be expressed, and the ease of purification of the expression products.

This invention further provides a method of producing a polypeptide which comprises growing the above-described host vector system under suitable conditions permitting the production of the polypeptide and recovering the polypeptide so produced.

This invention further provides an antibody capable of specifically recognizing or binding to an isolated $R2_1$ or $R2_2$ loop polypeptide polypeptide of the invention, particularly an $R2_1$ and $R2_2$ cysteine mutant loop polypeptide, a modified $R2_1$ or $R2_2$ loop polypeptide comprising a synthetic linkage between amino acid residues, as described above, or a polypeptide comprising the consensus sequence of SEQ ID NO:11 or 13. The antibody may be a monoclonal or polyclonal antibody. Further, the antibody may be labeled with a detectable marker that is a radioactive, colorimetric, fluorescent, or a luminescent marker. The labeled antibody may be a polyclonal or monoclonal antibody. In one embodiment, the labeled antibody is a purified labeled antibody. Methods of labeling antibodies are well known in the art.

The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. Such antibodies include but are not limited to polyclonal, monoclonal, chimeric, single chain, Fab fragments, and an Fab expression library.

Various procedures known in the art may be used for the production of polyclonal antibodies to polypeptide or derivatives or analogs thereof (see, e.g., *Antibodies—A Laboratory Manual*, Harlow and Lane, eds., Cold Spring Harbor Laboratory Press: Cold Spring Harbor, N.Y., 1988). For the production of antibody, various host animals can be immunized by injection with the truncated CbpA, or a derivative (e.g., fragment or fusion protein) thereof, including but not limited to rabbits, mice, rats, sheep, goats, etc. In one embodiment, the polypeptide can be conjugated to an immunogenic carrier, e.g., bovine serum albumin (BSA) or keyhole limpet hemocyanin (KLH). Various adjuvant may be used to increase the immunological response, depending on the host species.

For preparation of monoclonal antibodies, or fragment, analog, or derivative thereof, any technique that provides for the production of antibody molecules by continuous cell lines in culture may be used (see, e.g., *Antibodies—A Laboratory Manual*, Harlow and Lane, eds., Cold Spring Harbor Laboratory Press: Cold Spring Harbor, N.Y., 1988). These include but are not limited to the hybridoma technique originally developed by Kohler and Milstein (1975) *Nature* 256:495-497, as well as the trioma technique, the human B-cell hybridoma technique (Kozbor et al. (1983) *Immunology Today* 4:72), and the EBV-hybridoma technique to produce human monoclonal antibodies (Cole et al., 1985, in *Monoclonal Antibodies and Cancer Therapy*, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al. (1983) *Proc. Natl. Acad. Sci. U.S.A.* 80:2026-2030) or by transforming human B cells with EBV virus in vitro (Cole et al., 1985, in *Monoclonal Antibodies and Cancer Therapy*, Alan R. Liss, pp. 77-96). In fact, according to the invention, techniques developed for the production of "chimeric antibodies" (Morrison et al. (1984) *J. Bacteriol.* 159-870; Neuberger et al. (1984) *Nature* 312:604-608; Takeda et al. (1985) *Nature* 314:452-454) by splicing the genes from a mouse antibody molecule specific for a polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves. An additional embodiment of the invention utilizes the techniques described for the construction of Fab expression libraries (Huse et al. (1989) *Science* 246:1275-1281) to allow rapid and easy identification of monoclonal Fab fragments with the desired specificity for the polypeptide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Antibodies can be labeled for detection in vitro, e.g., with labels such as enzymes, fluorophores, chromophores, radioisotopes, dyes, colloidal gold, latex particles, and chemiluminescent agents. Alternatively, the antibodies can be labeled for detection in vivo, e.g., with radioisotopes (preferably technetium or iodine); magnetic resonance shift reagents (such as gadolinium and manganese); or radio-opaque reagents.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. The polypeptide can also be labeled with a radioactive element or with an enzyme. The radioactive label can be detected by any of the currently available counting procedures. The preferred isotope may be selected from $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

This invention provides a vaccine that comprises at least one $R2_1$ or $R2_2$ loop polypeptide, particularly an $R2_1$ or $R2_2$ cysteine mutant loop polypeptide, more particularly an $R2_1$, or $R2_2$ cysteine mutant loop polypeptide further comprising a T cell epitope, in combination with a pharmaceutically acceptable carrier. In addition, compositions comprising the CbpA polypeptide or biologically active variant or fragment thereof and a compound of interest that provides a beneficial therapeutic effect to the central nervous system are provided in combination with a pharmaceutically acceptable carrier. The polypeptides of the invention can be prepared in an admixture with an adjuvant to prepare a vaccine. Pharmaceutically acceptable carriers and adjuvants are well known in the art. Methods for formulating pharmaceutical compositions and vaccines are generally known in the art. A thorough discussion of formulation and selection of pharmaceutical acceptable carriers, stabilizers, and isomolytes can be found in *Remington's Pharmaceutical Sciences* (18$^{th}$ ed.; Mack Publishing Company, Eaton, Pa., 1990), herein incorporated by reference. A vaccine of the present invention may comprise, for example, at least one of the cysteine mutant polypeptides set forth in SEQ ID NOs:21, 25, 29, 33, 41, 43, 67-74, or a biologically active variant or fragment thereof. In particular embodiments, a vaccine comprises a mixture of at least one $R2_1$ cysteine mutant loop polypeptide and at least one $R2_2$ cysteine mutant loop polypeptide. In another embodiment, a vaccine comprises a mixture of at least one $R2_1$ loop polypeptide and at least one $R2_2$ loop polypeptide, wherein the $R2_1$ and $R2_2$ loop polypeptides have been modified to create a synthetic peptide bond between at least a first and a second amino acid residue such that the polypeptide is stabilized in the desired loop conformation. Because, as described above, the $R2_1$ domain is believed to be involved in bacterial colonization of the nasopharynx and the $R2_2$ domain likely mediates bacterial entry into the bloodstream, a vaccine that comprises both an $R2_1$ and an $R2_2$ loop polypeptide may provide protection against both steps involved in pneumococcal infection. In other embodiments, the vaccine comprises a mixture of at least one loop polypeptide having the consensus sequence of SEQ ID NO:11 or 13, or a biologically active variant or fragment thereof.

Active immunity against Gram positive bacteria, particularly pneumococcus, can be induced by immunization (vaccination) with an immunogenic amount of the polypeptide, or peptide derivative or fragment thereof, and an adjuvant, wherein the polypeptide, or antigenic derivative or fragment thereof, is the antigenic component of the vaccine.

Vectors containing a nucleic acid-based vaccine of the invention can be introduced into the desired host by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al. (1992) *J. Biol. Chem.* 267:963-967; Wu and Wu (1988) *J. Biol. Chem.* 263:14621-14624; Hartmut et al., Canadian Patent Application No. 2,012,311, filed Mar. 15, 1990).

The vaccines of the invention can be administered via any parenteral route, including but not limited to intramuscular, intraperitoneal, intravenous, and the like.

Preferably, since the desired result of vaccination is to elucidate an immune response to the antigen, and thereby to the pathogenic organism, administration directly, or by targeting or choice of a viral vector, indirectly, to lymphoid tissues, e.g., lymph nodes or spleen, is desirable. Since immune cells are continually replicating, they are ideal target for retroviral vector-based nucleic acid vaccines, since retroviruses require replicating cells.

Methods of conferring passive immunity to, for example, *Streptococcus pneumoniae, Neisseria meningitidis*, and *Haemophilus influenzae* in a subject are also encompassed by the invention. Passive immunity can be conferred to an animal subject suspected of suffering an infection with a Gram positive bacterium, preferably streptococcal, and more preferably pneumoccal, by administering antiserum, polyclonal antibodies, or a neutralizing monoclonal antibody against a polypeptide of the invention to the patient. See Example 9 below. Although passive immunity does not confer long term protection, it can be a valuable tool for the treatment of a bacterial infection of a subject who has not been vaccinated. Passive immunity is particularly important for the treatment of antibiotic resistant strains of Gram positive bacteria, since no other therapy may be available. Preferably, the antibodies administered for passive immune therapy are autologous antibodies. For example, if the subject is a human, preferably the antibodies are of human origin or have been "humanized," in order to minimize the possibility of an immune response against the antibodies. The active or passive vaccines of the invention can be used to protect an animal subject from infection of a Gram positive bacteria, preferably *streptococcus*, and more preferably, pneumococcus.

In some embodiments, a pharmaceutical composition comprising an antibody specific to a cysteine mutant polypeptide of the invention in combination with a pharmaceutically acceptable carriers is provided. These pharmaceutical antibody compositions find use in treating a subject that has been exposed to or is infected with a pneumococcal bacterium. Methods for treating a subject or an animal infected with or exposed to a pneumococcal bacterium comprising administering to the animal a therapeutically effective amount of a pharmaceutical antibody composition, as described herein above, thereby treating the animal. This invention also provides a method for preventing infection by a pneumococcal bacterium in a subject comprising administering to the subject a therapeutically effective amount of a pharmaceutical composition comprising the antibody specific for the $R2_1$ or $R2_2$ loop polypeptide, particularly an $R2_1$ or $R2_2$ cysteine mutant loop polypeptide, more particularly an $R2_1$ or $R2_2$ cysteine mutant loop polypeptide further comprising a T cell epitope, and a pharmaceutically acceptable carrier or diluent, thereby preventing infection by a pneumococcal bacterium.

As used herein, "pharmaceutical composition" could mean therapeutically effective amounts of an $R2_1$ or $R2_2$ loop polypeptide, particularly an $R2_1$ or $R2_2$ cysteine mutant loop polypeptide, more particularly an $R2_1$ or $R2_2$ cysteine mutant loop polypeptide further comprising a T cell epitope, or a CbpA polypeptide, or biologically active variant or fragment thereof, together with suitable diluents, preservatives, solubilizers, emulsifiers, adjuvant and/or carriers useful in SCF (stem cell factor) therapy. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts). solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Controlled or sustained release compositions include formulation in lipophilic depots (e.g., fatty acids, waxes, oils). Other embodiments of the compositions of the invention incorporate particulate forms protective coatings, protease inhibitors or permeation enhancers for various routes of administration, including parenteral, pulmonary, nasal and oral.

Further, as used herein "pharmaceutically acceptable carrier" are well known to those skilled in the art and include, but are not limited to, 0.01-0.1 M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.,* 1984, Benjamin/Cummings: Menlo Park, Calif., p. 384). Often, a primary challenge with an antigen alone, in the absence of an adjuvant, will fail to elicit a humoral or cellular immune response. Adjuvant include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (*bacille Calmette-Guerin*) and *Corynebacterium parvum*. Preferably, the adjuvant is pharmaceutically acceptable.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

When administered, compounds are often cleared rapidly from mucosal surfaces or the circulation and may therefore elicit relatively short-lived pharmacological activity. Consequently, frequent administrations of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Dosages. The sufficient amount may include but is not limited to from about 1 µg/kg to about 1000 mg/kg. The amount may be 10 mg/kg. The pharmaceutically acceptable form of the composition includes a pharmaceutically acceptable carrier.

The preparation of therapeutic compositions which contain an active component is well understood in the art. Typically, such compositions are prepared as an aerosol of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

An active component can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight.

According to the invention, the component or components of a therapeutic composition of the invention may be introduced parenterally, transmucosally, e.g., orally, nasally, pulmonarailly, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. Oral or pulmonary delivery may be preferred to activate mucosal immunity; since pneumococci generally colonize the nasopharyngeal and pulmonary mucosa, mucosal immunity may be a particularly effective preventive treatment. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

In another embodiment, the active compound can be delivered in a vesicle, in particular a liposome (see Langer (1990) *Science* 249:1527-1533; Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 317-327; see generally ibid).

In yet another embodiment, the therapeutic compound can be delivered in a controlled release system. For example, the polypeptide may be administered using intravenous infusion, an implantable osmotic pump, a transdermal patch, liposomes, or other modes of administration. In one embodiment, a pump may be used (see Langer, supra; Sefton (1987) *CRC Crit. Ref. Biomed. Eng.* 14:201; Buchwald et al. (1980) *Surgery* 88:507; Saudek et al. (1989) *N. Engl. J. Med.* 321:574). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas (1983) *J. Macromol. Sci. Rev. Macromol. Chem.* 23:61; see also Levy et al. (1985) *Science* 228:190; During et al. (1989) *Ann. Neurol.* 25:351; Howard et al. (1989) *J. Neurosurg.* 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Preferably, a controlled release device is introduced into a subject in proximity of the site of inappropriate immune activation or a tumor. Other controlled release systems are discussed in the review by Langer (1990) *Science* 249:1527-1533.

A subject in whom administration of an active component as set forth above is an effective therapeutic regimen for a bacterial infection is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use.

In the therapeutic methods and compositions of the invention, a therapeutically effective dosage of the active component is provided. A therapeutically effective dosage can be determined by the ordinary skilled medical worker based on patient characteristics (age, weight, sex, condition, complications, other diseases, etc.), as is well known in the art. Furthermore, as further routine studies are conducted, more specific information will emerge regarding appropriate dosage levels for treatment of various conditions in various patients, and the ordinary skilled worker, considering the therapeutic context, age and general health of the recipient, is able to ascertain proper dosing. Generally, for intravenous injection or infusion, dosage may be lower than for intraperitoneal, intramuscular, or other route of administration. The dosing schedule may vary, depending on the circulation half-life, and the formulation used. The compositions are administered in a manner compatible with the dosage formulation in the therapeutically effective amount. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Administration with other compounds. For treatment of a bacterial infection, one may administer the present active component in conjunction with one or more pharmaceutical compositions used for treating bacterial infection, including but not limited to (1) antibiotics; (2) soluble carbohydrate inhibitors of bacterial adhesin; (3) other small molecule inhibitors of bacterial adhesin; (4) inhibitors of bacterial metabolism, transport, or transformation; (5) stimulators of bacterial lysis, or (6) anti-bacterial antibodies or vaccines directed at other bacterial antigens. Other potential active components include anti-inflammatory agents, such as steroids and non-steroidal anti-inflammatory drugs. Administration may be simultaneous (for example, administration of a mixture of the present active component and an antibiotic), or may be in seriatim.

Thus, in a specific instance where it is desired to reduce or inhibit the infection resulting from a bacterium mediated binding of bacteria to a host cell, or an antibody thereto, or a ligand thereof or an antibody to that ligand, the polypeptide is introduced to block the interaction of the bacteria with the host cell.

Also contemplated herein is pulmonary or intranasal delivery of the present polypeptide (or derivatives thereof), of the invention. The polypeptide (or derivative) is delivered to the lungs of a mammal, where it can interfere with bacterial, i.e., streptococcal, and preferably pneumococcal binding to host cells. Other reports of preparation of proteins for pulmonary delivery are found in the art [Adjei et al. (1990) *Pharmaceu-* tical Research, 7:565-569; Adjei et al. (1990) International Journal of Pharmaceutics, 63:135-144 (leuprolide acetate); Braquet et al. (1989) Journal of Cardiovascular Pharmacology, 13 (suppl. 5):143-146 (endothelin-1); Hubbard et al. (1989) Annals of Internal Medicine, Vol. III, pp. 206-212 (α1-antitrypsin); Smith et al. (1989) J. Clin. Invest. 84:1145-1146 (α-1-proteinase); Oswein et al., "Aerosolization of Proteins", Proceedings of Symposium on Respiratory Drug Delivery II, Keystone, Colo., March, (1990) (recombinant human growth hormone); Debs et al. (1988) J. Immunol. 140:3482-3488 (interferon-γ and tumor necrosis factor alpha); Platz et al., U.S. Pat. No. 5,284,656 (granulocyte colony stimulating factor)]. A method and composition for pulmonary delivery of drugs is described in U.S. Pat. No. 5,451,569, issued Sep. 19, 1995 to Wong et al.

All such devices require the use of formulations suitable for the dispensing of a polypeptide of the invention (or derivative). Typically, each formulation is specific to the type of device employed and may involve the use of an appropriate propellant material, in addition to the usual diluents, adjuvant and/or carriers useful in therapy. Also, the use of liposomes, microcapsules or microspheres, inclusion complexes, or other types of carriers is contemplated. Chemically modified $R2_1$ or $R2_2$ loop polypeptides may also be prepared in different formulations depending on the type of chemical modification or the type of device employed.

Formulations suitable for use with a nebulizer, either jet or ultrasonic, will typically comprise at least one $R2_1$ or $R2_2$ loop polypeptide (or derivative) dissolved in water at a concentration of about 0.1 to 25 mg of biologically active $R2_1$ or $R2_2$ loop polypeptide per ml of solution. The formulation may also include a buffer and a simple sugar (e.g., for stabilization and regulation of osmotic pressure). The nebulizer formulation may also contain a surfactant, to reduce or prevent surface induced aggregation of the polypeptide caused by atomization of the solution in forming the aerosol.

Formulations for use with a metered-dose inhaler device will generally comprise a finely divided powder containing the $R2_1$ or $R2_2$ loop polypeptide (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

The liquid aerosol formulations contain a polypeptide of the invention and a dispersing agent in a physiologically acceptable diluent. The dry powder aerosol formulations of the present invention consist of a finely divided solid form of a polypeptide of the invention and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The term "aerosol particle" is used herein to describe the liquid or solid particle suitable for nasal or pulmonary administration, i.e., that will reach the mucous membranes. Other considerations, such as construction of the delivery device, additional components in the formulation, and particle characteristics are important. These aspects of pulmonary administration of a drug are well known in the art, and manipulation of formulations, aerosolization means and construction of a delivery device require at most routine experimentation by one of ordinary skill in the art. In a particular embodiment, the mass median dynamic diameter will be 5 micrometers or less in order to ensure that the drug particles reach the lung alveoli [Wearley, L. L. (1991) Crit. Rev. in Ther. Drug Carrier Systems 8:333].

Systems of aerosol delivery, such as the pressurized metered dose inhaler and the dry powder inhaler are disclosed in Newman, S. P., Aerosols and the Lung, Clarke, S. W. and Davia, D. editors, pp. 197-22 and can be used in connection with the present invention.

In a further embodiment, as discussed in detail infra, an aerosol formulation of the present invention can include other therapeutically or pharmacologically active ingredients in addition to an $R2_1$ or $R2_2$ loop polypeptide, such as but not limited to an antibiotic, a steroid, a non-steroidal anti-inflammatory drug, etc.

Liquid Aerosol Formulations. The present invention provides aerosol formulations and dosage forms for use in treating subjects suffering from bacterial, e.g., streptococcal, in particularly pneumococcal, infection. In general such dosage forms contain at least one $R2_1$ and/or $R2_2$ loop polypeptide in a pharmaceutically acceptable diluent. Pharmaceutically acceptable diluents include but are not limited to sterile water, saline, buffered saline, dextrose solution, and the like. In a specific embodiment, a diluent that may be used in the present invention or the pharmaceutical formulation of the present invention is phosphate buffered saline, or a buffered saline solution generally between the pH 7.0-8.0 range, or water.

The liquid aerosol formulation of the present invention may include, as optional ingredients, pharmaceutically acceptable carriers, diluents, solubilizing or emulsifying agents, surfactants and excipients. The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for pH maintenance, solution stabilization, or for the regulation of osmotic pressure. Examples of the agents include but are not limited to salts, such as sodium chloride, or potassium chloride, and carbohydrates, such as glucose, galactose or mannose, and the like.

The present invention further contemplates liquid aerosol formulations comprising at least one $R2_1$ and/or $R2_2$ loop polypeptide and another therapeutically effective drug, such as an antibiotic, a steroid, a non-steroidal anti-inflammatory drug, etc.

Aerosol Dry Powder Formulations. It is also contemplated that the present aerosol formulation can be prepared as a dry powder formulation comprising a finely divided powder form of $R2_1$ or $R2_2$ loop polypeptides and a dispersant.

Formulations for dispensing from a powder inhaler device will comprise a finely divided dry powder containing at least one $R2_1$ and/or $R2_2$ loop polypeptide (or derivative) and may also include a bulking agent, such as lactose, sorbitol, sucrose, or mannitol in amounts which facilitate dispersal of the powder from the device, e.g., 50 to 90% by weight of the formulation. The polypeptide (or derivative) should most advantageously be prepared in particulate form with an average particle size of less than 10 mm (or microns), most preferably 0.5 to 5 mm, for most effective delivery to the distal lung. In another embodiment, the dry powder formulation can comprise a finely divided dry powder containing an $R2_1$ and/or $R2_2$ loop polypeptide, a dispersing agent and also a bulking agent. Bulking agents useful in conjunction with the present formulation include such agents as lactose, sorbitol, sucrose, or mannitol, in amounts that facilitate the dispersal of the powder from the device.

The present invention further contemplates dry powder formulations comprising at least one $R2_1$ and/or $R2_2$ loop polypeptide and another therapeutically effective drug, such as an antibiotic, a steroid, a non-steroidal anti-inflammatory drug, etc.

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include the component or components (or chemically modified forms thereof) and inert ingredients which allow for protection against the stomach environment, and release of the biologically active material in the intestine.

Also specifically contemplated are oral dosage forms of the above derivatized component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis (1981) "Soluble Polymer-Enzyme Abducts" In: *Enzymes as Drugs*, Hocenberg and Roberts, eds., Wiley-Interscience, New York, N.Y., pp. 367-383; Newmark, et al. (1982) *J. Appl. Biochem.* 4:185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the protein (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The peptide therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextran and starch. Certain inorganic salts may be also be used as fillers including calcium triphosphate, magnesium carbonate and sodium chloride. Some commercially available diluents are FAST-FLO® (spray dried lactose α-monohydrate), EMDEX®(dextrates), STA-RX 1500® (corn starch NF), EMCOMPRESS® (calcium hydrogen phosphate dehydrate) and AVICELL® (microcrystalline cellulose).

Disintegrants may be included in the formulation of the therapeutic into a solid dosage form. Materials used as disintegrates include but are not limited to starch, including the commercial disintegrant based on starch, EXPLOTAB®(sodium starch glycolate). Sodium starch glycolate, AMBERLITE™ (polacrilin potassium NF), sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants. Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, CARBOWAX™ Polyethylene Glycol (PEG) 4000 (Product No. CAS # 25322-68-3; CTFA nomenclature PEG-90) and 6000 (CFTA nomenclature PEG 160).

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the polypeptide (or derivative) are for instance the fatty acids oleic acid, linoleic acid and linolenic acid.

Pulmonary Delivery. Also contemplated herein is pulmonary delivery of the present polypeptide (or derivatives thereof). The polypeptide (or derivative) is delivered to the lungs of a mammal while inhaling and coats the mucosal surface of the alveoli. Other reports of this include Adjei et al. (1990) *Pharmaceutical Research* 7:565-569; Adjei et al. (1990) *International Journal of Pharmaceutics* 63:135-144 (leuprolide acetate); Braquet et al. (1989) *Journal of Cardiovascular Pharmacology* 13 (suppl. 5):143-146 (endothelin-1); Hubbard et al. (1989) *Annals of Internal Medicine* Vol. III, pp. 206-212 (a1-antitrypsin); Smith et al. (1989) *J. Clin. Invest.* 84:1145-1146 (a-1-proteinase); Oswein et al. (1990) "Aerosolization of Proteins", Proceedings of Symposium on Respiratory Drug Delivery II, Keystone, Colo., March, (recombinant human growth hormone); Debs et al. (1988) *J. Immunol.* 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Formulations suitable for use with a nebulizer, either jet or ultrasonic, will typically comprise polypeptide (or derivative) dissolved in water at a concentration of about 0.1 to 25 mg of biologically active protein per ml of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the polypeptide (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing polypeptide (or derivative) and may also include a bulking agent, such as lactose, sorbitol, sucrose, or mannitol in amounts which facilitate dispersal of the powder from the device, e.g., 50 to 90% by weight of the formulation. The protein (or derivative) should most advantageously be prepared in particulate form with an average particle size of less than 10 mm (or microns), most preferably 0.5 to 5 mm, for most effective delivery to the distal lung.

Nasal Delivery. Nasal or nasopharyngeal delivery of the polypeptide (or derivative) is also contemplated. Nasal delivery allows the passage of the polypeptide directly over the upper respiratory tract mucosal after administering the therapeutic product to the nose, without the necessity for deposition of the product in the lung. Formulations for nasal delivery include those with dextran or cyclodextran.

The article "a" and "an" are used herein to refer to one or more than one (i.e., to at least one) of the grammatical object of the article. By way of example, "an element" means one or more element.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

The following examples are provided by way of illustration, not by way of limitation.

EXPERIMENTAL

Example 1

Preparation of $R2_1$ and $R2_2$ Cysteine Mutant Polypeptide Constructs

Construction of $R2_1$ and $R2_2$ Cysteine Mutant Polypeptide Constructs

Two truncates of the R2 domain of CbpA R2 from the Tigr4 strain of *S. pneumoniae* were cloned into pET28a vector (Novagen) at the NdeI/EcoRI site. The first truncate (CbpA-$mR2_1$/Cys) expressed amino acids 329-391 (SEQ ID NO:15), which includes helices 1 and 2 of the folded structure and includes the sIgA binding site. Mutations were made at amino acids 333 and 386 changing valine and lysine, respectively, to cysteine residues. The primers used for mutagenensis were:

```
                                         (SEQ ID NO: 45)
V333C: CCTGAAACCAGAAAAAAAGTGTGCAGAAGCTGAGAAGAAGG (SEQ ID NO: 46)
K386C: GCGGAGCTTGAACTAGTATGTGAGGAAGCTAAGGAACC
```

The second truncate (CbpA-$mR2_2$/Cys) expressed amino acids 361-443 (SEQ ID NO:17), which includes helices 2 and 3 of the folded structure and includes the potential laminin receptor binding site. Mutations were made at amino acid positions 364 and 439 changing lysine and valine, respectively to cysteine residues. The primers used for mutagenesis were:

```
                                          (SEQ ID NO: 47)
K364C: CATATGAATACTTACTGCACGCTTGAACTTGAAATTGCTG (SEQ ID NO: 48)
V439C: GCAGCAGAAGAAGATAAATGCAAAGAAAAACCATAAGAATTC
```

The cysteine mutations were introduced to ensure proper folding of the helices into a hairpin conformation. The QUIK-SITE® directed mutagenesis kit (Stratagene) (see Stratagene Catalog, #20051 was used to make the mutations. Clones were screened by sequencing and analyzed for presence of both Cys mutations.

Protein Expression and Purification

DNA for CbpA mR2$_1$/Cys and CbpA-mR2$_2$/Cys were transformed into BL21(DE3) competent cells and grown overnight on LB/Kan (25 µg/ml) agar plates. The amino acid sequences for the CbpA mR2$_1$/Cys and CbpA-mR2$_2$/Cys constructs are set forth in SEQ ID NO:15 and 17, respectively. The nucleotide sequences for the CbpA mR2$_1$/Cys and CbpA-mR2$_2$/Cys constructs are set forth in SEQ ID NO:16 and 18, respectively.

A liquid culture in LB/Kan media was inoculated and grown shaking overnight at 37° C. The overnight culture was diluted 1:20 in fresh media and grown shaking at 37° C. until OD600=0.5-0.7. The culture was induced with 0.07 mM IPTG overnight at 22° C. Once pelleted, the soluble fraction of protein was extracted with BUGUSTER HT™ (Novagen)(a proprietary formulation which utilizes a mixture of non-ionic detergents that is capable of cell wall perforation without denaturing soluble protein plus benzonase nuclease). The soluble fraction was purified over a His-select Ni++ column (Sigma) and eluted with 250 mM imidazole. The protein was dialyzed overnight in PBS and stored at −80° C.

Example 2

Immunogenicity and Protection Studies Using R2$_1$ and R2$_2$ Cysteine Mutant Polypeptides Constructs Nine recombinant constructs were designed to express different regions of the CbpA N-terminus from the S. pneumoniae Tigr4 strain, particularly from the R2 domain.

```
Tigr4 CbpA amino acids 329-443 (R2 DOMAIN)
                                           (SEQ ID NO: 5)
PEKKVAEAEKKVEEAKKKAEDQKEEDRRNYPTNTYKTLELEIAESDVEVK

KAELELVKEEAKEPRNEEKVKQAKAEVESKKAEATRLEKIKTDRKKAEEE

AKRKAAEEDKVKEKP
```

The constructs used were as follows:

| Immunogen | CbpA amino acids |
|---|---|
| CbpA-AR12 | 39-510 (SEQ ID NO: 3) |
| CbpA-R2 | 329-443 (SEQ ID NO: 5) |
| CbpA-mR2$_1$ | 329-391 (SEQ ID NO: 7) |
| CbpA-mR2$_2$ | 361-443 (SEQ ID NO: 9) |
| CbpA-mR2$_1$ & mR2$_2$ | mixed together but not physically linked |
| CbpA-mR2$_1$/Cys | 329-391/V333C, K386C (SEQ ID NO: 15) |
| CbpA-mR2$_2$/Cys | 361-443/K364C, V439C (SEQ ID NO: 17) |
| CbpA-mR2$_1$ & mR2$_2$/Cys | mixed together but not physically linked |
| BSA (—) | |

A schematic representation of the R2 domain and the CbpA-mR2$_1$/Cys and CbpA-mR2$_2$/Cys constructs is provided in FIG. 1.

Immunogenicity of the Constructs

Three groups of 6 Balb/C mice (6-week old females) were immunized with recombinant protein (100 µg) in combination with Complete Freund's Adjuvant using 1 of 3 routes of immunization: intramuscular (IM), intraperitoneal (IP), or subcutaneous (SC). Mice were boosted twice on days 14 and 28. 7 days after each injection, mice were bled and serum IgG titers against full length CbpA were measured by ELISA. The mean IgG titers after the second booster are provided in FIG. 2. The data obtained in this study support excellent immunogenicity of the cysteine mutant constructs because they induced anti-CbpA antibody levels equivalent to the full length N-terminus CbpA-AR12 and the ummodified CbpA-R2 constructs.

Protection Studies

Figure 4:
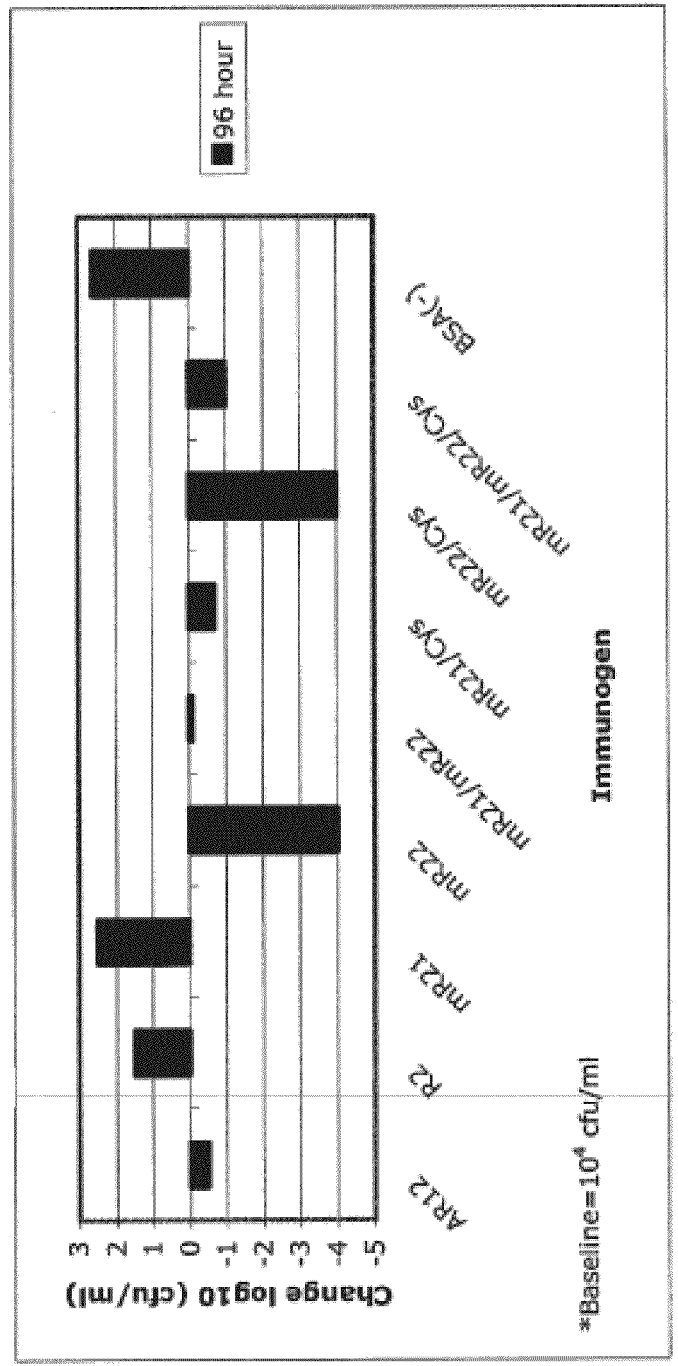
FIG. 4 provides a summary of the change in blood titers (CFU/ml) 96 hours post-infection with S. pneumoniae in mice immunized intramuscularly with the polypeptide constructs of Example 2. Additional experimental details are provided in Example 2.

Eight days after the third injection, mice were challenged intranasally with $10^7$ CFU live Tigr4 S. pneumoniae. 24-hours post-infection, colonization was verified by nasal washes and again at 96 hours for the mice that were still alive. Blood titers were determined every 24 hours for 3 days. For the mice immunized 1M, the 3 mice per group showing either signs of meningitis or severe disease were sacrificed at 48 hours to determine CSF titres. The remaining mice were sacrificed at 96 hours and CSF titers determined. The mice immunized IP were monitored by Xenogen imaging for course of disease with the endpoint being survival. Colonization and blood titer data for both IM and IP injected mice are presented in FIGS. 4-5.

Summary of Results

Mice immunized with the following constructs demonstrated the lowest titers of bacteria in blood in both IM and IP vaccinated mice:

CbpA-mR2$_2$/Cys

CbpA-mR2$_1$ & mR2$_2$/Cys

CbpA-mR2$_1$/Cys

The mice in groups CbpA-mR2$_2$ and CbpA-mR2$_2$/Cys appeared healthy at the time of sacrifice as can be seen by the low blood titers at 96 hours.

In experiment 2 with IP vaccination, survival was also followed. 50% of the BSA controls were dead by day 3. For the R2, mR2$_1$/mR2$_2$, and mR2$_2$Cys constructs, 50% survival was extended to day 4 and 33% survived beyond day 7. The results demonstrate protective immunity induced by these constructs, particularly by the mR2$_2$/Cys construct.

Example 3

Figure 6:
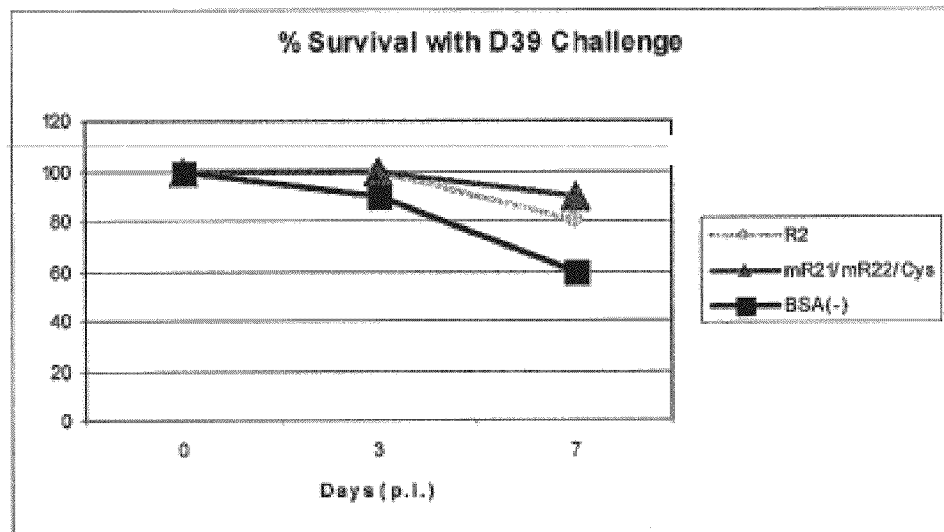
FIG. 6 provides the 7-day survival data of mice immunized with the CbpA R2 domain, a combination of the $mR2_1$/Cys and $mR2_2$/Cys polypeptides, or BSA (negative control) and then challenged with various serotypes of S. pneumoniae. The results obtained with the D39, T4x, 6B, and 19F serotypes are presented in A, B, C, and D, respectively. Additional experimental details are provided in Example 3.
Figure 7:
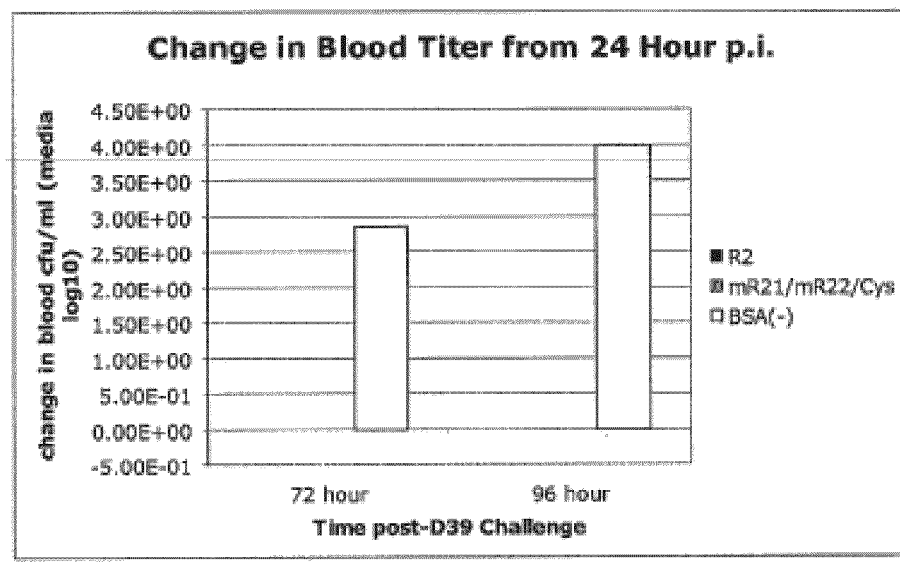
FIG. 7 presents a summary of the change in blood titers (CFU/ml) observed with mice immunized with the CbpA R2 domain, a combination of the $mR2_1$/Cys and $mR2_2$/Cys polypeptides, or BSA (negative control) and then challenged with various serotypes of S. pneumoniae. The results obtained 48, 72, or 96 hours post-infection with the D39, T4x, 6B, and 19F serotypes are presented in A, B, C, and D, respectively. Additional experimental details are provided in Example 3.
Figure 1:
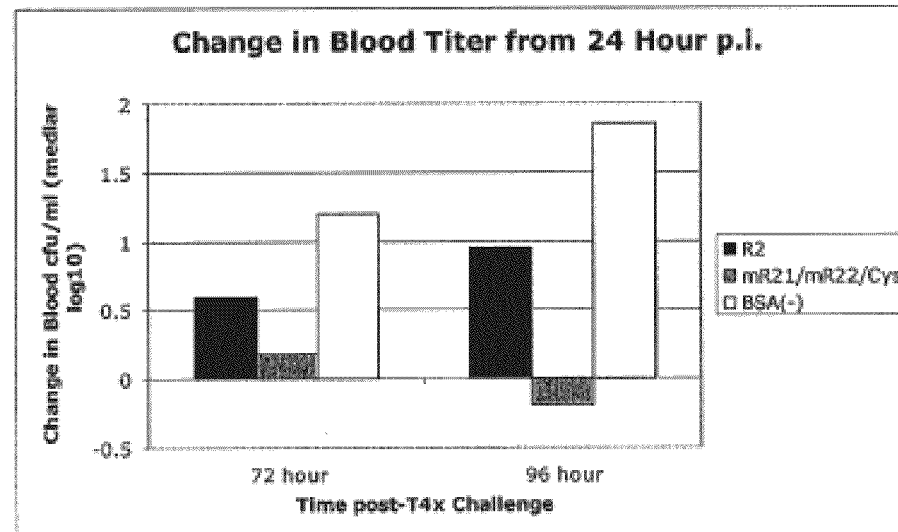
Figure 7:
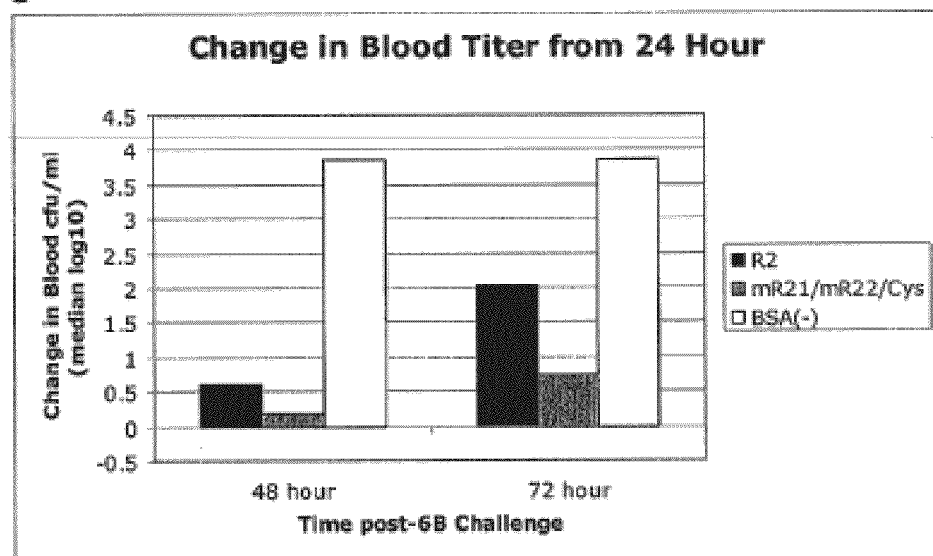
Figure 2:
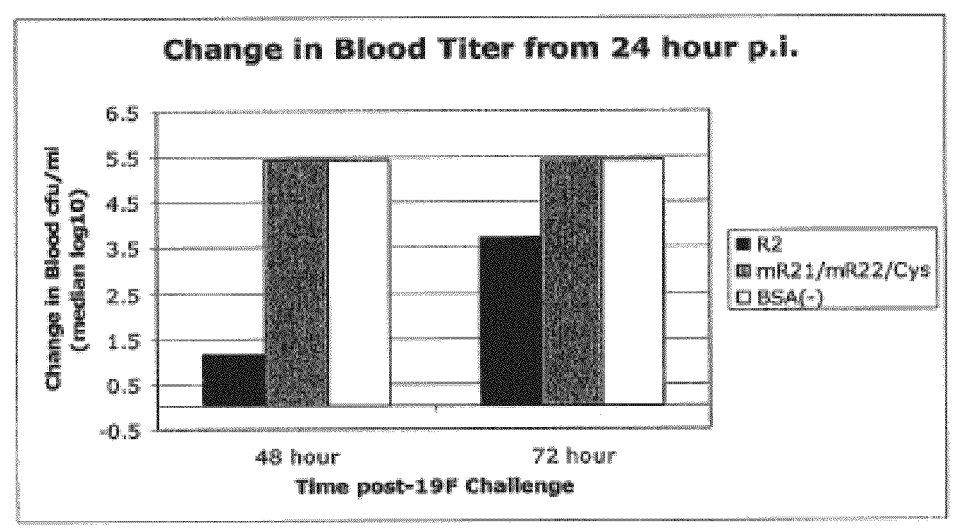

Survival Studies with Mice Vaccinated with R2$_1$ and R2$_2$ Cysteine Mutant Polypeptides The survival rates of mice vaccinated with R2$_1$ and R2$_2$ cysteine mutant polypeptides and then challenged with different S. pneumoniae serotypes (i.e, D39, T4x, 6B, and 19F) were investigated. Specifically, three groups of 30 Balb/C female mice 6 weeks of age were immunized (IP) with 100 µg recombinant R2, R2$_1$ Cys/R2$_2$Cys, or BSA (n=10) in combination with Complete Freund's adjuvant. Mice were boosted with 100 µg protein in combination with Freund's Incomplete Adjuvant at days 14 and 28 of initial priming. Mice were bled at subsequent times throughout the immunization, and IgG titers were analyzed by ELISA before challenge. Mice were challenged with D39 ($1\times10^7$ CFU intranasally), 6B ($1\times10^7$ CFU IP), or 19F ($1\times10^7$ CFU IP). Blood titers were analyzed each day for 3 days and survival was monitored. Mice immunized with R2 or R2₁ Cys/R2₂Cys were both protected from pneumococal disease and death when challenged with D39 and 6B as seen in FIGS. 6 and 7. All mice infected with serotype 19F ultimately died from pneumococcal disease, but the rate was decreased in comparison to the BSA control group.

Results

The results of the survival studies are presented graphically in FIG. 6. A summary of blood titer data is presented in FIG. 7. Notably, the amino acid sequences for the native CbpAs from the various serotypes of the strains used to challenge the mice are significantly different from each other. Thus, the observation that cross-protection is obtained using the vaccine of the invention strongly suggests that the hairpin loop structure may be key to the protective effects.

Example 4

Design of Short Synthetic Peptides for *S. pneumoniae* Vaccination

The sequence of amino acids 361-443 which is represented in construct CbpA-mR2₂ has been shown in the experiment above to induce an immune response that is protective in terms of bacterial counts in the blood, CSF counts, and survival after challenge with live bacteria. This sequence was used as a lead sequence for the design of short synthetic peptides that are between 30 and 45 amino acids in length.

Synthetic peptides were made to two regions: (1) for the CbpA-mR2₁ domain (pIgR binding; colonization of the nasopharynx; R2₁ consensus sequence RRYNPT (SEQ ID NO:11)) and (2) for the CbpA-mR2₂ (laminin receptor; R2₂ consensus sequence EPRNEEK (SEQ ID NO:13)).

Polypeptides comprising the pIgR binding site flanked by either twelve or twenty amino acids on each side were synthesized. Polypeptides corresponding to these sequences were made in parallel but were folded into the desired loop conformation by either 1) formation of a synthetic linkage between a first and a second amino acid present in the polypeptide or 2) engineering the sequences to comprise at least a first and a second cysteine residue to create a disulfide bridge. These polypeptides are presented below in Table 1.

An alignment of the Tigr4 CbpA sequence with other pneumococcal strains expressing the CbpA protein revealed a conserved domain (EPRNEEK (SEQ ID NO:13)) at the "turn" of the CbpA-mR2₂ region. Synthetic peptides were made encompassing this sequence flanked by 12-20 adjacent amino acids. Polypeptides corresponding to these sequences were again made in parallel but were folded into the desired loop conformation by either 1) formation of a synthetic linkage between a first and a second amino acid present in the polypeptide or 2) engineering the sequences to comprise at least a first and a second cysteine residue to create a disulfide bridge.

In order to enhance immune response to the polypeptides of the invention upon vaccination, polypeptides corresponding to NYPTsCys and NEEKsCys, as described below in Table 1, were synthesized with an N-terminal T cell epitope recognition sequence (QYIKANSKFIGITGG; SEQ ID NO:49, corresponding to the minimal functional T-cell epitope plus a glycine-glycine linker). Disulfide bridges were created by the incorporation of cysteine residues in these polypeptides to ensure proper folding. Three polypeptides were also synthesized as controls: 1) a 30-residue polypeptide corresponding to R2 helix 2 ending with EPRNEEK (SEQ ID NO:13); 2) a 30-residue polypeptide comprising EPRNEEK (SEQ ID NO:13) and 23 amino acid residues of helix 3; and 3) a 30-residue polypeptide corresponding to the carboxy-terminus of R2. All of the polypeptides described above are presented in Table 1.

e 1: Exemplary Polypeptides of the Invention

| Size | Designation | Amino acids | | |
|---|---|---|---|---|
| 30 | NYPTs | 343-372 | AKKKAEDQKEEDRRNYPTNTYKTLELEIAE | (SEQ ID NO: 19) |
| 30 | NYPTs2 | 343-372 | AKKKAEDQKEEDRRNYPYNTYKTLELEIAE | (SEQ ID NO: 19) |
| 30 | NYPTsCys | 343-372 | ACKKAEDQKEEDRRNYPYNTYKTLELCAE | (SEQ ID NO: 21) |
| 46 | NYPT1 | 330-381 | GEKKVAEAKKKAEDQKEEDRRNYPYNTYKTLELEIAESDVEVKKAE | (SEQ ID NO: 23) |
| 46 | nypt2 | 330-381 | GEKKVAEAKKKAEDQKEEDRRNYPYNTYKTLELEIAESDVEVKKAE | (SEQ ID NO: 23) |
| 46 | NYPT1Cys | 330-381 | EKKVAECKKAEDQKEEDRRNYPYNTYKTLELCAESDVEVKKAE | (SEQ ID NO: 25) |
| 30 | NEEKs | 379-408 | KAELELVKEEAKEPRNEEKVKQAKAEVESK | (SEQ ID NO: 27) |
| 30 | neeks2 | 379-408 | KAELELVKEEAKEPRNEEKVKQAKAEVESK | (SEQ ID NO: 27) |
| 30 | NEEKsCys | 379-408 | CELELVKEEAKEPRNEEKVKQAKACESK | (SEQ ID NO: 29) |
| 45 | NEEK1 | 372-416 | GESDVEVKKAELELVKEEAKEPRNEEKVKQAKAEVESKKAEATRLE | (SEQ ID NO: 31) |
| 45 | neek2 | 372-416 | GESDVEVKKAELELVKEEAKEPRNEEKVKQAKAEVESKKAEATRLE | (SEQ ID NO: 31) |
| 45 | NEEK1Cys | 372-416 | ESDVEVCAELELVKEEAKEPRNEEKVKQAKACESKKAEATRLE | (SEQ ID NO: 33) |
| 30 | NEEKnterm | 368-397 | LEIAESDVEVKKAELELVKEEAKEPRNEEK | (SEQ ID NO: 35) |
| 30 | NEEKcterm | 391-420 | EPRNEEKVKQAKAEVESKKAEATRLEKIKT | (SEQ ID NO: 37) |
| 30 | R2cterm | 414-443 | RLEKIKTDRKKAEEEAKRKAAEEDKVKEKP | (SEQ ID NO: 39) |
| 45 | TCENYPTsCys | 343-372 | *QYIKANSKFIGITGGA*CKKAEDQKEEDRRNYPYNTYKTLELCAE | (SEQ ID NO: 41) |
| 45 | TCENEEKsCys | 379-408 | *QYIKANSKFIGITGGK*CELELVKEEAKEPRNEEKVKQAKACESK | (SEQ ID NO: 43) | amino acid residues are used to form synthetic linkages; shaded cysteine residues are incorporated to permit disulfide bond formation. Underlined regions denote desired conserved residues.
| residues represent the linked T cell epitope (TCE) sequence.

The nucleic acid molecules that encode the polypeptides of table 1 are set forth in SEQ ID NOs:20, 22, 24, 26, 28, 30, 32, 34, 36, 38, 40, 42, and 44, respectively. Polypeptides that have been modified to create synthetic linkages between at least a first and a second amino acid residue present in the polypeptide, wherein the synthetic linkage stabilizes the polypeptide in the desired loop conformation, comprise the same amino acid sequence as the linear versions of these polypeptides.

Figure 5:
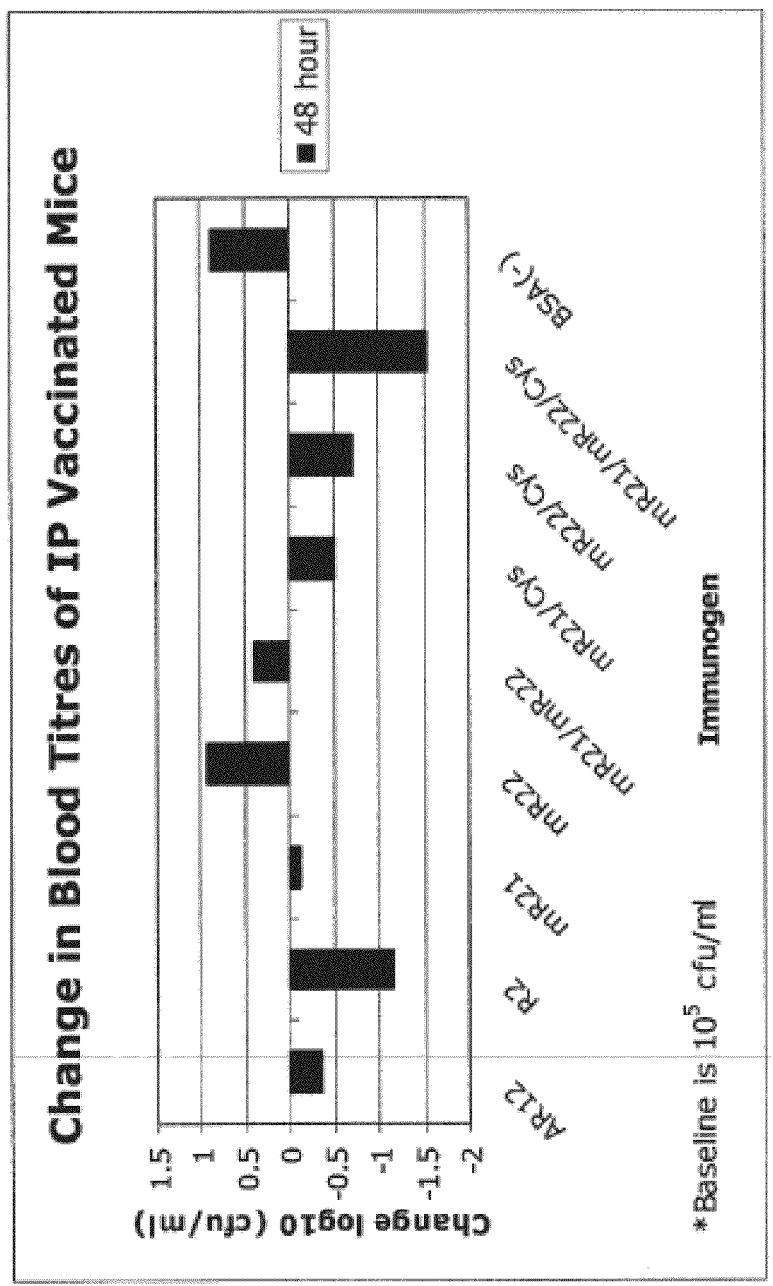
FIG. 5 presents a summary of the change in blood titers (CFU/ml) 48 hours post-infection with S. pneumoniae in mice immunized intraperitoneally with the polypeptide constructs of Example 2. Additional experimental details are provided in Example 2.

The R2₁ and R2₂ polypeptides are tested for immunogenicity and protective activity, as described above in Example 1, to compare the linear and stabilized polypeptides. FIG. 5 shows that linear peptides are not protective whereas the corresponding loop peptides are protective.

Example 5

Immunization of Mice with CbpA-R2₁ and R2₂ Short Sequence Loop Polypeptides

Protocol 6-week old female Balb/C mice were immunized with one of the following peptide/protein groups:
Group 1: CbpA recombinant R2 protein (positive control; SEQ ID NO:5);
Group 2: LSEIK peptide (negative control; SEQ ID NO:55);
Group 3: TCENYPTsCYS peptide representing CbpA R2 loop 1 with a T cell epitope (TCE) sequence (pIg receptor binding site; SEQ ID NO:41);
Group 4: TCENEEKsCYS peptide representing CbpA R2 loop 2 with a TCE sequence (laminin receptor binding site; SEQ ID NO:43); or
Group 5: TCENYPTsCYs (SEQ ID NO:41) and TCENEEKsCYS (SEQ ID NO:43) mixed together.

Specifically, the mice were primed with 100 µg of peptide (or 10 µg of the R2 protein for Group 1) intraperitoneally in Complete Freund's Adjuvant. Booster intraperitoneal injections were administered at weeks 2 and 4 with 100 µg peptide (or 10 µg R2 protein) in Incomplete Freund's Adjuvant. Immunogenicity, nasopharyngeal colonization, bacteremia, and survival were investigated in each group of mice, as described in detail below.

Immunogenicity

Serum was collected from each mouse prior to immunization with the peptide/protein of interest (i.e., a naïve serum sample obtained prior to the prime injection) and after the prime and each booster injection. Serum anti-CbpA IgG titers for each group were analyzed by ELISA using full-length recombinant CbpA protein to coat the ELISA plates. The results are presented in FIG. 8 and summarized below.

Results

Figure 8:
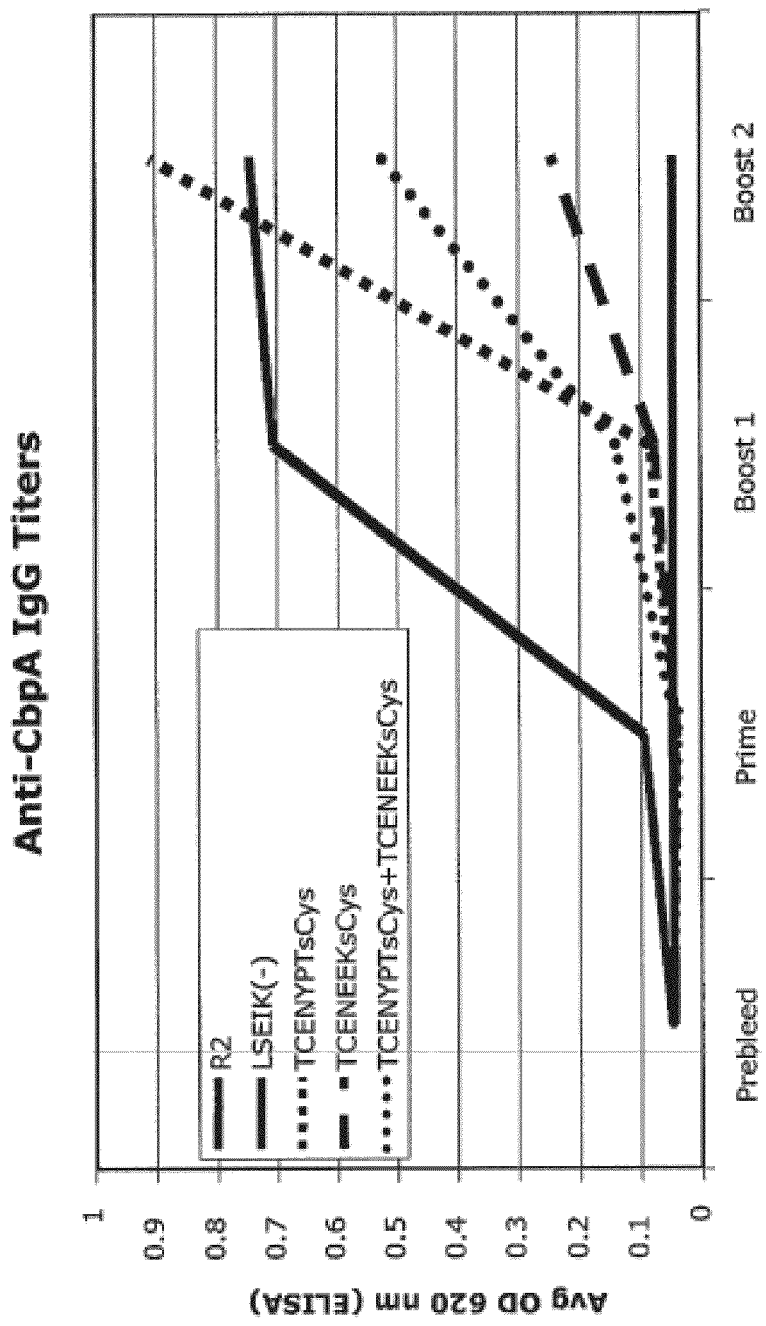
FIG. 8 provides a summary of the anti-CbpA IgG titers of mice immunized with recombinant CbpA R2 protein (positive control), LSEIK peptide (SEQ ID NO:55; negative control), the TCENYPTsCys peptide (SEQ ID NO:41; corresponding to the CbpA $R2_1$ domain and an amino acid sequence for a T cell epitope (TCE)), the TCENEEKsCys peptide (SEQ ID NO:43; corresponding to the CbpA $R2_2$ domain and an amino acid sequence for a TCE), or a combination of the TCENYPTsCys peptide and the TCENEEKsCys peptide. Results at various time points (i.e., pre-bleed, prime, boost 1, and boost 2) are presented. Experimental details are provided in Example 5.

As shown in FIG. 8, the R2 positive control protein had a high anti-CbpA titer after the final boost, while the LSEIK negative control peptide showed no anti-CbpA titer at any point during the study. Titers for the TCENYPTsCys group were higher than those observed with the R2 positive control. The titers for the TCENEEKsCYS group and the combined peptide group (i.e., TCENYPTsCYS and TCENEEKsCYS) were slightly lower than the titers measured for the R2 group.

Analysis of Nasopharyngeal Colonization, Bacteremia, and Survival Rates

At week 10, the mice in each group were challenged intranasally with 6×10⁶ CFU of Tigr4X pneumococci. Nasal lavages and blood from the tail vein were obtained each day after challenge and plated on blood agar plates. Pneumococci were counted the next day, and the log₁₀ CFU/ml for nasopharyngeal colonization and blood were analyzed. Survival rates were also monitored and recorded.

Nasopharyngeal Colonization—Results

Figure 9:
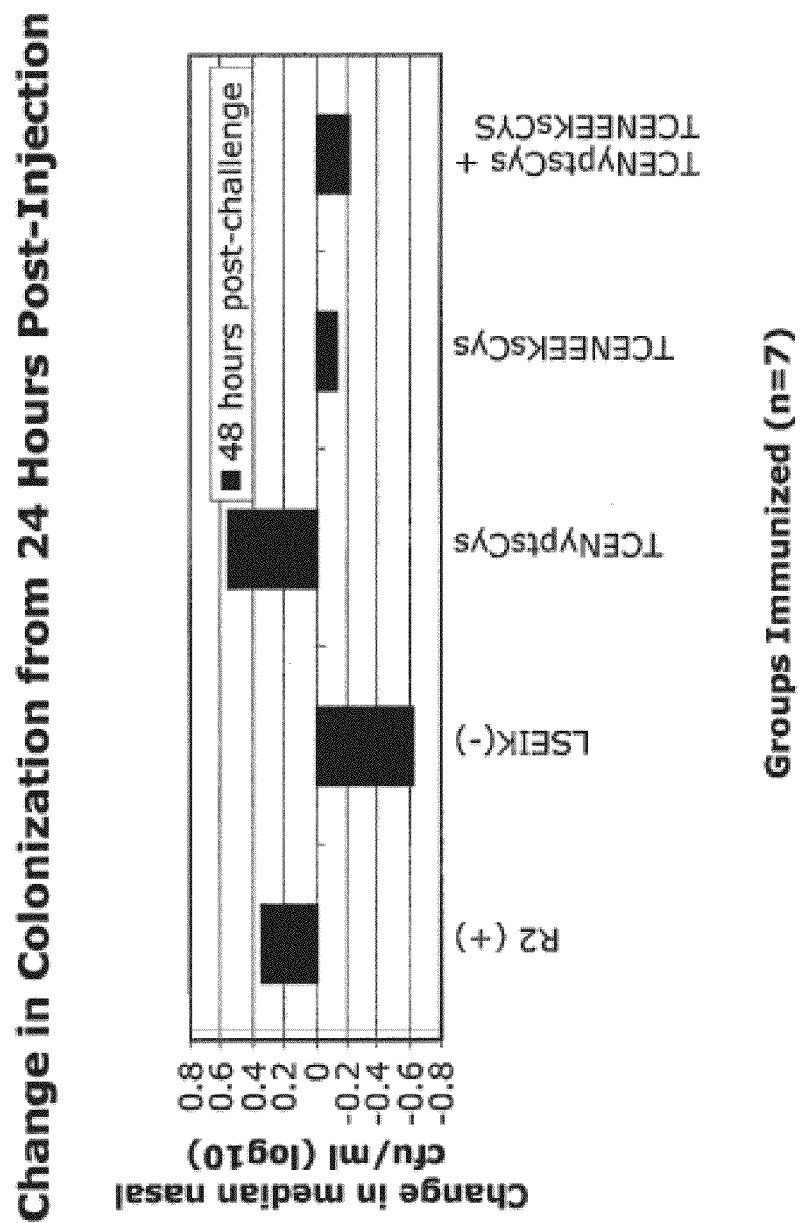
FIG. 9 presents the change in nasopharyngeal colonization at 48 hours post-intranasal challenge with Tigr4X pneumococci in mice immunized with recombinant CbpA R2 protein (positive control), LSEIK peptide (SEQ ID NO:55; negative control), the TCENYPTsCys peptide (SEQ ID NO:41; corresponding to the CbpA $R2_1$ domain and an amino acid sequence for a TCE), the TCENEEKsCys peptide (SEQ ID NO:43; corresponding to the CbpA $R2_2$ domain and an amino acid sequence for a TCE), or a combination of the TCENYPTsCys peptide and the TCENEEKsCys peptide. Experimental details are provided in Example 5.

The results of the nasopharyngeal colonization studies are presented in FIG. 9. The groups immunized with TCENEEKsCYS and the combination of the TCENYPTsCYS+TCENEEKsCYS peptides showed a slight decrease in colonization over the 48 hours post-challenge with Tigr4X pneumococci. The TCENYPTsCYS and R2 protein positive control groups showed an increase in nasopharyngeal colonization over the same time period. Thus the immune response generated by immunization with the TCENEEKsCYS peptide may be active in decreasing nasopharyngeal colonization.

Control of Bacteremia—Results

Figure 10:
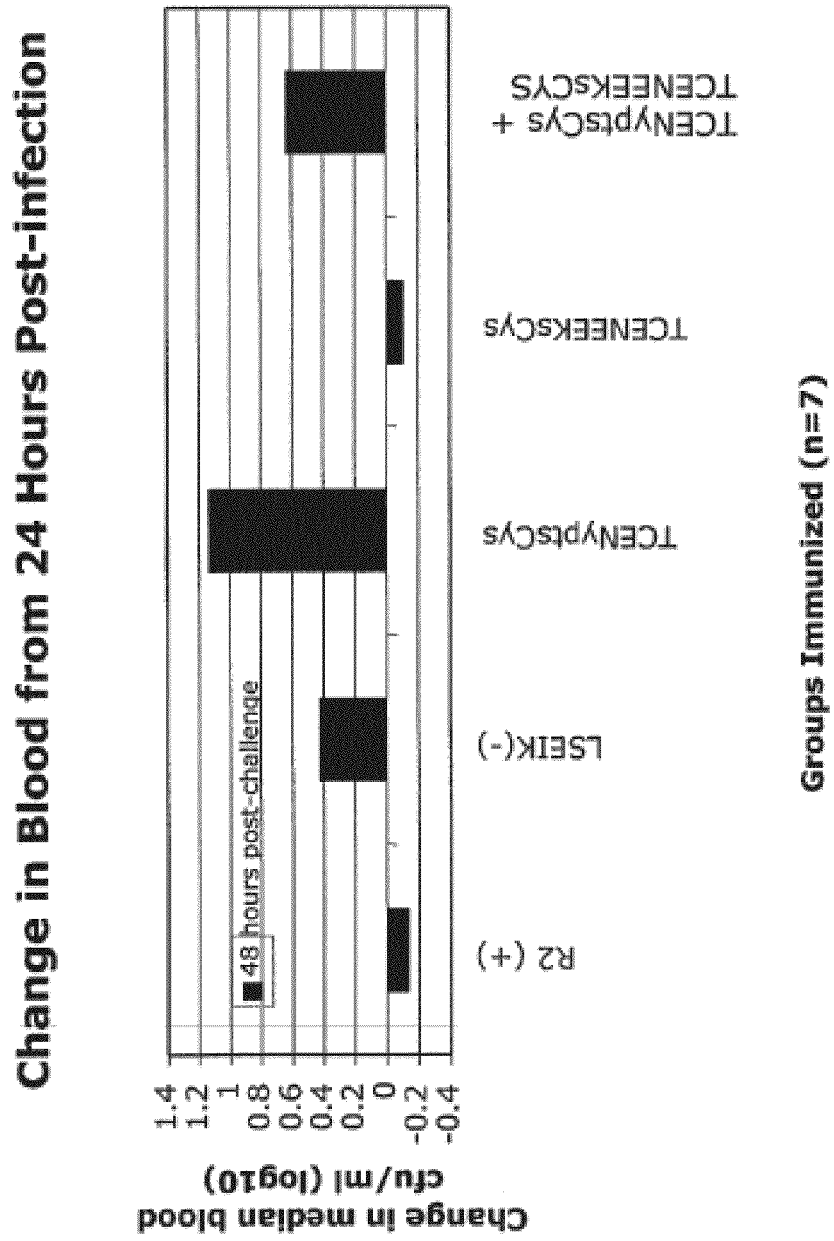
FIG. 10 provides the change in the amount of pneumococci in the blood (CFU/ml) at 48 hours post-intranasal challenge with Tigr4X pneumococci in mice immunized with recombinant CbpA R2 protein (positive control), LSEIK peptide (SEQ ID NO:55; negative control), the TCENYPTsCys peptide (SEQ ID NO:41; corresponding to the CbpA $R2_1$ domain and an amino acid sequence for a TCE), the TCENEEKsCys peptide (SEQ ID NO:43; corresponding to the CbpA $R2_2$ domain and an amino acid sequence for a TCE), or a combination of the TCENYPTsCys peptide and the TCENEEKsCys peptide. Experimental details are provided in Example 5.

The groups immunized with the R2 protein or with the TCENEEKsCYS peptide exhibited a decrease in pneumococci blood titers over the 48 hours post-challenge with Tigr4X pneumococci. All of the remaining groups showed an increased amount of pneumococci in the blood over the same time frame. The results are summarized in FIG. 10.

Survival Studies—Results

Figure 11:
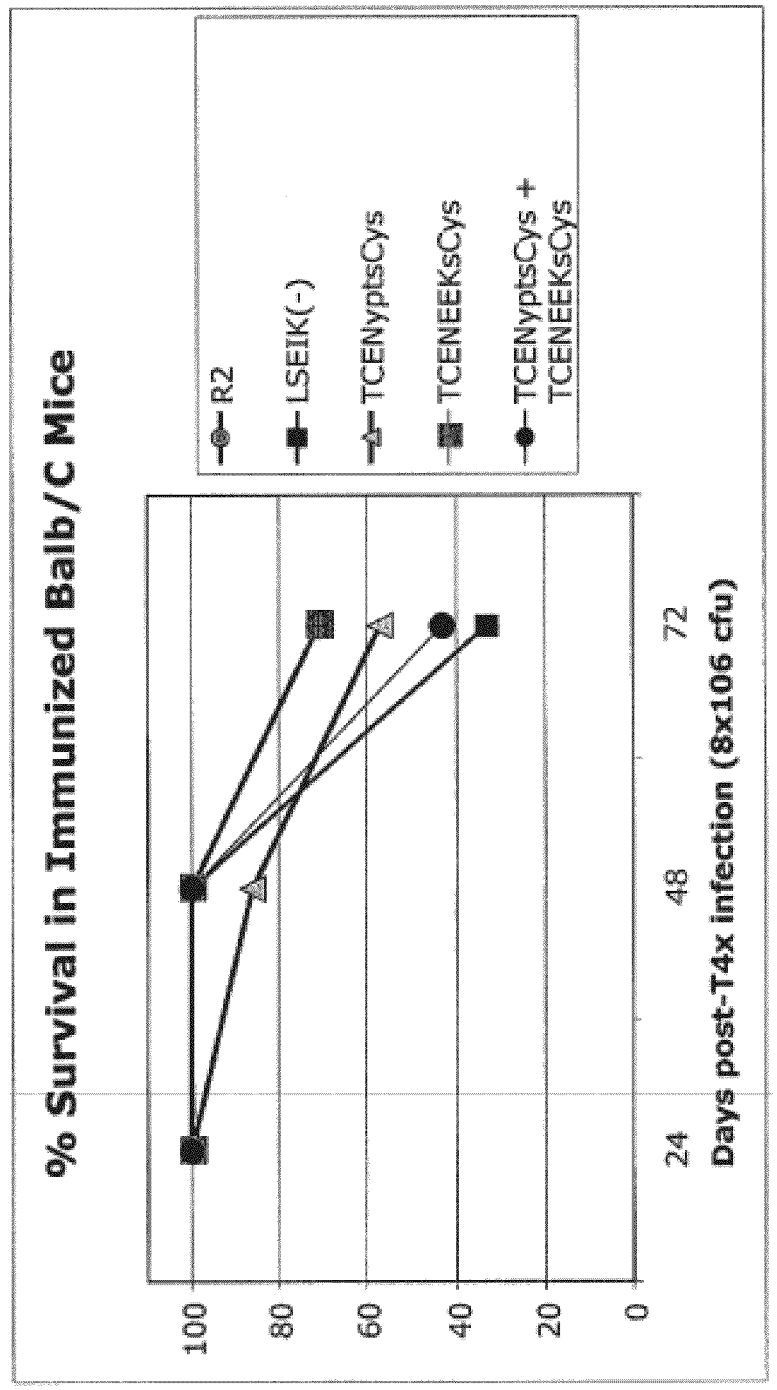
FIG. 11 presents the survival rates of Balb/c mice (at various time points post-infection with Tigr4X pneumococci)

Survival rates for each group of immunized mice were monitored and recorded. The results of the survival studies are summarized in FIG. 11. At 72 hours post-infection with Tigr4X pneumococci, mice immunized with either R2 protein or the TCENEEKsCYS peptide survived better than all other groups (71% survival). The LSEIK peptide negative control group showed a 33% survival. The groups immunized with the TCENYPTsCYS peptide or the combination of the TCENYPTsCYS peptide+the TCENEEKsCYS peptide showed survival rates of 57% and 43%, respectively.

This enhanced survival of the TCENEEKsCYS immunized mice was noted despite only a modest immune response (see the immunogenicity studies above), thereby suggesting a strong protective activity of the TCENEEKsCYS peptide.

Example 6

Design of Additional Short Synthetic Peptides for S. pneumoniae Vaccination

The sequence of amino acids 361-443 which is represented in construct CbpA-mR2₂ has been shown in the experiment above to induce an immune response that is protective in terms of bacterial counts in the blood, CSF counts, and survival after challenge with live bacteria. This sequence was again used as a lead sequence for the design of additional short synthetic peptides that are between 30 and 45 amino acids in length.

Synthetic peptides were again made to two regions: (1) for the CbpA-mR2₁ domain (pIgR binding; colonization of the nasopharynx; R2₁ consensus sequence RRYNPT (SEQ ID NO:11)) and (2) for the CbpA-mR2₂ (laminin receptor; R2₂ consensus sequence EPRNEEK (SEQ ID NO:13)).

Polypeptides comprising the pIgR binding site flanked by either five or twelve amino acids on each side were synthesized. These polypeptides were made to fold into the desired loop conformation by engineering the sequences to comprise at least a first and a second cysteine residue to create a disulfide bridge.

An alignment of the Tigr4 CbpA sequence with other pneumococcal strains expressing the CbpA protein revealed a conserved domain (EPRNEEK (SEQ ID NO:13)) at the "turn" of the CbpA-mR2₂ region. Synthetic peptides were made encompassing this sequence flanked by five to twelve adjacent amino acids. These polypeptides were also made to fold into the desired loop conformation by engineering the sequences to comprise at least a first and a second cysteine residue to create a disulfide bridge. These polypeptides are presented below in Table 2.

In order to enhance immune response to the polypeptides of the invention upon vaccination, polypeptides corresponding to NYPTsCys and NEEKsCys, as described above in Table 1, were synthesized with an C-terminal T cell epitope recognition sequence (QYIKANSKFIGITGG; SEQ ID NO:49, corresponding to the minimal functional T-cell epitope plus a glycine-glycine linker). See Table 2. Polypeptides were also synthesized with an N terminal tandom repeat of this T cell epitope recognition sequence followed by a glycine-glycine linker (QYIKANSKFIGITQYIKAN-SKFIGITGG; SEQ ID NO:65). Disulfide bridges were created by the incorporation of cysteine residues in these polypeptides to ensure proper folding.

In order to enhance immune response to the polypeptides of the invention upon vaccination, polypeptides corresponding to NYPTsCys and NEEKsCys, as described above in Table 1, were synthesized with a second N-terminal or C-terminal T cell epitope recognition sequence (PVVEVNGV-TIQVGSRGG; SEQ ID NO:66, corresponding to the minimal functional T-cell epitope plus a glycine-glycine linker). Disulfide bridges were created by the incorporation of cysteine residues in these polypeptides to ensure proper folding. The polypeptides described above are set forth in Tables 1 and 2.

2: Exemplary Polypeptides of the Invention

| Designation | Amino Acids | | |
|---|---|---|---|
| YPTCtce1 | 343-372 | ACKKAEDQKEED<u>RRNYPTN</u>TYKTLELECAE*ggqyikanskfigit* | (SEQ ID NO: 67) |
| YPTCtce2 | 344-371 | KCKAEDQKEED<u>RRNYPTN</u>TYKTLELECA*ggpvvevngvtiqvgsr* | (SEQ ID NO: 68) |
| YPTCtce3 | 350-366 | *qyikanskfigitqyikanskfigitgg*QCEED<u>RRNYPTN</u>TYKCL | (SEQ ID NO: 69) |
| YPTCtce4 | 344-371 | *pvvevngvtiqvgsrgg*KCKAEDQKEED<u>RRNYPTN</u>TYKTLELECA | (SEQ ID NO: 70) |
| NEEKCtce1 | 379-408 | KCELELVKEEAKEPRNEEKVKQAKAECESK*ggqyikanskfigit* | (SEQ ID NO: 71) |
| NEEKCtce2 | 379-406 | KCELELVKEEAKEPRNEEKVKQAKAECE*ggpvvevngvtiqvgsr* | (SEQ ID NO: 72) |
| NEEKCtce3 | 386-402 | *qyikanskfigitqyikanskfigitgg*KECAKEPRNEEKVKQCK | (SEQ ID NO: 73) |
| NEEKCtce4 | 379-406 | *pvvevngvtiqvgsrgg*KCELELVKEEAKEPRNEEKVKQAKAECE | (SEQ ID NO: 74) |

*Bolded cysteine residues are incorporated to permit disulfide bond formation. Underlined regions denote desired conserved residues. Italicized residues represent the linked T cell epitope (TCE) sequence.

One of skill in the art would appreciate that the polypeptides that have been modified to create synthetic linkages between at least a first and a second amino acid residue present in the polypeptide, wherein the synthetic linkage stabilizes the polypeptide in the desired loop conformation, comprise the same amino acid sequence as the linear versions of these polypeptides.

The polypeptides designed in this study were utilized for the immunization studies of Example 7 below.

Example 7

Immunization of Mice with Additional CbpA-R2$_1$ and R2$_2$ Short Sequence Loop Polypeptides Protocol 6-week old female Balb/C mice were immunized with one of the following peptide/protein groups described above in Example 6:

Group 1: CbpA recombinant R2 protein (positive control; SEQ ID NO:5);

Group 2: YPTCtce4 (peptide representing CbpA R2 loop 1 pIgR receptor binding site and N-terminal TCE sequence (PVVEVNGVTIQVGSRGG; SEQ ID NO:66)); SEQ ID NO:70 for the entire YPTCtce4 peptide.

Group 3: NEEKsCtce3 (peptide representing CbpA R2 loop 2 laminin receptor binding site and two tandem N-terminal TCE sequences (SEQ ID NO:49)); SEQ ID NO:73 for the entire NEEKsCtce3 peptide.

Group 4: NEEKsCtce4 (peptide representing CbpA R2 loop 2 laminin receptor binding site and N-terminal TCE sequence (PVVEVNGVTIQVGSRGG; SEQ ID NO:66)); SEQ ID NO:74 for the entire NEEKsCtce4 peptide.

Group 5: CbpA recombinant R2 protein (positive control; SEQ ID NO:5);

Group 6: YPTCtce4 (peptide representing CbpA R2 loop 1 pIgR receptor binding site and N-terminal TCE sequence (PVVEVNGVTIQVGSRGG; SEQ ID NO:66)); SEQ ID NO:70 for the entire YPTCtce4 peptide.

Group 7: NEEKsCtce3 (peptide representing CbpA R2 loop 2 laminin receptor binding site and two tandem N-terminal TCE sequences (SEQ ID NO:49)); SEQ ID NO:73 for the entire NEEKsCtce3 peptide.

Specifically, the mice were primed with 200 μg of peptide (or 10 μg of the R2 protein for Group 1) intraperitoneally in complete Freund's adjuvant. Booster intraperitoneal injections were administered at weeks 2 and 4 with 200 μg peptide (or 10 μg R2 protein) in incomplete Freund's adjuvant. Groups 1-4 were challenged intranasally with T4X while groups 5-7 were challenged intraperitoneally with T4X. Immunogenicity, nasopharyngeal colonization, bacteremia, and survival were investigated in each group of mice, as described in detail below.

Immunogenicity

Serum was collected from each mouse prior to immunization with the peptide/protein of interest (i.e., a naïve serum sample obtained prior to the prime injection) and after the prime and each booster injection. Serum anti-CbpA IgG titers for each group were analyzed by ELISA using full-length recombinant CbpA protein to coat the ELISA plates. The results are presented in FIG. 12 and summarized below.

Results of Immunogenicity

Immunization with R2 protein, YPTCtce4, or NEEKCtce4 showed high IgG titers against recombinant CbpA by ELISA. Groups immunized with NEEKCtce3 had lower IgG titers, but still significantly higher than the negative control.

Analysis of Nasopharyngeal Colonization, Bacteremia, and Survival Rates

At week 10, the mice in groups 1-4 were challenged intranasally with $1\times10^7$ CFU of Tigr4X pneumococci. Groups 5-7 were challenged intraperitoneally with 50 cfu T4X. Nasal lavages and blood from the tail vein were obtained each day after challenge and plated on blood agar plates. Nasal lavages were not collected on mice challenged intraperitoneally. Pneumococci were counted the next day, and the $\log_{10}$ CFU/ml for nasopharyngeal colonization and blood were analyzed. Survival rates were also monitored and recorded.

Nasopharyngeal Colonization—Results

Mice immunized with YPTCtce4 peptide showed a gradual increase in nasopharyngeal colonization by 2-log units from 24 to 72 hours post infection. Mice immunized with NEEKCtce3 showed protection of colonization by a 0.5-log unit decrease from 24 to 72 hours post-infection.

Control of Bacteremia—Results

Mice challenged intraperitoneally with T4X showed protection from bacteremia when immunized with either R2 control protein or NEEKCtce3 peptide. Mice immunized with R2 or NEEKCtce3 both showed a 1-log unit decrease in blood cfu/ml at 72 hours while the group immunized with YPTCtce4 showed a 3-log unit increase in bacteremia.

Survival Studies—Results

At 72 hours post intranasal infection the group immunized with NeekCtce3 had a survival rate of 83% versus the group immunized with YPTCtce4 which had 17% survival rate. At 72 hours post intraperitoneal infection the R2 control and NeekCtce3 showed 71% and 57% survival, respectively, while the YPTCtce4 group only had 14% survive. Based on the immunization studies, the region of CbpA loop 2 that binds the laminin receptor was determined to be protective against bacteremia, meningitis, and subsequent death.

Example 8

Production of Monoclonal Antibodies Against CbpA Peptides and Passive Protection of Mice using Anti-CbpA Monoclonal Antibodies To substantiate the results of Example 7 with respect to the protection obtained with CbpA loop 2, a passive protection experiment was designed and performed. Specifically, monoclonal antibodies against both loops 1 and 2 were produced.

Proteins were expressed and purified that represented CbpA mR$2_1$C amino acids 329-391/V333C, K386C (pIgR receptor binding site SEQ ID NO:15) and CbpA mR$2_2$C amino acids 361-443/K364C, V439C (laminin receptor binding site SEQ ID NO:17). Both proteins have cysteine residues incorporated into the ends to ensure proper loop folding. The purified proteins were used for monoclonal antibody production. Once cell lines were fused and expanded, supernatants from subclones were analyzed by western blot against a pneumococcal lysate and by ELISA. The positive clones were then injected into mice for ascites production and purified.

Western Blot to Determine Antibody Recognition of CbpA

Initially mouse test bleeds from immunizations were analyzed by western blot to determine which mouse had the highest titers against CbpA. Two mice immunized with mR$2_1$C and three mice immunized with mR$2_2$C were selected for fusion. Supernatants from fused cell lines were subsequently analyzed by western blot for recognition of CbpA in a T4R lysate.

Pneumococcal lysates of wild type Tigr4 were run on a 12% SDS-PAGE gel and transferred to PVDF membrane. The membranes were blocked in 5% milk/PBST for 30 minutes. 1:20 dilution of monoclonal cell line supernatant was added to the milk and incubated at 4C overnight. The blots were washed 4× with PBST and incubated 30 minutes in goat anti-mouse IgG-HRP (horseradish peroxidase) secondary antibody. The blots were again washed and overlayed with chemiluminescent substrate against HRP. The blots were exposed to film and analyzed for recognition of a 112 kD band corresponding to wild type CbpA. The clones that showed a high intensity, low background recognition were further subcloned and expanded. Clones of potential interest were selected for cryopreservation and/or ascites production.

ELISA to Determine Antibody Clone Epitope Specificity

Only one clone against CbpA mR$2_1$C (designated "14A3.G5") was grown and recognized CbpA protein by Western blot analysis. 17 clones against CbpA mR$2_2$C were easily grown and showed high recognition of CbpA by Western blot.

ELISA plates were coated overnight with CbpA polypeptides corresponding to the relevant portions of CbpA-$R_2$. The plates were washed 3× in 1 mM Tris/154 mM NaCl/1% Tween 20 buffer and blocked with 10% FBS for 2 hours. The monoclonal subclone supernatant was diluted in 10% serum to 1:50 dilution and incubated on the plate for 1 hour. The plates were washed 3× and overlayed with anti-mouse IgG-alkaline phosphatase (AP) secondary antibody (1:2000) for 1 hour. The plates were washed 5× and subject to AP Yellow Substrate (Sigma) for 20 minutes. The plates were read at $OD_{405}$ by an ELISA plate reader. Each supernatant was also used against plates coated with full length recombinant CbpA as well as T4R bacteria to ensure recognition of the native folded protein.

Selected clones of interest were injected into mice for ascites production, and monoclonal antibodies were purified and used in the passive protection studies described below.

Passive Protection in BalbC Mice Using Anti-CbpA Monoclonal Antibodies

Protocol 6 week old female BalbC mice were used in a study to assess passive protection from pneumococcal T4X infection utilizing particular anti-CbpA monoclonal antibodies. 7 mice were used for each group. One hour prior to infection, the mice were given 300 µg of the monoclonal antibody intraperitoneally. The mice were infected intranasally with $2 \times 10^7$ cfu of T4X. 18 hours post-infection the mice were given a second dose of 300 µg monoclonal antibody intraperitoneally. The groups in this study were as follows:

| Group | Antibody | CbpA epitope |
|---|---|---|
| 1 | 14A3.G5 | RNYPT loop |
| 2 | 3G12.G11.E8 | EPRNEEK loop |
| 3 | 14A3.G5 + 3G12.G11.E8 | RNYPT/EPRNEEK loops |
| 4 | PBS (negative control) | — |

At 24, 48, and 72 hours nasal lavages and blood from the tail vein were obtained and plated on blood agar plates. After overnight incubation, the pneumococcal colonies were counted and cfu/ml for each mouse was charted. The rate of survival for each group was monitored as well as the rate of meningitis. Mice that developed meningitis were observed by physical attributes (spinning of the head) as well as using the Xenogen imaging machine to identify pneumococcal bacteria in the region of the brain. The results shown are the summary of two independent experiments with identical doses of both antibody and T4X bacteria.

Results of Nasopharyngeal Colonization Protection

Both antibody 14A3.G5 against RNYPT region and the 3G12.G11.E8 antibody against EPRNEEK region (groups 1 and 2) showed an initial decrease in nasopharyngeal colonization from 24 to 48 hours. The results are show in FIG. 13.

Results of Bacteremia Protection

Monoclonal antibody 3G12.G11.E8, which blocks CbpA EPRNEEK (the laminin receptor binding region in the brain) showed significant protection against bacteremia versus mice given PBS only. The results are shown in FIG. 14.

Results of Protection from Meningitis Development

While 70-93% of the mice in groups 1, 3, and 4 developed meningitis within one week post-infection, only 29% of Group 2, which was protected with monoclonal antibody 3G12.G11.E8 that recognizes the CbpA EPRNEEK region, developed meningitis. The results are shown in FIG. 15.

Results of Survival

72% of the mice protected with the monoclonal antibody designated as 3G12.G11.E8 (Group 2) survived. This is statistically significant compared to Groups 1, 3, and 4 which had a 15-29% rate of survival. The results are shown in FIG. 16.

Example 9

Further Immunization Studies in Mice with CbA-R2$_1$ and R2$_2$ Short Sequence Loop Polypeptides Protocol 6-week old female Balb/C mice were immunized with one of the following peptide/protein groups:

Group 1: CbpA recombinant R2 protein (positive control; SEQ ID NO:5);

Group 2: LSEIK peptide (negative control; SEQ ID NO:55);

Group 3: TCENEEKsCys (peptide representing CbpA R2 loop 2 with a T cell epitope (TCE) sequence and laminin receptor binding site); SEQ ID NO:43 for the entire CEN-EEKsCys peptide;

Group 4: NEEKsCtce1 (peptide representing CbpA R2 loop 2 with laminin receptor binding site and a C-terminal TCE sequence (SEQ ID NO: 49); SEQ ID NO:71 for the entire NEEKsCtce1 peptide.

Group 5: NEEKsCtce2 (peptide representing CbpA R2 loop 2 with laminin receptor binding site and C-terminal TCE sequence (PVVEVNGVTIQVGSRGG; SEQ ID NO:66)); SEQ ID NO:72 for the entire NEEKsCtce2 peptide.

Group 6: NEEKsCtce3 (peptide representing CbpA R2 loop 2 laminin receptor binding site and two tandem N-terminal TCE SEQUENCE (SEQ ID NO:49)); SEQ ID NO:73 for the entire NEEKsCtce3 peptide.

Group 7: NEEKsCtce4 (peptide representing CbpA R2 loop 2 laminin receptor binding site and N-terminal TCE sequence (PVVEVNGVTIQVGSRGG; SEQ ID NO:66)); SEQ ID NO:74 for the entire NEEKsCtce4 peptide.

Specifically, the mice are primed with 200 μg of peptide (or 10 μg of the R2 protein for Group 1) intraperitoneally in Lipid A adjuvant (PHAT). Booster intraperitoneal injections are administered at weeks 2 and 4 with 200 μg of peptide (or 10 μg R2 protein for Group 1) in Lipid A adjuvant (PHAT). Immunogenicity, nasopharyngeal colonization, bacteremia, and survival are investigated in each group of mice, as described below.

Immunogenicity

Serum was collected from each mouse prior to immunization with the peptide/protein of interest (i.e., a naïve serum sample obtained prior to the prime injection) and after the prime and each booster injection. Serum anti-CbpA IgG titers for each group are analyzed by ELISA using full-length recombinant CbpA protein to coat the ELISA plates.

Analysis of Nasopharyngeal Colonization, Bacteremia, and Survival Rates

At week 10, the mice in each group are challenged intranasally with 1×10$^7$ CFU of Tigr4X pneumococci. Nasal lavages and blood from the tail vein are obtained each day after challenge and plated on blood agar plates. Pneumococci are counted the next day, and the log$_{10}$ CFU/ml for nasopharyngeal colonization and blood are analyzed. Survival rates are also monitored and recorded.

Results

As the above study is on-going, no results regarding immunogenicity, nasopharyngeal colonization, bacteremia, and survival rates are yet available.

Example 10

Analysis of CbpA Binding to the Laminin Receptor (LR)

*S. pneumoniae, Haemphilus influenzae,* and *Neisseria meningitidis* attach to and cross the normally impermeable blood-brain barrier (BBB) to cause meningitis. Studies were undertaken to examine the means by which pneumococcus attaches to endothelial cells in the microvasculature, attachment being a prerequisite for invasion and entry into the subarachnoid space.

Bacterial Strains and Mice

*S. pneumoniae* serotype 4, strain Tigr4, and its unencapsulated derivative, T4R, were grown on tryptic soy agar (Difco, Detroit, Mich.) plates supplemented with 3% defibrinated sheep blood or in defined semisynthetic casein liquid media supplemented with 0.5% yeast extract. The T4R choline binding protein A mutant (CbpA-) is previously described and was created by insertion duplication mutagenesis. *Haemophilus influenzae* (ATCC 10211) and *Neisseria meningitidis* (ATCC 13077) were obtained from ATCC (Manassas, Va.). Both were grown on chocolate agar plates at 37° C. Chloramphenicol (50 μg/ml) and erythromycin (1 μg/ml) (Sigma, St. Louis, Mo.) were added to the growth media of the T4R mutants as appropriate.

Female C57Bl/6 mice (The Jackson Laboratory, Bar Harbor, Me.), PAFr KO mice, and wild type littermates were maintained in biosafety level 1 and 2 facilities at the St. Jude Children's Research Hospital Animal Facility. All experimental procedures were done with mice anesthetized with either inhaled isoflurane (Baxter Healthcare) at 2.5% or MKX (1 ml of ketamine [Fort Dodge Laboratories] at 100 mg/ml, 5 ml of xylazine [Miles Laboratories] at 100 mg/ml, and 21 ml of PBS). MKX was administered by intramuscular injection at a dose of 0.05 ml/10 g of body weight.

Production of Recombinant CbpA Constructs

All recombinant CbpA proteins were expressed and purified as previously described. Luo et al (2005) *EMBO J.* 24(1): 34-43. Constructs used in the study include full length CbpA (CbpA-NR12), a construct containing domain 1 and domain 2 (CbpA-R12), domain 1 and 2, individually (CbpA-R1, CbpA-R2, respectively), domain N (CbpA-N) and full length N-terminal CbpA with a point mutation ablating adhesion to the pIgR receptor (CbpA-pIgR). All constructs lacked the choline binding domain.

Intravital Fluorescence Microscopy

Cranial windows, overlying the parietal cortex on one side of the midsagittal suture and extending from the bregma to the lamboid sutures were created in 8 to 10 week old mice. The procedure has been previously described in Gaber et al. (2004) *Brain Res. Protoc.* 13:1-10. Dura mater underlying the windows was punctured and excised. Following surgery, mice were allowed to recover for 10 days before data collection was initiated.

Intravital microscopy was used to visualize attachment of fluorescent latex microspheres to the microvasculature of the brain. Mice with cranial windows were anesthetized, immobilized on a stereotaxic frame, and placed under an industrial-scale microscope (model MM-11, Nikon, Melville, N.Y.) with a camera assembly and bright field and fluorescent light sources. For some experiments, mice were injected retroorbitally with mouse recombinant TNFα (Sigma) (12 μg/kg) one hour prior to microsphere challenge. Yellow-green fluorescent 2 μm microspheres were loaded with CbpA-construct or bovine serum albumin (Sigma) according to the supplier's instructions. Mice were injected with 2.5 μl of a $10^8$ spheres/ml suspension of CbpA-NR12 or BSA (Sigma) coated 2 μm diameter yellow-green fluorescent microspheres per gram of body weight. Video images and still pictures of the injection using an excitation wavelength of 490 nm were captured using MetaMorph software (Universal Imaging, West Chester, Pa.). Images were captured during injection and 3 and 6 minutes following injection. Beads attached to the microvasculature were counted and confirmed by comparison of the cerebral microvasculature to baseline pictures taken prior to injection.

Results from Intravital Fluorescence Microscopy

CbpA coated beads adhere to the microvasculature in a PAFr-independent and TNFα-dependent manner. CbpA-coated fluorescent microspheres were injected intravenously into C57Bl/6 mice and binding to the cerebral endothelium was visualized directly through a cranial window. CbpA beads marginated onto the cerebral vasculature and adhered firmly within three minutes, while BSA coated beads failed to bind. Beads adhered to the brain microvasculature more extensively in animals pretreated with TNF suggesting a eukaryotic receptor was upregulated in response to inflammation. Binding of CbpA beads was independent of PAFr expression since PAFr–/– mice and wild type littermates demonstrated the same level of adherence of beads to the endothelial cells comprising the blood brain barrier.

Affinity Purification with a CbpA Column

CbpA-NR12 was dialyzed against 0.1 M MOPS (pH 7.5) and concentrated to 2.5 mg/ml by Centriplus columns (Amicon, Beverly, Mass.). CbpA-NR12 (10 mg) was covalently conjugated to 1 ml of Affi-Gel 15 (BioRad) in 0.1 M MOPS (pH 7.5) at 4° C. as described in the manufacturer's instructions. The column was sequentially washed with 20 ml of 100 mM glycine (pH 2.5) and 20 ml of PBS/Ca2+/Mg2+buffer (1 mM MgCl and 0.5 mM CaCl), 0.1% Triton X-100, respectively. RBCEC6 cells were grown to complete confluence in 150×25 mm tissue culture dishes and pre-incubated with TNFα at 10 ng/ml for 2 hour. See Blasig et al. (2001) *Microvasc. Res.* 62:114-127. Cell lysates were prepared in a 1% Triton X-100 lysis buffer containing EDTA-free protease inhibitors (Boehringer Mannheim). Cellular debris was removed by centrifugation of the cell lysate at 135,000×g for 1 hr at 4° C. The supernatant was recycled through the CbpA-NR12-affinity column for a period of 4 hr at 4° C. After washing the column with 20 ml of PBS/Ca/Mg buffer and 0.1% Triton X-100, the bound proteins were eluted in 300 μl fractions with 100 mM glycine-HCl (pH 2.5). Proteins eluted in the fractions were visualized by SDS-PAGE and subsequent silver staining of the gel. Bands corresponding to eluted proteins were excised and the proteins in the bands identified by MALDI-TOF analysis in conjunction with a database search performed with Applied Biosystems GPS explorer software. Protein assignments were made on the basis of both MS and MS/MS spectra and the NCBInr (051604) database. Protein identification was performed at the Hartwell Center for Bioinformatics and Biotechnology at St. Jude Children's Research Hospital.

Co-Immunoprecipitation of Laminin Receptor with rCbpA $rBCEC_6$ cells were seeded to 90% confluency in 100 mm dish and activated with TNFα (10 ng/ml). The cells were lysed with 3 ml NP-40 buffer (0.5% NP-40, 500 mM Tris, pH7.4, 150 mM NaCl) and briefly sonicated. The lysate was combined with 4 μg CbpA-NR12 and incubated overnight with 35 μg of either an anti-laminin receptor or an anti-CbpA antibody. Prepared protein-A sepharose beads were added to the mix and incubated for one hour. The samples were washed 7 times with 1 ml NP-40 buffer and ultimately resuspended in 40 μL 2× sample buffer. The samples were boiled for 10 minutes, and the supernatent was harvested. Western blots were performed on samples in accordance with standard protocols. Samples precipitated with the anti-laminin receptor antibody were probed with the anti-CbpA in the western blot. Similarly, samples precipitated with the anti-CbpA antibody were probed with the anti-laminin receptor antibody in the western blot.

Results of Affinity Purification with CbpA Column and Co-Immunoprecipitation Studies CbpA binds to the 37/67 laminin receptor. $RBCEC_6$ cells were activated with TNF and lysed. The endothelial cell lysate was passed over a CbpA column. Bound proteins were eluted, subjected to SDS-PAGE, and analyzed by MOLTI-TOF. Two CbpA-interacting proteins were identified: the 37/67 laminin receptor (LR) and the 70-kDa heat shock protein 5, which has been shown to interact with LR. The identity of the LR-sequenced band was further confirmed by reactivity with an anti-LR antibody (data not shown) and co-immunoprecipitation of LR from endothelial cells with rCbpA. These findings suggest that LR is a cellular receptor for pneumococcal CbpA on blood brain barrier endothelial cells.

Inhibition of Adhesion and Invasion with Laminin and Antiserum to Laminin Receptor Unencapsulated pneumococcal strains T4R and T4R CbpA- were grown to early stationary phase in C+Y. RBCEC6 cells were seeded to 100% confluency in a 24 well plate and activated for 1 hour with TNF (10 ng/ml). Antibody corresponding to amino acids 263-282 of laminin receptor (SEQ ID NO:51), also called anti-LRP 711 (Abcam, Cambridge, Mass.) was added to RBEC6 cells at a dilution of 1:500 for 1 hour. Similarly, laminin from human placenta (Sigma) was added to RBCEC6 cells at a concentration of 5 μg/ml. Cells were washed free of inhibitors and incubated with $1\times10^7$ CFU/ml bacteria. For adhesion assay, after 30 minutes the cells were washed 3× with PBS, trypsinized, diluted 1:10 in PBS and 10 ul plated on blood agar and incubated overnight. Colonies grown represented the number of adherent bacteria. For invasion assays, cells were incubated with the bacteria for 3 hours at 37° C. Following incubation, cells were washed 3× with PBS, incubated for 1 hour with penicillin (10 μg/ml) and gentamicin (200 μg/ml), washed, trypsinized and lysed in 0.025% Triton X-100. 100 uL of lysate was plated on blood agar and grown overnight. *H. influenzae* ATCC 10211 and *N. meningitidis* ATCC 13077 were grown overnight on chocolate agar plates at 37° C. To prepare inoculum for infection, a loopful of bacteria was taken from the overnight plate culture and suspended in PBS. RBCEC6 cells were incubated with the bacteria at a concentration of $1\times10^7$ CFU/ml. Adhesion assays were performed as described above. For each experiment 4 wells per sample were used. Each experiment was performed at a minimum of three times.

Results of Adhesion and Invasion Assays with Laminin and Antiserum to Laminin Receptor To confirm CbpA binding to LRP in an invasive model, activated RBCEC6 cells were incubated with laminin and antiserum to LRP and *S. pneumoniae* adherence and invasion assessed (FIG. 17). Anti-LRP r711 and laminin inhibited pneumococcal adherence (anti-LRP r711: 54%, p<0.001; laminin: 47%, p=0.005) and invasion (anti-LRP r711: 31%, p<0.001; laminin: 36%, p<0.001) indicating that live bacteria did bind to LRP. To confirm this interaction, adherence and invasion assays were also performed using a CbpA deficient mutant. Adhesion and invasion of the CbpA mutant was not affected by the presence of the inhibitors with overall levels of adhesion and invasion reduced in comparison to that of the wild type bacteria. The latter evidence supports a specific interaction between CbpA and LRP. Finally, to exclude the possibility that a second pneumococcal protein mediated adherence, albeit in a CbpA-dependent manner, adherence assays were repeated using latex microspheres labeled with CbpA-NR12. Binding of the CbpA-NR12 labeled beads to RBCEC6 cells was 20-fold greater than that of control thioredoxin labeled beads and was determined to be inhibited by laminin and anti-LRP r711 in a dose dependent manner (FIG. 18); thus providing further evidence that CbpA binds to LRP.

CbpA-Domain Microsphere Adhesion Assays

For adhesion assays RCBEC6 cells were grown to confluence in 24 well plates (Costar, Corning Inc.). Monolayers were treated with TNFα for 2 hours and washed once with PBS. Monolayers were fixed with a 4% paraformaldehyde solution in PBS for 10 minutes and the monolayers washed three times. Cells were blocked overnight at 4° C. with 1% BSA in PBS and inspected prior to use. Adhesion assays were performed by washing the monolayers with PBS and incubating cells with assorted CbpA constructs. Microspheres were labeled with the constructs as indicated by the manufacturer. Microspheres were incubated with the cells for 30 minutes at room temperature to allow for adhesion. Following incubation, cells were washed 3× with PBS and the number of adherent beads determined by fluorescent microscopy. Inhibition assays were performed in a similar manner with exception to incubating cells for 1 hour with purified laminin, anti-LRP 711, naive rabbit serum, or complex sugars dissolved in PBS prior to addition of the microspheres. Cells were incubated for 1 hour with the inhibitors before washing and addition of CbpA-NR12 labeled beads. For all experiments 4 wells per sample were used and the experiments performed in triplicate.

Results of CbpA Domain Microsphere Adhesion Assays

Figure 19:
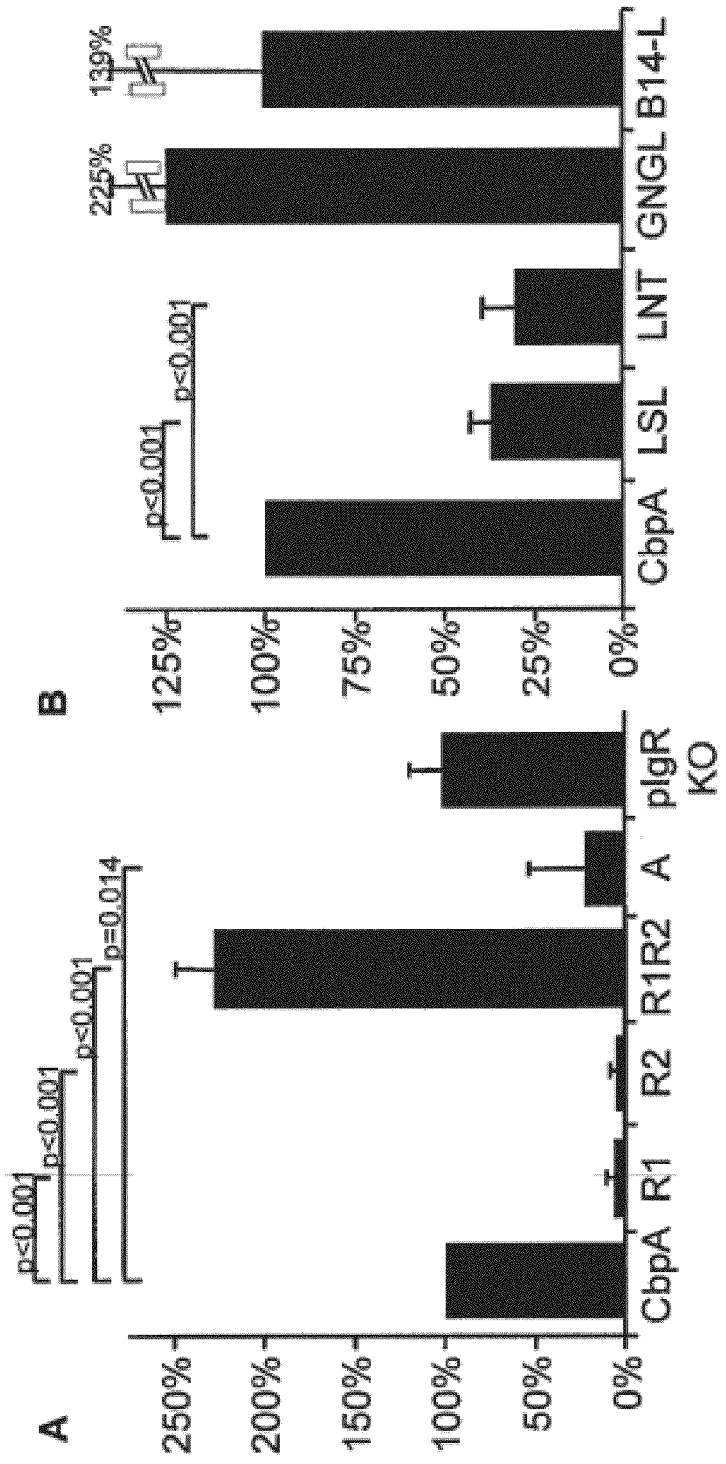

To determine which CbpA domain was responsible for binding LRP, latex microspheres were labeled with varying CbpA constructs and adherence of these beads to RBCEC6 cells determined (FIG. 19). Beads labeled individually with the R1, R2, and the N domain (R1: 10%, p<0.001; R2: 6%, p<0.001; N: 23%, p=0.014) failed to bind RBCEC6 cells, whereas beads labeled with the R12 construct (CbpA residues 175-442; R12: 226%, p=0.001) bound to RBCEC6 cells in a manner greater than full length CbpA (CbpA-NR12). To determine if the portion of CbpA responsible for binding LRP was the same as that which binds to pIgR, beads were labeled with pIgRKO, a full length CbpA construct containing an amino acid substitution that ablates binding of the proteins to pIgR. Beads labeled with pIgRKO adhered to RBCEC6 cells in a manner equivalent to that of full length CbpA. These results indicate that CbpA binds to LRP in a manner that is dependent on the presence of both R1 and R2. Moreover, this binding is not mediated by the same amino acid sequence as that which is responsible for pIgR binding.

CbpA has been demonstrated to bind to immobilized sialic acid (LSL) and lacto-N-neotetraose (LNT) Cundell and Tuomanen (1994) *Microb. Pathog.* 17:361-374. Specifically, CbpA-deficient mutants were unable to bind to these pneumococcal ligands on eukaryotic cells. Galactosugars are known to disrupt the configuration of the laminin receptor required to bind all matrix components. Consistent with this, adherence of CbpA beads was also decreased by L-sialyl-lactose and lacto-N-neotetraose (35±9% and 28±14% of control without sugar, respectively), but not by β1,4 lactose (B14-L; 105±39%). These findings suggest that the CbpA binding site on the laminin receptor is distinguishable from that of laminin/elastin and resides in the carboxy-terminus of the laminin receptor (p263-282; SEQ ID NO:51).

Adhesion of Laminin Receptor or CbpA Peptides to Endothelial Cells

Peptides corresponding to amino acids 161-180 (SEQ ID NO:50) and 263-282 (SEQ ID NO:51) of the laminin receptor (SEQ ID NO:52) were manufactured by Invitrogen (Carlsbad, Calif.). Scrambled versions of residues 161-180 (SEQ ID NO:53) and 263-282 (SEQ ID NO:54) were also made to serve as controls. To block bacterial adhesion to RBEC6 endothelia, the bacteria were incubated 1 hour at room temperature with 25 μg of peptide/$10^7$ CFU bacteria. The bacteria were pelleted by centrifugation and washed 2× with DPBS. Adhesion assays continued as described above.

Results of Adhesion Studies with Laminin Receptor Peptides

CbpA binds to LRP in a manner distinct to prions and laminin. To determine the LRP domain responsible for CbpA binding, activated RBCEC6 cells were pre-incubated with a peptide corresponding to the amino acid sequence responsible for prion and laminin binding (p161-180; SEQ ID NO:50) and a peptide corresponding to the of the anti-LRP 711 epitope (p263-282; SEQ ID NO:51). Following pre-incubation, cells were infected with live bacteria and bacterial adhesion determined (FIG. 20). Adhesion assays demonstrated that pre-incubation of the cells with p161-180 had no effect on bacterial adhesion, whereas in contrast incubation with p263-282 (SEQ ID NO:51) inhibited adherence up to 50% (p=0.003). These findings suggest that CbpA binding to LRP is distinct to that which laminin and prions bind to LRP. Inhibition of binding by the p263-282 peptide (SEQ ID NO:51) and anti-LRP 711 antibody suggests that the carboxy terminus of the protein mediates CbpA binding. Inhibition of CbpA binding by laminin is thereby most likely the result of steric interactions.

Results of Adhesion Studies with CbpA Peptides

CbpA R1/R2EPRNEEK loops bind the carboxy-terminus of the laminin receptor. The RNYPT (SEQ ID NO:62) sequence of R1 and R2 domains of CbpA are known to bind to the epithelial polymeric immunoglobulin receptor (pIgR). To rule out activity of this domain in recognition of the laminin receptor, beads were loaded with a full length CbpA construct containing either RNYPT or an isogenic mutant substituted with RNGPT (SEQ ID NO:63). Beads labeled with CbpA-RGNPT adhered to rBCEC$_6$ cells in a manner equivalent to that of native CbpA (105%±20, p=NS). These results indicated that CbpA binds to the laminin receptor in a manner that is dependent on R1-R2 domains but is not mediated by the same amino acid sequence as that which is responsible for CbpA-pIgR binding.

Two solvent-exposed turns exist in the structure of CbpA-R1 and CbpA-R2: one between the first and second helices of each R domain at the RNYPT sequence and a second between helices 2 and 3 of the R domains at the sequence EPRNEEK in CbpA-R2 (SEQ ID NO:13) and at the sequence EPRDEQK (SEQ ID NO:64) in CbpA-R1. Although the R domains vary considerably in sequence, the EPRNEEK peptide sequence was completely conserved in 32 clinical isolates and laboratory strains of pneumococci (data not shown), suggesting a potential biological importance of this region of CbpA. Single amino acid mutations were introduced within the EPRNEEK sequence and the mutated proteins were used to coat fluorescent beads for adhesion assays. Mutations in residues E391, N394, E395, and E396 yielded no difference in binding of the protein-coated microspheres to rBCEC$_6$ endothelial cells compared to wild type protein. Mutation of P392, however, led to a 50% decrease in binding, and mutations in R393 and K397 decreased adherence to levels observed with cells exposed to the negative control BSA-coated control beads. Conversely, transformation of a CbpA-strain with a vector expressing either native CbpA or CbpA containing glycine substitutions from amino acids 391-397 showed increased adherence. Bacteria expressing CbpA K397G and/or K392G regained adherence to wild type levels while P393G displayed 39% (p=0.0014) less adherence to endothelial cells than did wild type CbpA. These results indicate that the sequence xPRxxxK at the turn between helices 2 and 3 of the R domains is important in binding to the laminin receptor.

To determine the laminin receptor domain responsible for CbpA binding, competitive inhibition studies were performed for binding of bacteria or CbpA-coated beads to activated RBCEC6 cells in the presence of each of the following: the laminin receptor binding domain (p161-180; SEQ ID NO:50), the LMWWML palindromic sequence within the 161-180 laminin-binding domain (SEQ ID NO:58), a peptide corresponding to the anti-laminin receptor antibody epitope (p263-282; SEQ ID NO:51)), two laminin peptides (i.e., YIGSR (SEQ ID NO:59) and LGTIPG (SEQ ID NO:60)) which have been shown to be binding sites for the laminin receptor, and the laminin receptor-binding hexapeptide in elastin (i.e., VGVAPG; SEQ ID NO:61). Pre-incubation of bacteria with p161-180 or the LMWWML peptide had no effect on bacterial adhesion (108±34% of control), whereas p263-282 decreased bacterial adherence to 49±14% of that of the control (p=0.004). Competitive inhibition assays using rCbpA-coated latex beads and the peptides showed similar effect as with the bacteria: p161-180 had no affect on adhesion (93±8% of control), while p263-282 blocked adherence to 38±24% (p=0.014) of control. Pre-incubation of endothelial cells with the laminin peptides YIGSR (SEQ ID NO:59) and LGTIPG (SEQ ID NO:60) and the elastin peptide VGVAPG (SEQ ID NO:61) had no effect on bacterial adherence (data not shown).

Adherence of Other Meningeal Bacterial Pathogens to the Laminin Receptor

*H. influenzae* and *N. meningitidis* interact with the carboxy-terminus of the laminin receptor. To determine if adherence to the laminin receptor extended to *H. influenzae* and *N meningitidis* (other bacterial agents that cause meningitis), adhesion assays were performed using activated $rBCEC_6$ cells. As was observed with *S. pneumoniae*, adherence of *H influenzae* and *N. meningitidis* to the rBCEC6 cells was inhibited by pre-incubation of the cells with anti-laminin receptor antibody (decreased adhesion to 57±7%, p<0.001 and 73±5%, p=0.03 of serum controls, respectively). Pre-incubation of *H. influenzae* and *N. meningitidis* with p263-282 (SEQ ID NO:51), a peptide corresponding to the anti-LRP 711 epitope, also inhibited adhesion by 38%±8, p=0.001 and 51%±17.5, p=0.007, respectively, compared to cells receiving no peptide. Finally, pneumococcal adhesion was inhibited by preincubation of the endothelial cells with *H. influenzae* (decreased adhesion 61%±21 from that of untreated control) and *N. meningitidis* (decreased adhesion 58%±17 from that of untreated control); similar results were obtained using CbpA coated beads (decreased adhesion 49%±12 and 46%±12, respectively). These results suggest that the three meningeal pathogens tested share the laminin receptor as a common target on the blood brain barrier and that the carboxy-terminus of the laminin receptor is the mutual binding domain for all three pathogens.

That which is claimed is:

1. An isolated polypeptide comprising an R2₂loop polypeptide comprising the amino acid sequence set forth in SEQ ID NO: 13, wherein the polypeptide comprises a synthetic linkage and the residues of the synthetic linkage are external to the amino acid sequence of SEQ ID NO: 13, wherein said synthetic linkage stabilizes SEQ ID NO: 13 in a loop confirmation, and said R2₂ loop polypeptide having said synthetic linkage produces a protective immune response against Streptococcus pneumonia infection.

2. The isolated polypeptide of claim 1, wherein the synthetic linkage comprises at least a first cysteine residue and a second cysteine residue, wherein the first and the second cysteine residues form a disulfide bond such that the polypeptide is stabilized in said conformation.

3. The isolated polypeptide of claim 1, wherein the synthetic linkage comprises a synthetic peptide bond between at least a first and a second amino acid residue present in the polypeptide, wherein the synthetic peptide bond stabilizes the polypeptide in said conformation.

4. The isolated polypeptide of claim 1, wherein said amino acid sequence is selected from the group consisting of
 a) a polypeptide comprising the amino acid sequence of SEQ ID NO:1, 3, 5, 9, 27, or 31;
 b) a polypeptide comprising an amino acid sequence having at least 90% sequence identity to SEQ ID NO: 1, 3, 5, 9, 27, or 31, wherein said polypeptide is immunogenic; and,
 c) a polypeptide comprising an amino acid sequence comprising at least 25contiguous amino acids of SEQ ID NO: 1, 3, 5, 9, 27, or 31, wherein said polypeptide produces a protective immune response against Streptococcus pneumonia infection.

5. The isolated polypeptide of claim 2, wherein the polypeptide comprising the first and the second cysteine residues is set forth in SEQ ID NO:17, 29, 33, 43, 71, 72, 73, or 74.

6. The isolated polypeptide of claim 2, wherein
 a) the first and said second cysteine residues or the first and the second amino acid residues forming the synthetic peptide bond flank the amino acid sequence of SEQ ID NO: 1, 3, 5, 9, 27, or 31;
 b) at least one of the first or the second cysteine residues or the first and the second amino acid residues forming the synthetic peptide bond are internal to SEQ ID NO: 1, 3, 5, 9, 27, or 31; or,
 c) both the first and the second cysteine residues or the first and the second amino acid residues forming the synthetic peptide bond are internal to SEQ ID NO: 1, 3, 5, 9, 27, or 31.

7. The polypeptide of claim 1, wherein the polypeptide further comprises an amino acid sequence for a T cell epitope, and wherein the amino acid sequence for the T cell epitope comprises a polypeptide set forth in SEQ ID NO:49, 56, 57, 65 or 66.

8. An immunogenic composition comprising at least one polypeptide according to claim 1 and a pharmaceutically acceptable carrier.

9. The immunogenic composition of claim 8, wherein the polypeptide is present in an amount effective to elicit production of antibodies against *Streptococcus pneumoniae*when administered to an animal.

10. The immunogenic composition of claim 8, wherein the immunogenic composition comprises a second polypeptide comprising the amino acid sequences set forth in SEQ ID NO: 19.

11. A vaccine for treating or preventing a pneumococcal infection comprising at least one polypeptide according to claim 1 in a pharmaceutically acceptable carrier, wherein the polypeptide is present in an amount effective for treating or preventing a pneumococcal infection.

12. The vaccine of claim 11 further comprising an adjuvant.

13. The vaccine of claim 11, wherein the polypeptide further comprises an amino acid sequence comprising a T cell epitope.

14. The vaccine of claim 11, wherein the polypeptide is covalently conjugated to a protein carrier, wherein the protein carrier is tetanus toxoid or diphtheria toxoid.

15. The vaccine of claim 11, wherein the vaccine comprises a second polypeptide.

16. The vaccine of claim 15, wherein the second polypeptide comprises the amino acid sequence set forth in SEQ ID NO: 19.

17. The vaccine of claim 16, wherein each polypeptide further comprises an amino acid sequence comprising a T cell epitope.

18. An isolated polypeptide comprising an R2₁ loop polypeptide comprising the amino acid sequence set forth in SEQ ID NO: 19, wherein the polypeptide comprises a synthetic linkage and the residues of the synthetic linkage are external to the amino acid sequence of SEQ ID NO: 11, wherein said synthetic linkage stabilizes SEQ ID NO: 11 in a loop confirmation, and said R2₁ loop polypeptide having said synthetic linkage produces a protective immune response against *Streptococcus*pneumonia infection.

19. The isolated polypeptide of claim 18, wherein the synthetic linkage comprises at least a first cysteine residue and a second cysteine residue, wherein the first and the second cysteine residues form a disulfide bond such that the polypeptide is stabilized in said conformation.

20. The isolated polypeptide of claim 18, wherein the synthetic linkage comprises a synthetic peptide bond between at least a first and a second amino acid residue present in the polypeptide, wherein the synthetic peptide bond stabilizes the polypeptide in said conformation.

21. The isolated polypeptide of claim 19, wherein the polypeptide comprises the amino acid sequence set forth in SEQ ID NO: 21.

22. The isolated polypeptide of claim 19, wherein
 a) the first and said second cysteine residues or the first and the second amino acid residues forming the synthetic peptide bond flank the amino acid sequence of SEQ ID NO: 1, 3, 5, 7, 19, or 23;

b) at least one of the first or the second cysteine residues or the first and the second amino acid residues forming the synthetic peptide bond are internal to SEQ ID NO: 1, 3, 5, 7, 19, or 23; or, c) both the first and the second cysteine residues or the first and the second amino acid residues forming the synthetic peptide bond are internal to SEQ ID NO: 1, 3, 5, 7, 19, or 23.

23. The polypeptide of claim 20, wherein the polypeptide comprises a synthetic peptide bond between the glutamic acid residue at position 6 of SEQ ID NO:19 and the lysine residue at position 22 of SEQ ID NO:19.

24. The polypeptide of claim 18, wherein the polypeptide further comprises an amino acid sequence for a T cell epitope, and wherein the amino acid sequence for the T cell epitope comprises SEQ ID NO:49, 56, 57, 65 or 66.

25. An immunogenic composition comprising at least one polypeptide according to claim 18 and a pharmaceutically acceptable carrier.

26. The immunogenic composition of claim 25, wherein the polypeptide is present in an amount effective to elicit production of antibodies against *Streptococcus pneumoniae*-when administered to an animal.

27. A vaccine for treating or preventing a pneumococcal infection comprising at least one polypeptide according to claim 18 in a pharmaceutically acceptable carrier, wherein the polypeptide is present in an amount effective for treating or preventing a pneumococcal infection.

28. The vaccine of claim 27 further comprising an adjuvant.

29. The vaccine of claim 27, wherein the polypeptide further comprises an amino acid sequence for a T cell epitope.

30. The vaccine of claim 27, wherein the polypeptide is covalently conjugated to a protein carrier, wherein the protein carrier is tetanus toxoid or diphtheria toxoid.

* * * * *

UNITED STATES PATENT AND TRADEMARK OFFICE
CERTIFICATE OF CORRECTION

| | | |
|---|---|---|
| PATENT NO. | : 8,722,055 B2 | Page 1 of 1 |
| APPLICATION NO. | : 12/442044 | |
| DATED | : May 13, 2014 | |
| INVENTOR(S) | : El Kasmi et al. | |

It is certified that error appears in the above-identified patent and that said Letters Patent is hereby corrected as shown below:

<u>In the Claims</u>

Column 102, lines 12 and 13 (Claim 9), after "*Streptococcus pneumoniae*" insert a space before "when".

Column 102, line 49 (Claim 18), insert a space between "*Streptococcus*" and "*pneumonia*".

Column 104, line 3 (Claim 26), delete "*pneumoniae-*" and insert --*pneumoniae*-- therefor.

Signed and Sealed this
Fourth Day of November, 2014

Michelle K. Lee
*Deputy Director of the United States Patent and Trademark Office*